United States Patent [19]

Furukawa et al.

[11] Patent Number: 5,629,200

[45] Date of Patent: May 13, 1997

[54] PRODUCTION OF OPTICALLY ACTIVE 2-AMINO-1-PHENYLETHANOL DERIVATIVES BY ASYMETRICAL ASSIMILATION

[75] Inventors: Kazuaki Furukawa; Takayuki Abe; Hidekazu Akamatsu; Akinobu Matsuyama, all of Arai; Michio Ito, Joetsu; Noritsugu Yamasaki, Tsukuba; Katsuya Miki, Arai; Kiyoshi Ikura, Tsukuba; Takeshi Ishiguro, Nakakubiki-gun, all of Japan

[73] Assignee: Daicel Chemical Industries, Ltd., Sakai, Japan

[21] Appl. No.: 343,952

[22] Filed: Nov. 17, 1994

[30] Foreign Application Priority Data

| Nov. 18, 1993 | [JP] | Japan | 5-289419 |
| Nov. 24, 1993 | [JP] | Japan | 5-319046 |
| Mar. 10, 1994 | [JP] | Japan | 6-040172 |
| Apr. 21, 1994 | [JP] | Japan | 6-083014 |
| Aug. 4, 1994 | [JP] | Japan | 6-183217 |

[51] Int. Cl.$^6$ .................................................. C12P 41/00
[52] U.S. Cl. ............................................................ 435/280
[58] Field of Search ............................................... 435/280

[56] References Cited

U.S. PATENT DOCUMENTS

| 2,816,059 | 12/1957 | Mills | 167/65 |
| 5,061,727 | 10/1991 | Bloom et al. | 514/465 |
| 5,106,867 | 4/1992 | Bloom et al. | 514/465 |

FOREIGN PATENT DOCUMENTS

| 0040000 | 11/1981 | European Pat. Off. . |
| 0070134 | 1/1982 | European Pat. Off. . |
| 0294995 | 12/1988 | European Pat. Off. . |
| 4627 | 6/1971 | Japan . |
| 285247 | 3/1990 | Japan . |
| 92/05147 | 4/1992 | WIPO . |

OTHER PUBLICATIONS

Castro et al., "The Direction of Epoxide-Ring Opening in the Reaction of Styrene Oxide with Ammonia", J. Org. Chem 19:1444–46 (1954).
Meyers et al., "Asymmetric Addition of Organometallics to Chiral Ketooxazolines. Preparation of Enantiomerically Enriched α—Hydroxy Acids", J. Org. Chem. 45:2785–91 (1980).
Chemical Abstracts, vol. 83, No. 13, 29 Sep. 1975, p. 512, Abstract No. 113941, JP 75–12040.
Chemical Abstracts, vol. 110, No. 19:171710, Ag Biol Chem 53:281–3 (1989).
Chemical Abstracts, vol. 120, No. 25:321535, JP 5–339222.
J. Med. Chem. 1992, (35) pp. 3081–3084 (1992).
Journal of Japan Chemical Society, 1985 (5), pp. 910–913 (1985).
Avison, 'The Application of Lithium Aluminium Hydride to the Preparation of Some Amino–Alkanols', J. Appl. Chem., 1, p. 469 (1951).
Kniezo et al., 'Synthesis and Geometric Isomerism of 4–Substituted 2–Phenylethenyl Isothiocyanates', Coll. Czech. Chem. Comm., 43 (7), pp. 1917–1923 (1978).
McManus et al., 'The Synthesis of Aminoalcohols from Epoxides and Ammonia', Synthetic Communications, 3, (3), pp. 177–180 (1973).
Brenelli et al., 'Enantioselective Synthesis of (R)–(–)–1–Phenylethanolamines Using Baker's Yeast Reduction of Some α–Substituted Methyl Phenyl Ketones', Indian J. Chem., vol. 31B, 1992, pp. 821–823.
Yamazaki et al., 'Biological Method for Preparation of Both Pure Entantiomers of a Chiral Compound: The Case of 2–Amino–1–Phenylethanol', Chemistry Express, vol. 4, No. 9, pp. 621–624 (1989).

*Primary Examiner*—Irene Marx
*Assistant Examiner*—S. Saucier
*Attorney, Agent, or Firm*—Cushman Darby & Cushman IP Group of Pillsbury Madison & Sutro, LLP

[57] ABSTRACT

An (R)-2-amino-1-phenylethanol derivative shown by the general formula (IIa)

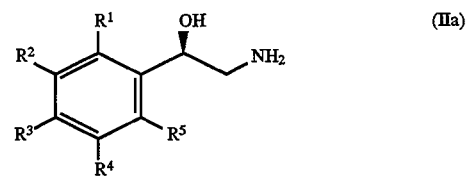

(IIa)

wherein $R^1$ and $R^5$ represent a hydrogen atom, etc.; $R^2$, $R^3$ and $R^4$ independently represent a halogen atom, etc., or a salt thereof, can readily be produced (1) by permitting a microorganism to act on a mixture of corresponding (R)-form and (S)-form to asymmetrically utilize, or (2) by permitting a microorganism to act on a corresponding aminoketone derivative to asymmetrically reduce. An (R,R)-1-phenyl-2-[(2-phenyl-1-alkylethyl) amino]ethanol derivative having a high optical purity can easily be obtained from the compound of the formula (IIa) or a salt thereof. Said derivative is useful as an intermediate for producing an anti-obesity agent.

4 Claims, No Drawings

PRODUCTION OF OPTICALLY ACTIVE 2-AMINO-1-PHENYLETHANOL DERIVATIVES BY ASYMETRICAL ASSIMILATION

FIELD OF THE INVENTION

The present invention relates to processes for producing 2-amino-1-phenylethanol derivatives and optically active enantiomers thereof which are important intermediates for synthesis of (R,R)-1-phenyl-2-[(2-phenyl-1-alkylethyl) amino]ethanol derivatives. The present invention further relates to processes for producing the (R,R)-1-phenyl-2-[(2-phenyl-1-alkylethyl)amino]ethanol derivatives which are useful as medical compounds or intermediate products thereof.

BACKGROUND OF THE INVENTION

As anti-obesity agents or anti-diabetic agents belonging to a new category of agents without using insulin, 1-phenyl-2-[(2-phenyl-1-alkylethyl)amino]ethanol derivatives are noted since the derivatives act selectively on a $\beta_3$-receptor in vivo, thus having extremely low side effects. Pharmacological studies on the 1-phenyl-2-[(2-phenyl-1-alkylethyl) amino]ethanol derivatives have revealed that the $\beta_3$-action substantially depends on (R,R)-form thereof (see J. Med. Chem., 35, 3081 (1992), and U.S. Pat. No. 5,061,727). For example, the above-mentioned U.S. Patent discloses that an (R,R)-5-[2-[[2-(3-chlorophenyl)-2-hydroxyethyl]amino] propyl]-1,3-benzodioxole-2,2-dicarboxylic acid disodium salt has a higher activity than the corresponding (S,S)-form by a factor of 47.

For the production of an optically active 1-phenyl-2-[(2-phenyl-1-alkylethyl)amino]ethanol derivative, there is known an optical resolution of a racemic form or a racemate, or an asymmetric synthesis.

For example, Japanese Patent Application Laid-open No. 320153/1993 (JP-A-5-320153) corresponding to the above mentioned U.S. Pat. No. 5,061,727, U.S. Pat. No. 5,106,867 and Japanese Patent Application Laid-open No. 18340/1983 (JP-A-58-18340) disclose a method of producing an (R,R)-1-phenyl-2-[(2-phenyl-1-alkylethyl)amino]ethanol derivative which comprises (1) allowing a racemic phenylethanol derivative to react with a phenylacetone derivative and a reducing agent such as sodium cyanoborohydride to produce a mixture of four species of optical isomers of a 1-phenyl-2-[(2-phenyl-1-alkylethyl)amino]ethanol derivative, (2) isolating and removing an (R,S)-isomer and an (S,R)-isomer from the mixture, and (3) optically resoluting an (R,R)-isomer and an (S,S)-isomer by a diastereomer method. According to the method, however, it is necessary to isolate and purify the only (R,R)-isomer from a mixture of the four species of optical isomers, therefore, the processes are complicated and the yield is decreased. Further, since large quantities of raw materials are required, the method is also disadvantageous in economical factors.

The above-mentioned U.S. Patents and the Journal of Medicinal Chemistry disclose a method in which an (R)-3-chlorostyrene oxide derivative is allowed to react with an (R)-1-methyl-2-phenylethylamine derivative. The (R)-1-methyl-2-phenylethylamine derivative used as a raw material or reactant in the method, however, has a strong anti-hypnotic or arousal action and it requires particular attention when being handled, and therefore is not suited for a use in commercial production. Further, a lot of steps or processes are required to obtain the above-mentioned (R)-1-methyl-2-phenylethylamine derivative. For example, the (R)-methyl-2-phenylethylamine derivative is prepared from L-DOPA through six steps, namely, introduction of a protective group into an amino group, esterification, reduction of the resulting ester, converting a hydroxyl group to a mesyloxy group, deprotection of the protective group and reduction.

On the other hand, as a method of producing an optically active 2-amino-1-phenylethanol derivative used as a raw material or a reactant for the 1-phenyl-2-[(2-phenyl-1-alkylethyl)amino]ethanol derivative in the present invention, there is known a method of optical resolution of a corresponding racemic form with the use of an optically resoluting agent. Japanese Patent Application Laid-open No. 9979/1989 (JP-A-64-9979) (Japanese Patent Publication No. 48791/1992 (JP-B-4-48791)), for instance, discloses a method of optically resoluting a racemic 2-amino-1-(3-chlorophenyl)ethanol with N-(t-butoxycarbonyl)-D-alanine to obtain an optically active (R)-form.

Further, Japanese Patent Application Laid-open No. 85247/1990 (JP-A-2-85247) discloses a method of optically resoluting a racemic 2-amino-1-(4-chlorophenyl) ethanol with using D-tartaric acid. Moreover, Journal of Japan Chemical Society, 1985, (5), pp. 910 to 913 discloses a method of optically resolving a racemic 2-amino-1-phenylethanol with employing 3-aminobenzoic acid as a optically resoluting agent.

According to these methods, however, the object optically active 2-amino-1-phenylethanol derivative can not be produced expediently and efficiently since the racemic 2-amino-1-phenylethanol derivative to be subjected to the optical resolution can not be obtained in a simple and easy manner with good yield.

For instance, as a method of producing the 2-amino-1-phenylethanol derivative, a method of reducing a nitrogen-containing compound, and a method utilizing an addition reaction of ammonia are known.

As examples of the method of reducing a nitrogen-containing compound, there are known (a) a method of reducing mandelonitrile (see J. Org. Chem., 45 (14), 2785 (1980), Japanese Patent Application Laid-open No. 27/1971 (JP-A-46-27) and the like, (b) a method of reducing mandelic acid amide (refer to J. Appl. Chem., 1 (1951), 469) and (c) a method of reducing a nitro compound (see Coll. Czech. Chem. Comm., 43 (7), 1917 (1978).

In the method (a), however, since mandelonitrile is instable, the hydroxyl group is required to be protected to obtain the object compound with high yield. Further, the reaction is conducted in the presence of a great amount of a reducing agent such as $LiAlH_4$ and $NaBH_4$ and an activating catalyst, thus the method is disadvantageous in economical factors and requires attention to be handled. Moreover, the purity of the obtained 2-amino-1-phenylethanol derivative is low, for example about 95%. In the methods (b) and (c), since a large quantity of $LiAlH_4$ and the like is used as the reducing agent, there are similar problems. According to the method (c) where nitromethane is employed as a solvent it is highly dangerous and needs a sufficient care when handled.

As the method utilizing an addition reaction of ammonia, there is known (d) a method of allowing an epoxy compound to react with ammonia (see Syn. Com., 3 (3), 177, (1973)), and (e) a method of allowing a halohydrin compound to react with ammonia (refer Indian. J. Chem., SECT. B, 31B, 821 (1992)). Although the reaction procedures are expedient, in these methods, however, a 1-amino-2-phenylethanol derivative as a position isomer of the 2-amino-1-phenylethanol derivative is liable to be by-produced. The position-isomer can hardly be removed by an isolating and purifying process generally used such as distillation, recrystallization and extraction, therefore, complicated procedures such as column purification are required.

On the other hand, a method of obtaining an optically active 2-amino-1-phenylethanol with the use of a microorganism is known. That is, Chemistry Express, 4, 9, 621 to 624 (1989) discloses microorganisms belonging to the genus Staphylococcus, the genus Micrococcus, the genus Rhodococcus and the genus Neisseria produce, respectively, an optically active 2-amino-1-phenylethanol from 2-amino-1-phenylethanol and α-aminoacetophenone.

SUMMARY OF THE INVENTION

Accordingly, it is an object of the present invention to provide a process for efficiently producing an optically active (R)-2-amino-1-phenylethanol derivative, which is useful for the efficient production of an (R,R)-1-phenyl-2-[(2-phenyl-1-alkylethyl)amino]ethanol derivative with a good yield, with high yield and optical purity.

It is another object of the present invention to provide a process of producing efficiently the optically active compound, which is useful for the production of the (R,R)-isomer and is available and easy to handle or treat, with high optical purity.

A yet another object of the present invention is to provide a process whereby a 2-amino-1-phenylethanol derivative which is useful for obtaining the optically active compound efficiently can be obtained in an expedient manner with good yield and high purity.

Still another object of the present invention is to provide a process for producing an (R,R)-1-phenyl-2-[(2-phenyl-1-alkylethyl)amino]ethanol derivative having a higher optical purity efficiently with high yield.

A further object of the invention is to provide a process for producing an (S)-form, which is useful for production of the optically active compound, efficiently with good yield.

The present invention further relates to a process for separating the optically active compound, to a process for asymmetrically reducing an aminoketone compound to the optically active compound, and to a use of a microorganism in production of the optically active compounds.

After much studies and efforts to accomplish the above mentioned objects, the present inventors found (i) that a 2-amino-1-phenylethanol derivative having high purity can be obtained by a specific isolation or purification method, (ii) that an optically active (R)- or (S)-2-amino-1-phenylethanol derivative having high optical purity can be obtained efficiently by a method with the aid of a specific microorganism, and (iii) that an optically active (R,R)-1-phenyl-2-[(2-phenyl-1-alkylethyl)amino]ethanol derivative can easily or readily be produced by a reaction of the (R)-form with a phenylacetone derivative, and a reducing reaction of the reaction product of the above reaction with high yield, high optical purity and selectivity. The present invention has been accomplished based on the above findings.

Thus, the present invention provides a process for producing an (R)-2-amino-1-phenylethanol derivative which comprises:

permitting a microorganism or a preparation thereof which is capable of acting on a mixture of enantiomers of a 2-amino-1-phenylethanol compound shown by the general formula (I)

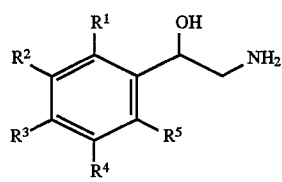

wherein $R^1$, $R^2$, $R^3$, $R^4$ and $R^5$ represent, the same or different, a hydrogen atom, a halogen atom, an optionally substituted lower alkyl group, a hydroxyl group which may be protected with a protective group, an optionally substituted alkoxy group, an optionally substituted cycloalkyloxy group, an optionally substituted aralkyloxy group, an optionally substituted aryloxy group, an optionally substituted lower alkylthio group which may be protected with a protective group, an optionally substituted lower alkoxycarbonyl group, a nitro group, an optionally substituted amino group, or a salt thereof, to produce an (R)-2-amino-1-phenylethanol compound shown by the general formula (IIa)

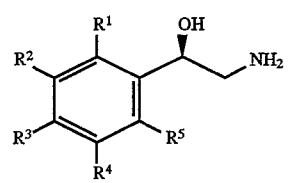

wherein $R^1$, $R^2$, $R^3$, $R^4$ and $R^5$ have the same meanings as defined above, or a salt thereof, to act on the mixture of enantiomers, and harvesting or recovering the product (R)-form or a salt thereof.

The hydroxyl group of the 2-amino-1-phenylethanol derivative shown by the general formula (I) may be protected with a protective group. Such derivative, that is, a compound shown by the general formula (VI)

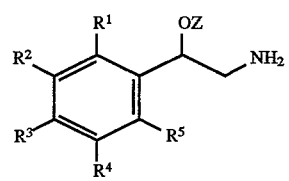

wherein $R^1$, $R^2$, $R^3$, $R^4$ and $R^5$ have the same meanings as defined above; and Z represents a hydrogen atom or a protective group for hydroxyl group, may be prepared by various methods, for example, by a method comprising:

allowing a compound shown by the general formula (III)

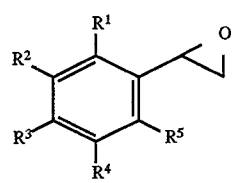

wherein $R^1$, $R^2$, $R^3$, $R^4$ and $R^5$ have the same meanings as defined above, or a compound shown by the general formula (IV)

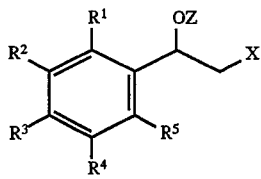

wherein $R^1$, $R^2$, $R^3$, $R^4$, $R^5$ and Z have the same meanings as defined above; and X represents a halogen atom to react with a compound shown by the general formula (V)

wherein Y represents a hydrogen atom or a group which can be left in the reaction, further, when Y is the group which can be left in the reaction, allowing Y to be left, and adding an acid to the reaction product(s) to precipitate or crystallize the compound of the general formula (VI) as a salt to isolate or purify.

The (R)-2-amino-1-phenylethanol derivative of the general formula (IIa) or a salt thereof can also be obtained by, for example, a method comprising:

permitting a microorganism which is capable of acting on a compound shown by the general formula (VII)

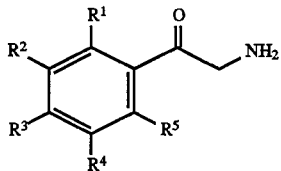

wherein $R^1$, $R^2$, $R^3$, $R^4$ and $R^5$ have the same meanings as defined above, or a salt thereof to produce a corresponding optically active compound shown by the general formula (IIa) or a salt thereof, to act on the compound or a salt thereof and harvesting or recovering the product optically active compound of the general formula (IIa) or a salt thereof.

The optically active compound of the general formula (IIa) or a salt thereof is useful for an intermediate for production of an (R,R)-1-phenyl-2-[(2-phenyl-1-alkylethyl)amino]ethanol derivative.

The present invention further provides a process for producing an (R,R)-1-phenyl-2-[(2-phenyl-1-alkylethyl)amino]ethanol derivative shown by the general formula (XI)

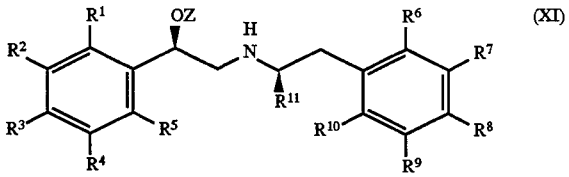

wherein $R^1$, $R^2$, $R^3$, $R^4$ and $R^5$ have the same meanings as defined above;

$R^7$ and $R^8$ represent;

(A) respectively, a group selected from the group consisting of a hydrogen atom, an optionally substituted lower alkyl group, an optionally substituted cycloalkyl group, an optionally substituted aralkyl group, an optionally substituted aryl group, an optionally substituted acyl group, a carboxyl group which may be protected with a protective group, an optionally substituted lower alkoxycarbonyl group, an optionally substituted amino group, an optionally substituted alkylsulfonyl group, an optionally substituted arylsulfonyl group and a hydroxyl group which may be protected with a protective group, or (B) $R^7$ represents a group shown by the formula (IX): —O—$R^{7a}$ and $R^8$ represents a group shown by the formula (X): —O—$R^{8a}$ wherein $R^{7a}$ and $R^{8a}$ may form an optionally substituted ring with the adjacent oxygen atoms;

$R^6$, $R^9$ and $R^{10}$ independently represent a group selected from a group consisting of a hydrogen atom, a halogen atom, an optionally substituted lower alkyl group, an optionally substituted cycloalkyl group, an optionally substituted aralkyl group, an optionally substituted aryl group, a hydroxyl group which may be substituted with a protective group, an optionally substituted alkoxy group, an optionally substituted cycloalkyloxy group, an optionally substituted aralkyloxy group, an optionally substituted aryloxy group, an optionally substituted lower alkylthio group, an optionally substituted aralkylthio group, an optionally substituted acyl group, a carboxyl group which may be protected with a protective group, an optionally substituted lower alkoxycarbonyl group, a nitro group and an optionally substituted amino group; $R^{11}$ represents a lower alkyl group, which comprises:

a reaction of an (R)-2-amino-1-phenylethanol compound shown by the general formula (II)

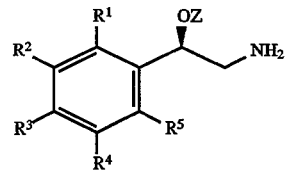

wherein $R^1$, $R^2$, $R^3$, $R^4$, $R^5$ and Z have the same meanings as defined above, or a salt thereof, with a compound shown by the general formula (VIII)

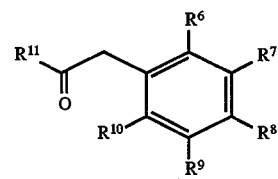

wherein $R^6$, $R^7$, $R^8$, $R^9$, $R^{10}$ and $R^{11}$ have the same meanings as defined above, or a salt thereof, and a reducing reaction of the reaction product of the reaction.

Further, an (S)-form or a salt thereof corresponding to the (R)-form of the general formula (IIa) can be obtained by, for example, a process which comprises:

permitting a microorganism or a preparation thereof which is capable of acting on a mixture of enantiomers of the 2-amino-1-phenylethanol derivative of the general formula (I) or a salt thereof to produce an (S)-form shown by the general formula (XV)

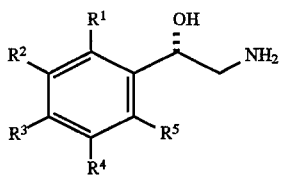

wherein $R^1$, $R^2$, $R^3$, $R^4$ and $R^5$ have the same meanings as defined above, or a salt thereof to act on a mixture of the enantiomers, and harvesting or recovering the product (S)-form or a salt thereof.

The optically active compound of the general formula (XV) or a salt thereof can also be obtained by permitting a microorganism or a preparation thereof which is capable of acting on the compound shown by the general formula (VII) or a salt thereof to produce the corresponding optically active compound of the formula (XV) or a salt thereof, to act on said compound or a salt thereof, and harvesting or recovering the product optically active compound of the general formula (XV) or a salt thereof.

The present invention still further discloses a process for separating an (R)- or (S)-2-amino-1-phenylethanol derivative from a mixture of these enantiomers, a process for asymmetrically reducing the aminoketone compound of the general formula (VII) to the corresponding (R)- or (S)-2-amino-1-phenylethanol derivative, a use of a microorganism or a preparation thereof for the production of the (R)- or (S)-form or a salt thereof.

DETAILED DESCRIPTION OF THE INVENTION

As the halogen atom in $R^1$, $R^2$, $R^3$, $R^4$ and $R^5$ in the general formula (II), (IIa) or the like, there may be mentioned fluorine atom, chlorine atom, bromine atom and iodine atom.

The optionally substituted lower alkyl group includes, for example, (a) an optionally substituted alkyl group having 1 to 4 carbon atoms (for instance, methyl, ethyl, propyl, isopropyl, butyl, isobutyl, s-butyl and t-butyl groups). Examples of the substituent(s) for the $C_{1-4}$ alkyl group includes a hydroxyl group, a $C_{1-4}$ alkoxy group, a benzoyl group, a $C_{6-12}$ aryl group (e.g. phenyl group) which may be substituted with a substituent (for example, a $C_{1-4}$ alkoxy group, etc.), a $C_{1-4}$ alkylthio group and a halogen atom. As examples of such substituted $C_{1-4}$ alkyl group, there may be mentioned (b) a $C_{1-4}$ alkyl group substituted with hydroxyl group(s) (for example, hydroxymethyl, 2-hydroxyethyl, 1,2-dihydroxyethyl, 2,2-dihydroxyethyl, 3,3-dihydroxypropyl group, etc.), (c) a $C_{1-4}$ alkoxy-$C_{1-4}$ alkyl group (for instance, methoxymethyl, ethoxymethyl, t-butoxymethyl, 1-ethoxyethyl, 2-methoxyethyl group, etc.), (d) phenacyl group, (e) a $C_{1-4}$ alkylthio-$C_{1-4}$ alkyl group (e.g. a $C_{1-4}$ alkylthiomethyl such as methylthiomethyl, ethylthiomethyl group, etc.), (f) a $C_{1-4}$ haloalkyl group having 1 or more of halogen atoms such as chloromethyl, 2-chloroethyl, 3-chloropropyl, 4-chlorobutyl, dichloromethyl, trichloromethyl, trifluoromethyl, 2,2,2-trichloroethyl, 2,2,2-trifluoroethyl, 1,1,2,2,2-pentafluoroethyl, and other groups.

As the protective group for hydroxyl group, there may be mentioned protective groups for a hydroxyl group generally employed in the field of organic synthesis. Such protective groups include, for example, (A) a group which forms an ether bond with an oxygen atom, (B) a group which forms an ester bond with an oxygen atom, (C) a group which forms a carbonate with an oxygen atom and (D) a group which forms a sulfonic acid ester with an oxygen atom.

Examples of the group (A) which forms an ether bond with an oxygen atom include (1) an optionally substituted lower alkyl group, (2) an optionally substituted allyl group, (3) an optionally substituted cycloalkyl group, (4) an optionally substituted heterocyclic group, (5) an optionally substituted aralkyl group and (6) an optionally substituted silyl group.

The optionally substituted lower alkyl group (1) includes, for example, (a) an optionally substituted alkyl group having 1 to 4 carbon atoms such as methyl, ethyl, n-propyl, i-propyl, n-butyl, i-butyl, s-butyl and t-butyl groups. The substituents for the $C_{1-4}$ alkyl group include, for example, a $C_{1-4}$ alkoxy group, a $C_{1-4}$ alkoxy-$C_{1-4}$ alkoxy group, a $C_{7-20}$ aralkyloxy group, a benzoyl group, a $C_{1-4}$ alkylthio group, a halogen atom and so on. Examples of such substituted $C_{1-4}$ alkyl group include (b) a $C_{1-4}$ alkoxy-$C_{1-4}$ alkyl group such as methoxymethyl, ethoxymethyl, t-butoxymethyl, 1-methoxyethyl, 1-ethoxyethyl, 2-methoxyethyl (especially a $C_{1-4}$ alkoxy-$C_{1-2}$ alkyl group); (c) a $C_{1-4}$ alkoxy-$C_{1-4}$ alkoxy-$C_{1-4}$ alkyl group such as 2-methoxyethoxymethyl, 2-ethoxymethoxymethyl and the like (specifically a $C_{1-4}$ alkoxy-$C_{1-4}$ alkoxy-$C_{1-2}$ alkyl group); (d) a $C_{7-20}$ aralkyloxy-$C_{1-4}$ alkyl group such as benzyloxymethyl (especially, a $C_{7-20}$ aralkyloxymethyl group); (e) a phenacyl group; (f) a $C_{1-4}$ alkylthio-$C_{1-4}$ alkyl group such as methylthiomethyl, ethylthiomethyl (specifically a $C_{1-4}$ alkylthiomethyl group); and (g) a $C_{1-4}$ haloalkyl group having one or more of halogen atoms such as trichloromethyl, trifluoromethyl, 2,2,2-trichloroethyl, 2,2,2-trifluoroethyl and the like.

As the substituent for the allyl group (2) include, for instance, substituents for the $C_{1-4}$ alkyl group mentioned in the above (1). Examples of the optionally substituted cycloalkyl group (3) include a cycloalkyl group having 3 to 10 carbon atoms such as cyclopropyl, cyclopentyl, cyclohexyl, cycloheptyl, cyclooctyl, cyclononyl and cyclodecyl groups. The substituent(s) for the cycloalkyl group include, for example, a halogen atom, a $C_{1-4}$ alkyl group, and a hydroxyl group.

As the optionally substituted heterocyclic group (4), there may be mentioned, for example, an optionally substituted 5- or 6-membered heterocyclic group having, other than carbon atoms, an oxygen atom or a sulfur atom as a hetero atom. The optionally substituted heterocyclic group may frequently be a non-aromatic perhydroheterocyclic group. The 5- or 6-membered heterocyclic group includes, for instance, tetrahydrofuranyl, tetrahydrothiofuranyl, tetrahydropyranyl and tetrahydrothiopyranyl groups. Examples of the substituents for the heterocyclic group include a halogen atom, a $C_{1-4}$ alkyl group, a $C_{1-4}$ alkoxy group such as methoxy, ethoxy, propoxy, isopropoxy, butoxy, isobutoxy, s-butoxy and t-butoxy, and substituents as mentioned above in lower alkyl group (1).

Practical examples of the optionally substituted heterocyclic group include an optionally substituted tetrahydropyranyl group (e.g. tetrahydropyranyl, 3-bromotetrahydropyranyl, 4-methoxytetrahydropyranyl, etc.), an optionally substituted tetrahydrothiopyranyl group (for example, tetrahydrothiopyranyl, 3-bromotetrahydrothiopyranyl, 4-methoxytetrahydrothiopyranyl, etc.), an optionally substituted tetrahydrofuranyl group (for instance, tetrahydrofuranyl, etc.), and an optionally substituted tetrahydrothiofuranyl group (e.g. tetrahydrothiofuranyl).

Examples of the optionally substituted aralkyl group (5) include an optionally substituted aralkyl group having 7 to 20 carbon atoms (e.g. benzyl, etc.). The substituent for the aralkyl group includes, for instance, a $C_{1-4}$ alkyl group; a $C_{6-12}$ aryl group such as phenyl group; a hydroxyl group, a $C_{1-4}$ alkoxy group; a nitro group; and a halogen atom. Examples of such substituent may be referred to those in the above group (4). Typical examples of the optionally substituted aralkyl group include benzyl, o-chlorobenzyl, o-nitrobenzyl, p-chlorobenzyl, p-methoxybenzyl, p-methylbenzyl, p-nitrobenzyl, 2,6-dichlorobenzyl, diphenylmethyl, trityl and the like.

The substituent for the silyl group (6) includes a $C_{7-20}$ aralkyl group such as benzyl group and substituents as mentioned in the aralkyl group (5). Examples of the optionally substituted silyl group (6) include trimethylsilyl, triethylsilyl, t-butyldimethylsilyl, tribenzylsilyl, triphenylsilyl and so on.

As the group (B) which forms an ester bond with an oxygen atom, there may be mentioned, for example, an optionally substituted acyl group including (1) an acyl group having 1 to 6 carbon atoms which may be substituted with a hydroxyl group, a $C_{1-4}$ alkoxy group, $C_{1-4}$ alkylthio group, a halogen atom and the like (for instance, formyl, acetyl, chloroacetyl, trifluoroacetyl, propionyl, isopropionyl, butyryl, isobutyryl, valeryl, isovaleryl, pivaloyl and the like); (2) a $C_{7-16}$ acyl group having an aromatic ring which may be substituted with, for example, a $C_{1-4}$ alkyl group, a hydroxyl group, a $C_{1-4}$ alkoxy group, a nitro group or a halogen atom (e.g. benzoyl, p-phenylbenzoyl, toluoyl, naphthoyl and others); (3) an acyl group having a heterocyclic ring (e.g. furoyl, thenoyl, nicotinoyl and isonicotinoyl groups) which may be substituted with, for instance, a $C_{1-4}$ alkyl group, a hydroxyl group, a $C_{1-4}$ alkoxy group, a nitro group or a halogen atom.

The group (C) which forms a carbonate with an oxygen atom includes, for instance, (1) a $C_{2-5}$ alkoxycarbonyl group such as methoxycarbonyl, ethoxycarbonyl, propoxycarbonyl, isopropoxycarbonyl, butoxycarbonyl, isobutoxycarbonyl, s-butoxycarbonyl and t-butoxycarbonyl which may be substituted with, for example, a $C_{1-4}$ alkoxy group which may be substituted with a $C_{1-4}$ alkoxy group; a $C_{7-20}$ aralkyloxy group; benzoyl group; a $C_{1-4}$ alkylthio group; or a halogen atom; (2) a $C_{8-20}$ aralkyloxycarbonyl group such as benzyloxycarbonyl, p-methoxybenzyloxycarbonyl, p-methylbenzyloxycarbonyl, p-chlorobenzyloxycarbonyl, o-nitrobenzyloxycarbonyl, etc. which may be substituted with a $C_{1-4}$ alkyl group, a hydroxyl group, a $C_{1-4}$ alkoxy group, a nitro group, a halogen atom, etc., (3) a $C_{7-20}$ aryloxycarbonyl group which may be substituted with a $C_{1-4}$ alkyl group, a hydroxyl group, a $C_{1-4}$ alkoxy group, a nitro group, a halogen atom, etc., such as phenoxycarbonyl, 4-methylphenyloxycarbonyl, 4-nitrophenyloxycarbonyl, 4-chlorophenyloxycarbonyl, naphthyloxycarbonyl and so on.

Examples of the group (D) which forms a sulfonic acid ester with an oxygen atom include, for instance, (1) an alkylsulfonyl group such as a $C_{1-4}$ alkylsulfonyl group which may be substituted with, for instance, a $C_{1-4}$ alkoxy group, a $C_{1-4}$ alkoxy-$C_{1-4}$ alkoxy group, a $C_{7-20}$ aralkyloxy group, a benzoyl group, a $C_{1-4}$ alkylthio group and a halogen atom (e.g. methanesulfonyl, ethanesulfonyl, propanesulfonyl, butanesulfonyl, trichloromethanesulfonyl, trifluoromethanesulfonyl, etc.); (2) an optionally substituted arylsulfonyl group including a $C_{6-20}$ arylsulfonyl group which may be substituted with, for example, a $C_{1-4}$ alkyl group, a hydroxyl group, a $C_{1-4}$ alkoxy group, a nitro group or a halogen atom such as benzenesulfonyl, m-nitrobenzenesulfonyl, p-nitrobenzenesulfonyl, p-chlorobenzenesulfonyl, p-bromobenzenesulfonyl, p-toluenesulfonyl, naphthalenesulfonyl and others.

The optionally substituted alkoxy group includes, for instance, an optionally substituted alkoxy group having 1–4 carbon atoms (e.g. methoxy, ethoxy, propoxy, isopropoxy, butoxy, isobutoxy, s-butoxy, or t-butoxy group) and others. Examples of the substituent for the alkoxy group include a hydroxyl group, a $C_{1-4}$ alkoxy group, a halogen atom and the like. As the substituted alkoxy group, there may be mentioned, for example, a hydroxy-$C_{1-4}$ alkoxy group such as hydroxymethoxy, 2-hydroxyethoxy, 1,2-dihydroxyethoxy, 2,2-dihydroxyethoxy, and 3,3-dipropoxyethoxy groups; a $C_{1-4}$ alkoxy-$C_{1-4}$ alkoxy group such as methoxymethoxy, ethoxymethoxy, 1-ethoxyethoxy, and other groups.

The substituent for the cycloalkyloxy group includes, for instance, a halogen atom, a $C_{1-4}$ alkyl group, a hydroxyl group and the like. Examples of the cycloalkyloxy group include a $C_{3-10}$ cycloalkyloxy group such as cyclopropyloxy, cyclobutyloxy, cyclopentyloxy, cyclohexyloxy, cycloheptyloxy, cyclooctyloxy, cyclononyloxy and cyclodecyloxy groups.

The optionally substituted aralkyloxy group in a $C_{7-20}$ aralkyloxy group which may be substituted with, for examples, a $C_{1-4}$ alkyl group, a $C_{6-12}$ aryl group, a hydroxyl group, a $C_{1-4}$ alkoxy group, a nitro group, or a halogen atom as exemplified above, such as benzyloxy, m-bromobenzyloxy, m-chlorobenzyloxy and other groups.

Examples of the optionally substituted aryloxy group include a $C_{6-16}$ aryloxy group such as phenoxy group. The substituents for the aryloxy group include, for instance, a $C_{1-4}$ alkyl group, a hydroxyl group, a $C_{1-4}$ alkoxy group, a nitro group, a halogen atom as exemplified above.

As the lower alkylthio group, there may be mentioned, for example, a $C_{1-4}$ alkylthio group such as methylthio, ethylthio, propylthio, isopropylthio, butylthio, isobutylthio, s-butylthio, t-butylthio, and other groups. The substituent for the lower alkylthio group includes, for instance, a hydroxyl group, a $C_{1-4}$ alkoxy group, a halogen atom and so on.

Examples of the optionally substituted acyl group include (1) an acyl group having 1 to 6 carbon atoms which may be substituted with a halogen atom, a hydroxyl group, a $C_{1-4}$ alkoxy group, $C_{1-4}$ alkylthio group (for instance, formyl, acetyl, chloroacetyl, trifluoroacetyl, propionyl, isopropionyl, butyryl, isobutyryl, valeryl, isovaleryl, pivaloyl and the like); (2) a $C_{7-16}$ acyl group having an aromatic ring which may be substituted with, for example, a $C_{1-4}$ alkyl group, a hydroxyl group, a $C_{1-4}$ alkoxy group, a nitro group or a halogen atom (e.g. benzoyl, p-phenylbenzoyl, toluoyl, naphthoyl and others); (3) an acyl group having a heterocyclic ring which may be substituted with, for instance, a $C_{1-4}$ alkyl group, a hydroxyl group, a $C_{1-4}$ alkoxy group, a nitro group or a halogen atom (e.g. furoyl, thenoyl, nicotinoyl and isonicotinoyl groups).

The protective group for the carboxyl group includes, for instance, an optionally substituted $C_{1-4}$ alkyl group, an optionally substituted $C_{6-16}$ aryl group, an optionally substituted $C_{7-20}$ aralkyl group, an optionally substituted amino group. As the optionally substituted $C_{1-4}$ alkyl group, etc., there may be mentioned the optionally substituted alkyl group, etc., as exemplified above. The optionally substituted amino group includes an optionally substituted amino group as mentioned just hereinbelow as well as an amino group substituted with a $C_{7-20}$ aralkyl group.

Practical examples of the protected carboxyl group include (a) a $C_{1-4}$ alkoxy-carbonyl group which may be substituted with, for example, a hydroxyl group, a $C_{1-4}$ alkoxy group, etc. (for instance, methoxycarbonyl, ethoxycarbonyl, propoxycarbonyl, butoxycarbonyl, t-butoxycarbonyl, methoxymethoxycarbonyl, methoxyethoxy carbonyl group, etc.), (b) a $C_{6-16}$ aryloxy-carbonyl group which may be substituted with a $C_{1-4}$ alkyl group, a hydroxyl group, a $C_{1-4}$ alkoxy group, a nitro group or a halogen atom (e.g. phenoxycarbonyl, 4-methylphenyloxycarbonyl, 4-methoxyphenyloxycarbonyl, 4-nitrophenyloxycarbonyl, 4-chlorophenyloxycarbonyl, naphthyloxycarbonyl, etc.), (c) a $C_{7-20}$ aralkyloxy-carbonyl group which may be substituted with a $C_{1-4}$ alkyl group, a $C_{6-12}$ aryl group such as phenyl group, a hydroxyl group, a $C_{1-4}$ alkoxy group, a nitro group or a halogen atom (for instance, benzyloxycarbonyl, m-chlorobenzyloxycarbonyl, p-methoxybenzyloxycarbonyl, and others), and (d) a carbamoyl group which may be substituted with a $C_{1-4}$ alkyl group, a $C_{7-20}$ aralkyl group, a $C_{1-6}$ acyl group, a $C_{7-16}$ acyl group having an aromatic group and others (e.g. carbamoyl, benzylaminocarbonyl, etc.).

The carboxyl group may also form a salt. For such a salt, there is no restriction, and examples of the salt include a salt with an inorganic base including an alkali metal salt (e.g. a sodium salt, a potassium salt, etc.), an alkaline earth metal salt such as a magnesium salt, a calcium salt and a barium salt, the other metal salt such as a zinc salt and an aluminum salt, and an ammonium salt; a salt with an organic base including pyridine, a tri-$C_{1-4}$ alkylamine (e.g. trimethylamine, triethylamine, and so on).

Examples of the lower alkoxycarbonyl group include a $C_{2-5}$ alkoxycarbonyl group such as methoxycarbonyl, ethoxycarbonyl, propoxycarbonyl, isopropoxycarbonyl, butoxycarbonyl, isobutoxycarbonyl, s-butoxycarbonyl, t-butoxycarbonyl, and so on. The substituent for the lower alkoxycarbonyl group includes, for instance, those exemplified in the substituent for the alkoxy group as mentioned above.

As the substituents for the optionally substituted amino group, there may be mentioned, for instance, an optionally substituted $C_{1-4}$ alkyl group, an optionally substituted $C_{7-20}$ aralkyl group, an optionally substituted $C_{1-6}$ acyl group, an optionally substituted $C_{7-16}$ acyl group having an aromatic ring, an optionally substituted acyl group having a heterocyclic group, as exemplified above and a substituted carbonyl group. As such substituted carbonyl group, there may be mentioned, for instance, an optionally substituted acyl group and a carboxyl group protected with a protective group as mentioned above.

Typical examples of the optionally substituted amino group include (a) an amino group, (b) an amino group which is substituted with an optionally substituted $C_{1-4}$ alkyl group (for example, methylamino, ethylamino, propylamino, t-butylamino, dimethylamino, diethylthio, dipropylamino, dibutylamino, etc.), (c) an amino group substituted with an optionally substituted $C_{7-20}$ aralkyl group (for instance, benzylamino group and the like), (d) an amino group which is substituted with an optionally substituted $C_{1-6}$ acyl group (for instance, formylamino, acetylamino, valerylamino, isovalerylamino, pivaloylamino, etc.,), (e) an amino group which is substituted with an optionally substituted $C_{7-16}$ acyl group having an aromatic ring (e.g. benzoylamino group, etc.,), (f) an amino group substituted with an optionally substituted acyl group having a heterocyclic ring (for instance, nicotinoylamino group and the like), (g) an amino group which is substituted with a substituted carboxyl group (for instance, acetylaminomethylcarbonylamino, acetylaminoethylcarbonylamino, hydroxymethylcarbonylamino, hydroxyethylcarbonylamino, methoxycarbonylamino, ethoxycarbonylamino group and the like).

Preferred examples of $R^1$ and $R^5$ include a hydrogen atom, a $C_{1-4}$ alkyl group, and others, especially a hydrogen atom.

As the typical examples of $R^2$, $R^3$, $R^4$, there may be mentioned a hydrogen atom, a halogen atom, a $C_{1-4}$ alkyl group which may be substituted with a halogen atom or a hydroxyl group including, for example, a $C_{1-4}$ alkyl group, a $C_{1-4}$ haloalkyl group, a hydroxy-$C_{1-4}$ alkoxy group etc., a hydroxy group, a $C_{1-4}$ alkoxy group, a $C_{7-20}$ aralkyloxy group, a $C_{7-20}$ acyl group having an aromatic ring, an optionally substituted amino group (specifically an amino group which is substituted with a $C_{1-6}$ acyl group) and a nitro group. Specifically preferred ones of $R^2$, $R^3$ and $R^4$ include, for example, a halogen atom.

Examples of the protective group for hydroxyl group in Z include protective groups for hydroxyl group generally used in the field of organic synthesis, such as the protective groups for hydroxyl group (A) to (D) as mentioned above in the explanation of $R^1$ to $R^5$.

Practically, a hydrogen atom, a silyl group which may be substituted with for example a $C_{1-4}$ alkyl group, a $C_{1-6}$ acyl group, especially a hydrogen atom is frequently used as Z.

Typical examples of the compound shown by the general formula (II) include, other than (a) (R)-2-amino-1-phenylethanol, (b) (R)-2-amino-1-phenylethanol derivatives which are protected on the hydroxyl group, (c) (R)-2-amino-1-phenylethanol derivatives which are substituted with a hydroxyl group on the phenyl group, (d) (R)-2-amino-1-phenylethanol derivatives substituted with two hydroxyl groups on the phenyl group, (e) (R)-2-amino-1-phenylethanol derivatives substituted with a halogen atom on the phenyl group, (f) (R)-2-amino-1-phenylethanol derivatives substituted with two halogen atoms on the phenyl group, (g) (R)-2-amino-1-phenylethanol derivatives substituted with three halogen atoms on the phenyl group, (h) (R)-2-amino-1-phenylethanol derivatives substituted with four halogen atoms on the phenyl group, (i) (R)-2-amino-1-phenylethanol derivatives substituted with five halogen atoms on the phenyl group, (j) (R)-2-amino-1-phenylethanol derivatives substituted with an optionally substituted lower alkyl group on the phenyl group, (k) (R)-2-amino-1-phenylethanol derivatives substituted with an optionally substituted lower alkoxy group on the phenyl group, (l) (R)-2-amino-1-phenylethanol derivative substituted with a nitro group on the phenyl group, (m) (R)-2-amino-1-phenylethanol derivatives substituted with an optionally substituted amino group on the phenyl group, (n) (R)-2-amino-1-phenylethanol derivatives substituted with a hydroxyl group which may be protected with a protective group, an optionally substituted cycloalkyloxy group, an optionally substituted aralkyloxy group, an optionally substituted aryloxy group, an optionally substituted amino group, a carboxyl group which may be protected with a protective group, and the like.

Examples of the (R) 2-amino-1-phenylethanol derivatives which are protected on the hydroxyl group (b) include (R)-2-amino-1-phenyl-O-trimethylsilylethanol, (R)-2-amino-1-phenyl-O-t-butyldimethylsilylethanol, (R)-2-amino-1-phenyl-O-tetrahydropyranylethanol, (R)-2-amino-1-phenyl-O-acetylethanol and others.

As the derivatives (c) substituted with a hydroxyl group on the phenyl group, there may be mentioned, for instance, (R)-2-amino-1-(2-hydroxyphenyl)ethanol, (R)-2-amino-1-(3-hydroxyphenyl)ethanol, (R)-2-amino-1-(4- hydroxyphenyl)ethanol, (R)-2-amino-1-(3-methylthio-4-hydroxyphenyl)ethanol, (R)-2-amino-1-(3-hydroxymethyl-4-hydroxyphenyl)ethanol, (R)-2-amino-1-(3-methoxycarbonyl-4-hydroxyphenyl)ethanol, (R)-2-amino-1-(3-hydroxyethoxy-4-hydroxyphenyl)ethanol, (R)-2-amino-1-(3-ethoxymethyl-4-hydroxyphenyl)ethanol, (R)-2-amino-1-[3-hydroxy-5-(1,2-dihydroxypropyl)phenyl]ethanol and so on.

The derivatives (d) substituted with two hydroxyl groups on the phenyl group include, for example, (R)-2-amino-1-(2,3-dihydroxyphenyl)ethanol, (R)-2-amino-1-(2,4-dihydroxyphenyl) ethanol, (R)-2-amino-1-(2,5-dihydroxyphenyl)ethanol, (R)-2-amino-1-(2,6-dihydroxyphenyl)ethanol, (R)-2-amino-1-(3,4-dihydroxyphenyl)ethanol, (R)-2-amino-1-(3,5-dihydroxyphenyl)ethanol, (R)-2-amino-1-(4,5-dihydroxy-3-methylphenyl)ethanol, (R)-2-amino-1-(3,4-dihydroxy-2-methylphenyl)ethanol and others.

Examples of the derivatives (e) substituted with a halogen atom on the phenyl group include an (R)-2-amino-1-(2-halophenyl)ethanol derivative such as (R)-2-amino-1-(2-fluorophenyl)ethanol, (R)-2-amino-1-(2-chlorophenyl)ethanol, (R)-2-amino-1-(2-bromophenyl)ethanol, (R)-2-amino-1-(2-iodophenyl) ethanol, (R)-2-amino-1-(2-chloro-3-hydroxyphenyl)ethanol, (R)-2-amino-1-(2-chloro-4-hydroxyphenyl)ethanol, (R)-2-amino-1-(2-chloro-4-benzyloxyphenyl)ethanol, etc.; an (R)-2-amino-1-(3-halophenyl)ethanol derivative such as (R)-2-amino-1-(3-chlorophenyl)-O-trimethylsilylethanol, (R)-2-amino-1-(3-chlorophenyl)-O-t-butyldimethylsilylethanol, (R)-2-amino-1-(3-chlorophenyl)-O-acetylethanol, (R)-2-amino-1-(3-fluorophenyl)ethanol, (R)-2-amino-1-(3-chlorophenyl)ethanol, (R)-2-amino-1-(3-bromophenyl)ethanol, (R)-2-amino-1-(3-iodophenyl)ethanol, (R)-2-amino-1-(3-fluoro-4-methoxyphenyl)ethanol, (R)-2-amino-1-(3-chloro-4-methoxyphenyl)ethanol, (R)-2-amino-1-(4-benzyloxy-3-chloro-5-methoxyphenyl)ethanol, (R)-2-amino-1-(5-ethoxy-4-benzyloxy-3-chlorophenyl)ethanol, and (R)-2-amino-1-(3-chloro-4-methylthiophenyl)ethanol; an (R)-2-amino-1-(4-halophenyl)ethanol derivative such as (R)-2-amino-1-(4-fluorophenyl)ethanol, (R)-2-amino-1-(4-chlorophenyl)ethanol, (R)-2-amino-1-(4-bromophenyl)ethanol, (R)-2-amino-1-(4-iodophenyl)ethanol, and the like.

As the derivatives (f) substituted with two halogen atoms on the phenyl group, there may be mentioned, for example, (R)-2-amino-1-(2,3-dihalophenyl)ethanol derivatives such as (R)-2-amino-1-(2,3-difluorophenyl) ethanol, (R)-2-amino-1-(2,3-dichloro phenyl)ethanol, (R)-2-amino-1-(2,3-dibromophenyl)ethanol, (R)-2-amino-1-(2,3-diiodophenyl)ethanol, (R)-2-amino-1-(2-fluoro-3-chlorophenyl)ethanol and so on; (R)-2-amino-1-(2,4-dihalophenyl)ethanol derivatives such as (R)-2-amino-1-(2,4-difluorophenyl)ethanol, (R)-2-amino-1-(2,4-dichlorophenyl)ethanol, (R)-2-amino-1-(2,4-dibromophenyl)ethanol, (R)-2-amino-1-(2,4-diiodophenyl)ethanol and the like; (R)-2-amino-1-(2,5-dihalophenyl)ethanol derivatives such as (R)-2-amino-1-(2,5-difluorophenyl)ethanol, (R)-2-amino-1-(2,5-dichloro phenyl)ethanol, (R)-2-amino-1-(2,5-dibromophenyl) ethanol and (R)-2-amino-1-(2,5-diiodophenyl)ethanol; an (R)-2-amino-1-(2,6-dihalophenyl)ethanol derivative such as (R)-2-amino-1-(2,6-difluorophenyl)ethanol, (R)-2-amino-1-(2,6-dichlorophenyl)ethanol, (R)-2-amino-1-(2,6-dibromophenyl)ethanol, (R)-2-amino-1-(2,6-diiodophenyl)ethanol and the like; (R)-2-amino-1-(3,4-dihalophenyl)ethanol derivatives such as (R)-2-amino-1-(3,4-difluorophenyl)ethanol, (R)-2-amino-1-(3,4-dichlorophenyl)ethanol, (R)-2-amino-1-(3,4-dibromophenyl)ethanol, (R)-2-amino-1-(3,4-diiodophenyl) ethanol, (R)-2-amino-1-(3-chloro-4-bromophenyl)ethanol, (R)-2-amino-1-(3,4-dichlorophenyl)-O-trimethylsilylethanol, (R)-2-amino-1-(3,4-dichlorophenyl)-O-acetylethanol and so on; (R)-2-amino-1-(3,5-dihalophenyl)ethanol derivatives such as (R)-2-amino-1-(3,5-difluorophenyl)ethanol, (R)-2-amino-1-(3,5-dichlorophenyl)ethanol, (R)-2-1-(3,5-dibromophenyl)ethanol, (R)-2-amino-1-(3,5-diiodophenyl)ethanol, (R)-2-amino-1-(3,5-difluoro-4-methylaminophenyl)ethanol, (R)-2-amino-1-(3,5-dichloro-4-methylaminophenyl)ethanol, (R)-2-amino-1-(3,5-dibromo-4-methylaminophenyl)ethanol, (R)-2-amino-1-(3,5-dichloro-4-aminophenyl)ethanol, (R)-2-amino-1-(3,5-dichloro-4-methylphenyl)ethanol, (R)-2-amino-1-(3,5-dichloro-4-ethoxycarbonylaminophenyl)ethanol, (R)-2-amino-1-(4-amino-3-bromo-5-fluorophenyl)ethanol and (R)-2-amino-1-(4-amino-3-bromo-5-chlorophenyl )ethanol; and the like.

The derivatives (g) substituted with three halogen atoms on the phenyl group include, for instance, (R)-2-amino-1-(2,3,4-trihalophenyl)ethanol derivatives such as (R)-2-amino-1-(2,3,4-trifluolophenyl)ethanol, (R)-2-amino-1-(2,3,4-trichlorophenyl)ethanol, (R)-2-amino-1-(2,3,4-tribromophenyl)ethanol, (R)-2-amino-1-(2,3,4-triiodophenyl)ethanol and so on; (R)-2-amino-1-(2,3,5-trihalophenyl)ethanol derivatives such as (R)-2-amino-1-(2,3,5-trifluorophenyl)ethanol, (R)-2-amino-1-(2,3,5-trichlorophenyl)ethanol, (R)-2-amino-1-(2,3,5-tribromophenyl)ethanol and (R)-2-amino-1-(2,3,5-triiodophenyl)ethanol; (R)-2-amino-1-(2,3,6-trihalophenyl) ethanol derivatives such as (R)-2-amino-1-(2,3,6-trifluolophenyl)ethanol, (R)-2-amino-1-(2,3,6-trichlorophenyl)ethanol, (R)-2-amino-1-(2,3,6-tribromophenyl)ethanol, (R)-2-amino-1-(2,3,6-triiodophenyl)ethanol and the like; (R)-2-amino-1-(2,4,5-trihalophenyl)ethanol derivatives such as (R)-2-amino-1-(2,4,5-trifluolophenyl)ethanol, (R)-2-amino-1-(2,4,5-trichlorophenyl)ethanol, (R)-2-amino-1-(2,4,5-tribromophenyl)ethanol and (R)-2-amino-1-(2,4,5-triiodophenyl)ethanol; (R)-2-amino-1-(2,4,6-trihalophenyl) ethanol derivatives such as (R)-2-amino-1-(2,4,6-trifluolophenyl)ethanol, (R)-2-amino-1-(2,4,6-trichlorophenyl)ethanol, (R)-2-amino-1-(2,4,6-tribromophenyl)ethanol, (R)-2-amino-1-(2,4,6-triiodophenyl)ethanol and so on; an (R)-2-amino-1-(3,4,5-trihalophenyl)ethanol derivative such as (R)-2-amino-1-(3,4,5-trifluorophenyl)ethanol, (R)-2-amino-1-(3,4,5-trichlorophenyl)ethanol, (R)-2-amino-1-(3,4,5-tribromophenyl)ethanol, (R)-2-amino-1-(3,4,5-triiodophenyl)ethanol, (R)-2-amino-1-(3-chloro-4,5-difluorophenyl)ethanol, (R)-2-amino-1-(3-fluoro-4,5-dichlorophenyl)ethanol and the like.

Examples of the derivatives (h) substituted with four halogen atoms on the phenyl group include an (R)-2-amino-1-(2,3,4,5-tetrahalophenyl)ethanol derivative such as (R)-2-amino-1-(2,3,4,5-tetrafluorophenyl)ethanol, (R)-2-amino-1-(2,3,4,5-tetrachlorophenyl)ethanol, (R)-2-amino-1-(2,3,4,5-tetrabromophenyl)ethanol, (R)-2-amino-1-(2,3,4,5-tetraiodophenyl)ethanol and others; an (R)-2-amino-1-(2,3,4,6-tetrahalophenyl)ethanol derivative such as (R)-2-amino-1-(2,3,4,6-tetrafluorophenyl)ethanol, (R)-2-amino-1-(2,3,4,6-tetrachlorophenyl)ethanol, (R)-2-amino-1-(2,3,4,6-tetrabromophenyl)ethanol, (R)-2-amino-1-(2,3,4,6-tetraiodophenyl)ethanol, etc.; an (R)-2-amino-1-(2,3,5,6-tetrahalophenyl)ethanol derivative such as (R)-2-amino-1-(2,3,5,6-tetrafluorophenyl)ethanol, (R)-2-amino-1-(2,3,5,6-tetrachlorophenyl)ethanol, (R)-2-amino-1-(2,3,5,6- tetrabromophenyl)ethanol, (R)-2-amino-1-(2,3,5,6-tetraiodophenyl)ethanol and the like.

The derivatives (i) substituted with five halogen atoms on the phenyl group include, for instance, (R)-2-amino-1-(2,3,4,5,6-pentafluorophenyl)ethanol, (R)-2-amino-1-(2,3,4,5,6-pentachlorophenyl)ethanol, (R)-2-amino-1-(2,3,4,5,6-pentabromophenyl)ethanol, (R)-2-amino-1-(2,3,4,5,6-pentaiodophenyl)ethanol and so on.

Examples of the derivatives (j) substituted with an optionally substituted lower alkyl group on the phenyl group include an (R)-2-amino-1-(2-$C_{1-4}$-alkylphenyl)ethanol derivative such as (R)-2-amino-1-(2-methylphenyl)ethanol, (R)-2-amino-1-(2-ethylphenyl)ethanol, (R)-2-amino-1-(2-propylphenyl)ethanol, (R)-2-amino-1-(2-t-butylphenyl)ethanol and (R)-2-amino-1-(2-methylphenyl)-O-trimethylsilylethanol; an (R)-2-amino-1-(3-$C_{1-4}$ alkyl-phenyl)ethanol derivative such as (R)-2-amino-1-(3-methylphenyl)ethanol, (R)-2-amino-1-(3-ethylphenyl)ethanol, (R)-2-amino-1-(3-propylphenyl)ethanol, (R)-2-amino-1-(3-t-butylphenyl)ethanol and (R)-2-amino-1-(3-methylphenyl)-O-trimethylsilylethanol; an (R)-2-amino-1-(4-$C_{1-4}$ alkyl-phenyl)ethanol derivative such as (R)-2-amino-1-(4-methylphenyl)ethanol, (R)-2-amino-1-(4-ethylphenyl)ethanol, (R)-2-amino-1-(4-propylphenyl)ethanol, (R)-2-amino-1-(4-t-butylphenyl)ethanol and (R)-2-amino-1-(4-methylphenyl)-O-trimethylsilylethanol; an (R)-2-amino-1-(2-$C_{1-4}$ haloalkyl-phenyl)ethanol derivative such as (R)-2-amino-1-(2-chloromethylphenyl) ethanol, (R)-2-amino-1-[2-(2-chloroethyl)phenyl]ethanol, (R)-2-amino-1-[2-(3-chloropropyl)phenyl]ethanol, (R)-2-amino-1-[2-(4-chlorobutyl)phenyl]ethanol, (R)-2-amino-1-(2-trichloromethylphenyl)ethanol, (R)-2-amino-1-(2-trifluoromethylphenyl)ethanol and (R)-2-amino-1-(2-chloromethylphenyl)-O-trimethylsilylethanol; an (R)-2-amino-1-(3-$C_{1-4}$-haloalkyl-phenyl)ethanol derivative such as (R)-2-amino-1-(3-chloromethylphenyl)ethanol, (R)-2-amino-1-[3-(2-chloroethyl) phenyl]ethanol, (R)-2-amino-1-[3-(3-chloropropyl)phenyl]ethanol, (R)-2-amino-1-[3-(4-chlorobutyl)phenyl]ethanol, (R)-2-amino-1-(3-trichloromethylphenyl)ethanol, (R)-2-amino-1-(3-trifluoromethylphenyl)ethanol, (R)-2-amino-1-(3-trifluoromethylphenyl)-O-trimethylsilylethanol, (R)-2-amino-1-(3-trifluoromethylphenyl)-O-acetylethanol, (R)-2-amino-1-[3-(1,1,2,2,2-pentafluoroethyl)phenyl]-O-acetylethanol and (R)-2-amino-1-(3-chloro-methylphenyl)-O-trimethylsilylethanol; an (R)-2-amino-1-(4-$C_{1-4}$ haloalkyl-phenyl)ethanol derivative such as (R)-2-amino-1-(4-chloromethylphenyl)ethanol, (R)-2-amino-1-[4-(2-chloroethyl)phenyl]ethanol, (R)-2-amino-1-[4-(3-chloropropyl)phenyl]ethanol, (R)-2-amino-1-[4-(4-chlorobutyl)phenyl]ethanol, (R)-2-amino-1-(4-trichloromethylphenyl)ethanol, (R)-2-amino-1-(4-trifluoromethylphenyl)ethanol and (R)-2-amino-1-(4-chloromethylphenyl)-O-trimethylsilylethanol; an (R)-2-amino-1-[3-(hydroxy-$C_{1-4}$ alkyl) phenyl]ethanol derivative such as (R)-2-amino-1-[3-(hydroxymethyl)phenyl]ethanol and so on.

As the derivatives (k) substituted with a lower alkoxy group on the phenyl group, there may be mentioned, for example, a derivative substituted with one lower alkoxy group on the phenyl group such as (R)-2-amino-1-(2-methoxyphenyl)ethanol, (R)-2-amino-1-(3-methoxyphenyl)ethanol, (R)-2-amino-1-(4-methoxyphenyl)ethanol, (R)-2-amino-1-(2-ethoxyphenyl)ethanol, (R)-2-amino-1-(3-ethoxyphenyl)ethanol, (R)-2-amino-1-(4-ethoxyphenyl)ethanol and so on; a derivative substituted with two lower alkoxy groups on the phenyl group such as (R)-2-amino-1-(2,3-dimethoxyphenyl)ethanol, (R)-2-amino-1-(2,3-diethoxyphenyl)ethanol, (R)-2-amino-1-(2,4-dimethoxyphenyl)ethanol, (R)-2-amino-1-(2,4-diethoxyphenyl)ethanol, (R)-2-amino-1-(2,5-dimethoxyphenyl)ethanol, (R)-2-amino-1-(2,5-diethoxyphenyl)ethanol, (R)-2-amino-1-(2,6-dimethoxyphenyl)ethanol, (R)-2-amino-1-(2,6-diethoxyphenyl)ethanol, (R)-2-amino-1-(3,4-dimethoxyphenyl)ethanol, (R)-2-amino-1-(3,4-diethoxyphenyl)ethanol, (R)-2-amino-1-(3,5-dimethoxyphenyl)ethanol, (R)-2-amino-1-(3,5-diethoxyphenyl)ethanol and (R)-2-amino-1-(3-hydroxyethoxy-4-t-butoxyphenyl)ethanol; a derivative which is substituted with an alkoxy group and a hydroxyl group on the phenyl group such as (R)-2-amino-1-(2-hydroxy-3-methoxyphenyl)ethanol, (R)-2-amino-1-(2-hydroxy-4-methoxyphenyl)ethanol, (R)-2-amino-1-(2-hydroxy-5-methoxyphenyl)ethanol, (R)-2-amino-1-(2-hydroxy-6-methoxyphenyl)ethanol, (R)-2-amino-1-(3-hydroxy-2-methoxyphenyl)ethanol, (R)-2-amino-1-(3-hydroxy-4-methoxyphenyl)ethanol, (R)-2-amino-1-(3-hydroxy-5-methoxyphenyl)ethanol, (R)-2-amino-1-(3-hydroxy-6-methoxyphenyl)ethanol, (R)-2-amino-1-(4-hydroxy-2-methoxyphenyl)ethanol, (R)-2-amino-1-(4-hydroxy-3-methoxyphenyl)ethanol, (R)-2-amino-1-(5-hydroxy-2-methoxyphenyl)ethanol, (R)-2-amino-1-(5-hydroxy-3-methoxyphenyl)ethanol, (R)-2-amino-1-(6-hydroxy-2-methoxyphenyl)ethanol, (R)-2-amino-1-(6-hydroxy-3-methoxyphenyl)ethanol, (R)-2-amino-1-(2-hydroxy-3-ethoxyphenyl)ethanol, (R)-2-amino-1-(2-hydroxy-4-ethoxyphenyl)ethanol, (R)-2-amino-1-(2-hydroxy-5-ethoxyphenyl)ethanol, (R)-2-amino-1-(2-hydroxy-6-ethoxyphenyl)ethanol, (R)-2-amino-1-(3-hydroxy-2-ethoxyphenyl)ethanol, (R)-2-amino-1-(3-hydroxy-4-ethoxyphenyl)ethanol, (R)-2-amino-1-(3-hydroxy-5-ethoxyphenyl)ethanol, (R)-2-amino-1-(3-hydroxy-6-ethoxyphenyl)ethanol, (R)-2-amino-1-(4-hydroxy-2-ethoxyphenyl)ethanol, (R)-2-amino-1-(4-hydroxy-3-ethoxyphenyl)ethanol, (R)-2-amino-1-(5-hydroxy-2-ethoxyphenyl)ethanol, (R)-2-amino-1-(5-hydroxy-3-ethoxyphenyl)ethanol, (R)-2-amino-1-(6-hydroxy-2-ethoxyphenyl)ethanol, (R)-2-amino-1-(6-hydroxy-3-ethoxyphenyl)ethanol and others.

The derivatives (1) substituted with a nitro group on the phenyl group include, for example, (R)-2-amino-1-(2-nitrophenyl)ethanol, (R)-2-amino-1-(3-nitrophenyl)ethanol, (R)-2-amino-1-(2-methyl-3-nitrophenyl)ethanol, (R)-2-amino-1-(4-nitrophenyl)ethanol and the like.

Examples of the derivative (m) substituted with an optionally substituted amino group on the phenyl group include (R)-2-amino-1-(3-aminophenyl)ethanol, (R)-2-amino-1-(3-amino-4-methoxyphenyl)ethanol, (R)-2-amino-1-(3-acetylaminophenyl)ethanol, (R)-2-amino-1-(4-acetylaminophenyl)ethanol, (R)-2-amino-1-(3-acetylamino-4-hydroxyphenyl)ethanol, (R)-2-amino-1-(3-acetylamino-4-methoxyphenyl)ethanol, (R)-2-amino-1-(3-acetylamino-4-benzyloxyphenyl)ethanol, (R)-2-amino-1-(3-acetylaminomethylcarbonylamino-4-hydroxyphenyl)ethanol, (R)-2-amino-1-(3-formylamino-4-hydroxyphenyl)ethanol, (R)-2-amino-1-(3-hydroxymethylcarbonylamino-4-hydroxyphenyl)ethanol, (R)-2-amino-1-[3-hydroxymethylcarbonylamino-4-(p-methoxyphenyl)methylphenyl]ethanol, (R)-2-amino-1-(5-formylamino-3-hydroxyphenyl)ethanol, (R)-2-amino-1-(3-carbamoyl-4-hydroxyphenyl)ethanol, and so on.

As the derivatives (n) substituted with a hydroxyl group which may be protected with a protective group, an optionally substituted cycloalkyloxy group, an optionally substituted aralkyloxy group, an optionally substituted aryloxy group, an optionally substituted acyl group, or a carboxyl group which may be protected with a protective group, there may be mentioned, for example, (R)-2-amino-1-(2-benzyloxyphenyl)ethanol, (R)-2-amino-1-(2-benzylcarbonylphenyl)ethanol, (R)-2-amino-1-(2-benzylcarbonyloxyphenyl)ethanol, (R)-2-amino-1-(3-methoxycarbonyl-4-cyclohexyloxyphenyl)ethanol, (R)-2-amino-1-(3,4-dibenzyloxyphenyl)ethanol, (R)-2-amino-1-(3-hydroxymethyl-4-benzyloxyphenyl)ethanol, (R)-2-amino-1-(3,5-dibenzyloxyphenyl)ethanol, (R)-2-amino-1-(3,5-di-t-butoxycarbonylphenyl)ethanol and the like.

Preferred examples of the compound shown by the general formula (II) as exemplified above include (R)-2-amino-1-phenylethanol; an (R)-2-amino-1-phenylethanol derivative substituted with a halogen atom(s) on the phenyl group (for example, a derivative substituted with one or two of halogen atoms, specifically a derivative substituted with one or two of halogen atoms on the 2-, 3- or 4-position of the phenyl group such as an (R)-2-amino-1-(3-halophenyl) ethanol derivative, (R)-2-amino-1-(4-halophenyl)ethanol derivative, an (R)-2-amino-1-(3,4-dihalophenyl)ethanol derivative and the like); an (R)-2-amino-1-phenylethanol derivative substituted, on the phenyl group, with an optionally substituted $C_{1-4}$ alkyl group, an optionally substituted $C_{1-4}$ alkoxy group or an optionally substituted amino group such as an (R)-2-amino-1-(3-$C_{1-4}$ alkyl-phenyl)ethanol derivative, an (R)-2-amino-1-(3-$C_{1-4}$ haloalkyl-phenyl) ethanol derivative, an (R)-2-amino-1-(3-$C_{1-4}$-alkoxy-phenyl)ethanol derivative, an (R)-2-amino-1-(3-$C_{1-6}$acylaminophenyl)ethanol derivative, an (R)-2-amino-1-(4-$C_{1-4}$ alkyl-phenyl)ethanol derivative, an (R)-2-amino-1-(4-$C_{1-4}$ haloalkyl-phenyl)ethanol derivative, an (R)-2-amino-1-(4-$C_{1-4}$ alkoxy-phenyl)ethanol derivative, an (R)-2-amino-1-(4-$C_{1-6}$-acylaminophenyl)ethanol derivative and others.

The (R)-2-amino-1-phenylethanol derivative shown by the general formula (II) wherein Z is a hydrogen atom, namely, the compound shown by the general formula (IIa) can be prepared by various methods, for example, a chemical synthetic method, and the compound of the general formula (IIa) can advantageously be produced by a method utilizing a microorganism or a preparation thereof.

The optically active (R)-form shown by the general formula (IIa) can be readily or easily prepared, for example, by (A) permitting a specific microorganism or a preparation thereof to act on a mixture of the enantiomers of the 2-amino-1-phenylethanol derivative of the general formula (I) or a salt thereof, or (B) permitting a specific microorganism or a preparation thereof to act on the compound of the general formula (VII) or a salt thereof, and harvesting or recovering the product (R)-2-amino-1-phenylethanol derivative.

The optically active compound can also be prepared by, for instance, (C) a method for obtaining the compound by allowing an aminating agent to act on an optically active compound of the formula (III) or an optically active compound of the formula (IV), adding an acid to the reaction product(s) to isolate or purify by precipitating or crystallizing the optically active compound of the formula (VI) as a salt, and further, when Z in the formula (VI) is a protective group for hydroxyl group, cleaving the protective group; or (D) a method comprising permitting an aminating agent to act on a compound shown by the formula (III) or a compound shown by the formula (IV), adding an optically active acid to the reaction product(s) to precipitate or crystallize the optically active compound of the formula (VI) as a salt for isolation or purification, and further, where Z in the formula (VI) is the protective group for hydroxyl group, cleaving the protective group to obtain the optically active compound.

The method (A) just mentioned above is explained hereinbelow.

In this method, a mixture of the enantiomers of the 2-amino-1-phenylethanol derivative used as a raw material can be prepared by, for instance, (a) a method which comprises allowing a trialkylsilylcyanide such as trimethylsilylcyanide to react with a corresponding benzaldehyde derivative in the presence of a Lewis acid such as anhydrous aluminium chloride to produce an O-trialkylsilylmandelonitrile derivative such as O-trimethylsilylmandelonitrile derivative, subjecting the resultant compound to a treatment with a reducing agent such as sodium borohydride, and to hydrolysis with an acid (see Japanese Patent Application Laid-open No. 5445/1981 (JP-A-56-5445) and U.S. Pat. No. 5,061,727 as mentioned above) (hereinafter referred to as reducing method), (b) a method which comprises allowing an aminating agent such as $NH_3$ to act on a corresponding compound (styrene oxide derivative) to obtain the product compound wherein the epoxide ring is opened (hereinafter referred to as styrene oxide-aminating method), (c) a method allowing an aminating agent such as $NH_3$ to act on the corresponding styrene halohydrin derivative (hereinafter briefly referred to as halohy-drin-aminating method), or the like.

In these methods, the hydroxyl group of the compound of the general formula (I) may be protected with a proper protective group. Such compound where the hydroxyl group may be protected with a protective group is shown by the general formula (VI), and after completion of the reaction, the compound of the general formula (I) can be easily be obtained by cleaving the protecting group. Examples of the protective group for the hydroxyl group include those exemplified in the explanation of Z in the formula (II).

According to the styrene oxide-aminating method (b) and halohydrin-aminating method (c), differing from the reducing method (a), it is not necessary to use a large amount of a reducing agent having a high cost, and the object compound can easily or readily be obtained by using an aminating agent.

In the styrene oxide-aminating method (b), the styrene oxide derivative used as a raw material can be obtained in a conventional manner, for example, by oxidizing a corresponding styrene derivative.

As the aminating agent, for example, a compound shown by the general formula (V)

$$Y-NH_2 \qquad (V)$$

wherein Y represents a hydrogen atom or a group which can be left in the reaction, can be employed. Examples of the group represented by Y which can be left in the reaction include an optionally substituted $C_{1-4}$ alkyl group (for example, allyl group; phenacyl group; a $C_{1-6}$ acyloxy-$C_{1-4}$ alkyl group such as 3-acetoxypropyl group; an optionally substituted $C_{1-4}$ alkoxy-$C_{1-4}$ alkyl group such as methoxymethyl, 2-chloroethoxymethyl group and so on; a $C_{7-16}$ aralkyloxy-$C_{1-4}$ alkyl group such as benzyloxymethyl group; an optionally substituted a $C_{7-16}$ aralkyl group (for instance, benzyl, triphenylmethyl, a $C_{1-4}$ alkoxy-$C_{7-16}$ aralkyl group such as 3,4-dimethoxybenzyl, di(p-methoxyphenyl)methyl and (p-methoxyphenyl) diphenylmethyl group) and others. As the $C_{1-4}$ alkyl group and the like, there may be employed the $C_{1-4}$ alkyl group and the like as mentioned in the explanation of $R^1$ to $R^5$. Practical examples of Y include a hydrogen atom.

The reaction may be carried out in an inert solvent. The solvent includes, for instance, alcohols including lower alcohols (e.g. a $C_{1-4}$ alcohol such as methanol, ethanol, propanol, t-butanol); aromatic hydrocarbons such as benzene, toluene, xylene, ethylbenzene and the like; aliphatic hydrocarbons such as pentane, hexane, heptane, octane and so on; alicyclic hydrocarbons such as cyclohexane, methylcyclohexane, etc.; halogenated hydrocarbons such as carbon tetrachloride, chloroform, dichloromethane and 1,2-dichloroethane; ethers such as diethyl ether, dibutyl ether, dioxane, tetrahydrofuran and others; ketones such as acetone, methyl ethyl ketone and the like; esters such as methyl acetate and ethyl acetate. As such solvent, alcohols can frequently be used.

The conditions of the reaction can be selected from a suitable range depending on the species of the aminating agent and other factors, as far as the yield and the like will not be affected adversely, and the reaction temperature is, for example, about 0° to 80° C. and preferably about 20° to 60° C., and the reaction time is, usually, about from 5 minutes to 24 hours.

In the above-mentioned reaction, where Y is the group which can be left in the reaction, the compound of the general formula (I) can readily or easily be obtained by allowing Y to be left in a conventional manner.

In the halohydrin-aminating method (c), the reaction may be conducted in the same manner as in the styrene oxide-aminating method (b), except that the corresponding styrene halohydrin derivative is employed as a raw material. The styrene halohydrin derivative used as a raw material can be obtained by a conventional manner, for example, by halogenating a corresponding acetophenone derivative and reducing the resulting compound.

In the aminating methods (b) and (c), while depending on the reaction conditions, a by-product such as a position isomer of the object compound shown by the general formula (XVI)

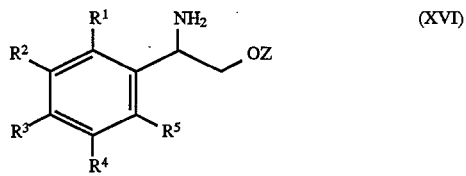

wherein $R^1$, $R^2$, $R^3$, $R^4$, $R^5$ and Z have the same meanings as defined above, or a dimer shown by the general formula (XVII) and (XVII')

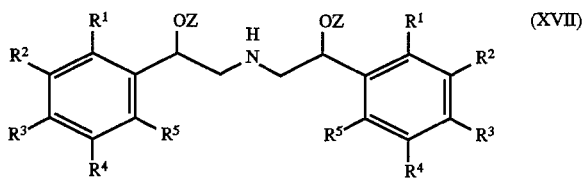

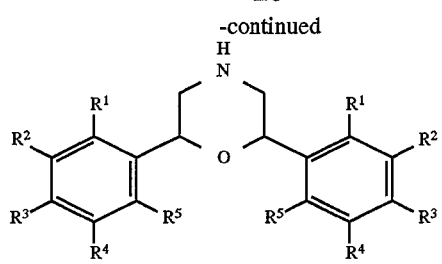

wherein $R^1$, $R^2$, $R^3$, $R^4$, $R^5$ and Z have the same meanings as defined above, or the like. The amount of the by-product (S) may depend on the species of the compound, the reaction conditions and other factors, and is, usually, in the styrene oxide-aminating method, such that the ratio of the 2-amino-1-phenylethanol derivative of the general formula (I) : the position isomer of the general formula (XVI) : other by-product such as the dimer equals about 7:1:2 by weight. The proportions of the 2-amino-1-phenylethanol derivative of the general formula (I), the position isomer and dimer thereof can for example be analyzed by high performance liquid chromatography or the like.

The 2-amino-1-phenylethanol derivative can be isolated or purified by utilizing difference in the basicity and/or solubility between the derivative and the by-product(s), that is, the derivative can readily or easily be isolated and purified from a mixture containing such by-product(s) by adding an acid to the reaction products containing the by-product(s) and forming a salt of the object compound.

The isolation and purification can be carried out in an inert solvent. The solvent may not be critical as far as the 2-amino-1-phenylethanol derivative and the by-product can be dissolved therein and the salt of the 2-amino-1-phenylethanol derivative is insoluble therein, and includes organic solvent such as alcohols, ketones, aliphatic hydrocarbons, alicyclic hydrocarbons, aromatic hydrocarbons, ethers, esters and halogenated hydrocarbons as exemplified above. These solvents may be used singly or in combination.

The amount of the solvent is, usually, about 0.5 to 100 times by weight, preferably about 1 to 20 times by weight and more preferably about 5 to 15 times by weight relative to the total amount of the reaction products.

The formation of the salt of the 2-amino-1-phenylethanol derivative can be conducted by using any of an inorganic acid or an organic acid. As such method, there may be mentioned, for instance, (ia) a method adding an acid to the reaction products to obtain a salt of the 2-amino-1-phenylethanol derivative selectively by precipitating or crystallization the salt, or (ib) a method allowing not only the 2-amino-1-phenylethanol derivative but also other reaction product(s) having an amino group to form a salt, adding a base to the resultant mixture, making the impurity to be free or liberated by salt-exchange to obtain the salt of the 2-amino-1-phenylethanol derivative selectively.

Examples of the inorganic acid include hydrochloric acid, sulfuric acid, nitric acid, phosphoric acid, boric acid, carbonic acid and the like. Typical example of the inorganic acid include hydrochloric acid.

As the organic acid, there may be mentioned, for example, saturated aliphatic monocarboxylic acids such as formic acid, acetic acid, propionic acid, butyric acid, isobutyric acid, valeric acid, pivalic acid and O-benzoyl glycolic acid; saturated aliphatic dicarboxylic acids such as oxalic acid, malonic acid, succinic acid, glutaric acid, adipic acid, pimeric acid, suberic acid and others; unsaturated aliphatic carboxylic acids such as acrylic acid, propiolic acid, methacrylic acid, crotonic acid, isocrotonic acid, maleic acid, fumaric acid, citraconic acid, mesaconic acid, and so on; aliphatic hydroxycarboxylic acids such as glycolic acid, lactic acid, malic acid, tartaric acid, hydroxybutyric acid, hydroxyacrylic acid, glyceric acid, tartoronic acid, citric acid and others; carbocyclic carboxylic acids such as camphoric acid, benzoic acid, phthalic acid, isophthalic acid, terephthalic acid, naphthoic acid, o-chlorobenzoic acid, m-chlorobenzoic acid, p-chlorobenzoic acid, o-toluic acid, m-toluic acid, p-toluic acid, 2,5-dimethylbenzoic acid, 3,4-dimethylbenzoic acid, 3,5-dimethylbenzoic acid, 2,4,6-trimethylbenzoic acid, o-methoxybenzoic acid, m-methoxybenzoic acid, p-methoxybenzoic acid, o-aminobenzoic acid, m-aminobenzoic acid, p-aminobenzoic acid, vanilic acid, veratoric acid, cinnamic acid, 3,4-dihydroxycinnamic acid, 3,4-dimethoxycinnamic acid, benzilic acid, 3-phenylpropionic acid and the like; aromatic hydroxycarboxylic acids such as salicylic acid, m-hydroxybenzoic acid, p-hydroxybenzoic acid, gallic acid, tropic acid and so on; heterocyclic carboxylic acids such as nicotinic acid and isonicotinic acid; amino acids which may be protected on the amino group with a protective group (for example, glycine, N-(t-butoxycarbonyl)alanine and the like); sulfonic acids such as benzenesulfonic acid, p-toluenesulfonic acid, 2,5-dimethylbenzenesulfonic acid, 2,4,6-trimethylbenzenesulfonic acid, methanesulfonic acid and others.

Preferred examples of the organic acids include a $C_{1-3}$ saturated aliphatic monocarboxylic acid such as formic acid and acetic acid; a $C_{1-6}$ saturated aliphatic dicarboxylic acid such as oxalic acid and succinic acid; and a $C_{6-15}$ carbocyclic carboxylic acid such as benzoic acid and the like.

The amount of the acid may be selected from a wide range depending on the species of the acid, and is, for example, relative to 1 mole of the compound of the general formula (VI), about 1 gram equivalent or less, and preferably about 0.8 to 1 gram equivalent in case of the inorganic acid. When the amount of the acid is too small, the salt would not be formed sufficiently thus the yield is liable to decrease. On the other hand, when an excess amount of the acid is added, a by-product such as the position-isomer forms a salt and the purity tends to decrease. When utilizing an organic acid, probably because the solubility of a salt of the by-product(s) such as the position isomer formed with an organic acid is extremely high, while the solubility of a salt of the compound of the general formula (VI) formed with an organic acid is low, even when an excess amount of the organic acid is added, the organic acid salt of the compound of the general formula (VI) can selectively be precipitated or crystallized. The proportion of the acid in case of the organic acid is, usually about 0.8 gram equivalent or more (for example about 0.8 to 8 gram equivalents), preferably about 1 to 3 gram equivalents and more preferably about 1 to 2 gram equivalents relative to 1 mole of the compound of the formula (VI). The reaction temperature of the formation of the salt may, usually, be about 0° C. to 100° C., preferably about 10° to 80° C. and more preferably about 20° to 70° C. The reaction time is not critical and is, for example, about 10 minutes to 10 hours.

After formation of the salt, the salt of the 2-amino-1-phenylethanol derivative can be recovered from the reaction mixture by a conventional manner such as filtration. The temperature of filtration is, usually, about 0° to 50° C. and preferably about 10° to 30° C.

According to the method (ia), the salt of the 2-amino-1-phenylethanol derivative can selectively be precipitated since the basicity of the compound of the general formula (VI) is higher than the basicity of the by-products such as the position-isomer and dimer, and the solubility of the salt of the compound of the general formula (VI) is smaller relative to the solubility of the salts of the by-products. Thus, the 2-amino-1-phenylethanol derivative can efficiently be isolated and purified. In the salt of the 2-amino-1-phenylethanol derivative as obtained by such method, the content of impurities is generally about 2 weight % or less, and the salt of the 2-amino-1-phenylethanol derivative, can frequently be obtained in the yield of, for instance, about 90% or more.

As the method for isolation of the 2-amino-1-phenylethanol derivative, the method (ib) can also be employed which comprises forming corresponding salts to products having an amino group including the position-isomer, liberating impurities selectively by adding a base, and recovering the salt of the 2-amino-1-phenylethanol derivative of the general formula (VI).

In the method (ib), the salts of reaction products may be formed in the same manner as in the method (ia) except for the using amount of the acid. In the method (ib), the amount of the acid is, relative to 1 mole of the total amount of the 2-amino-1-phenylethanol derivative and the position-isomer thereof, about 1 gram equivalent or more and preferably about 1 to 3 gram equivalents. Addition of too little an amount of the acid tends to make the yield decreased, and addition of too much of an amount of the acid would be liable to make the cost high and reduce economic properties.

When recovering the produced salts in a conventional method such as filtration after forming the salts, impurities other than the position-isomer would be removed and the obtained salts are frequently a mixture of the salt of the object compound and the salt of the position-isomer thereof. The ratio of the position-isomer and the compound of the general formula (VI) may be the same as the ratio before formation of the salts.

In this method (ib), the isolation or purification may be conducted by using the higher basicity of the compound of the general formula (VI) relative to the basicity of the corresponding position-isomer. That is, the salt of the 2-amino-1-phenylethanol derivative of the general formula (VI) is selectively recovered by allowing a base to act on the salts obtained by the procedure mentioned above to liberate or set free the position-isomer selectively. More practically, the position isomer can selectively be liberated by, for example, dispersing the salts to a solvent, and adding a base to the dispersion. As the solvent used for dispersing the salts, any solvents having poor solubility for the salts and having good solubility for the free form of the position-isomer can be used, and for example, the solvents as exemplified above can be employed.

The base includes inorganic bases and organic bases. Examples of the inorganic bases include alkali metal hydroxides such as sodium hydroxide, potassium hydroxide and lithium hydroxide; alkaline earth metal hydroxides such as magnesium hydroxide, calcium hydroxide and barium hydroxide; alkali metal carbonates such as sodium carbonate, potassium carbonate and lithium carbonate; alkaline earth metal carbonate such as magnesium carbonate, calcium carbonate and barium carbonate; alkali metal hydrogencarbonates such as sodium hydrogencarbonate and potassium hydrogencarbonate. The organic bases include, for example, metal alkoxides such as alkali metal alkoxides (for example, a sodium or potassium $C_{1-4}$ alkoxide such as sodium methoxide, sodium ethoxide, sodium propoxide, sodium butoxide, potassium methoxide, potassium ethoxide, potassium propoxide and potassium butoxide, etc.); primary amines such as an aliphatic primary amine including a monoalkylamine (e.g. a $C_{1-8}$ alkylamine such as methylamine, ethylamine, propylamine, butylamine, etc.) and an aromatic primary amine (e.g. aniline, toluidine, benzylamine, naphthylamine etc.); secondary amines such as an dialkylamine (e.g. a di-$C_{1-8}$ alkylamine such as dimethylamine, diethylamine, dipropylamine, diisopropylamine, dibutylamine, diisobutylamine, di-s-butylamine, di-t-butylamine, etc.), an aromatic secondary amine (for example, N-methylaniline, N-ethylaniline, dibenzylaniline, diphenylamine and the like), and cyclic amines such as pipecoline, piperidine, morpholine, pyrrolidine, etc.; tertiary amines such as a trialkylamine (e.g. a tri-$C_{1-8}$ alkylamine such as trimethylamine, triethylamine, tripropylamine, tributylamine, etc.), N,N-di-substituted alkanolamines such as N,N-di-$C_{1-4}$ alkyl alkanolamine (e.g. N,N-dimethylethanolamine and the like), N,N-dimethylaniline, N,N-diethylaniline, 4-dimethylaminopyridine, triphenylamine, tribenzylamine, N-methylmorpholine, N-methylpiperidine and others; basic nitrogen-containing heterocyclic compounds such as pyridine, picoline, quinoline, and others. These bases can be employed singly or in combination.

Preferred examples of the base include organic bases, specifically amines. Typically, bases having an electrolytic dissociation exponent pKa value (hereinafter briefly referred to as pKa value) between the pKa value of the 2-amino-1-phenylethanol derivative and the pKa value of the impurities such as the position-isomer thereof can advantageously be used as the base. By using such a base, the impurities can selectively be liberated. Preferred examples of the base include a base having a pKa value of about 9.3 to 11.5, for example, a $C_{1-8}$ alkylamine such as ethylamine (pKa=10.8); a di-$C_{1-8}$ alkylamine such as diethylamine (pKa=10.4); a tri-$C_{1-8}$ alkylamine such as triethylamine (pKa=11.0); and a cyclic amine such as piperidine (pKa=11.1). Practically preferred base includes, for instance, a base having a pKa value of about 10 to 11.3 and more preferably about 10.5 to 11.2.

The amount of the base is not critical as far as being 1 gram equivalent or more relative to 1 mole of the position-isomer, and is generally about 0.1 to 1.0 gram equivalent and preferably about 0.3 to 0.6 gram equivalent relative to 1 mole of the total amount of the salt of 2-amino-1-phenylethanol derivative and the salt of the position-isomer. When the amount of the base is exceedingly small, removal of the position-isomer is liable to be insufficient, and when the amount is too much, the economic availabilities tends to decrease. The reaction time and temperature may be selected from the same range as mentioned in the formation of the salt.

By adding such base, the salt of the position-isomer would be salt-exchanged with the base to be liberated, thus the 2-amino-1-phenylethanol derivative remains in the form of salt. The salt of the 2-amino-1-phenylethanol derivative can be readily isolated by conducting, for example, filtration as mentioned above. The salt of the derivative thus obtained has high purity and the content of impurities such as a by-product is usually about 2% or less. The product may occasionally contain a salt formed with the base which is salt-exchanged and the acid used for the salt formation, and in such a case, the salt can easily be removed in the liberation. Further, after adding the acid, the base may be added without isolating the salt.

The isolation (purification) of the object 2-amino-1-phenylethanol derivative can also be carried out by changing the order of the addition of the salt and the addition of the base, that is the salt of the 2-amino-1-phenylethanol derivative may be formed by, after adding the base, adding the acid to the reaction products. In such a method, the amount of the acid which is added is generally about 0.8 to 2.0 gram equivalents and preferably about 1.0 to 1.5 gram equivalents relative to 1 mole of the compound of the general formula (VI). Addition of the acid in a proportion of less than 0.8 gram equivalent tends to make the yield decreased and addition of the acid in an amount of exceeding 2.0 gram equivalents would make the removal of impurities insufficient and the purity is liable to lessen. The acid may frequently be added in an amount of 1 gram equivalent or more relative to 1 mole of the total amount of the compound of the general formula (VI) and the position-isomer thereof.

According to the above-mentioned methods, the salt of the 2-amino-1-phenylethanol derivative of the general formula (VI) can selectively be isolated and purified by removing the position-isomer of the object compound or other by-products from the reaction products.

The 2-amino-1-phenylethanol derivative having high purity can be obtained by liberating the salt of the 2-amino-1-phenylethanol derivative thus obtained in a conventional manner. The liberation can be carried out by allowing the salt of the 2-amino-1-phenylethanol derivative to react with a base, for example by dissolving or dispersing the salt in water or an organic solvent, adding a base as, for example, an aqueous solution to resultant mixture, and after liberating the compound, extracting the resulting free compound with an organic solvent, and when necessary washing the extract with water, and removing off the solvent.

As the organic solvent, hydrophobic organic solvents such as aliphatic hydrocarbons, aromatic hydrocarbons, halogenated hydrocarbons, ethers, esters can be employed as mentioned above. These solvents can be used singly or in combination. Among such solvents, halogenated hydrocarbons and esters can advantageously be employed. The proportion of the solvent in the extraction of liberated 2-amino-1-phenylethanol derivative is, relative to the total amount of the salt, about 0.5 to 40 times by weight and preferably about 1 to 20 times by weight.

Examples of the base include inorganic bases including alkali metal hydroxides such as sodium hydroxide, potassium hydroxide and lithium hydroxide; alkali metal carbonates such as sodium carbonate, potassium carbonate and lithium carbonate; alkali metal hydrogencarbonates such as sodium hydrogencarbonate, potassium hydrogencarbonate and lithium hydrogencarbonate; alkaline earth metal hydroxides such as magnesium hydroxide. The amount of the base is, usually, about 0.8 to 10 gram equivalents and preferably about 1 to 8 gram equivalents relative to 1 mole of total amount of the salt. The using amount of the water in the extraction of liberated 2-amino-1-phenylethanol derivative is, relative to the total amount of the salt, for example, about 1 to 50 times by weight and preferably about 5 to 20 times by weight.

The compound of the general formula (VI) can easily be converted to the 2-amino-1-phenylethanol derivative of the general formula (I) by cleaving the protective group for hydroxyl group in a conventional manner, and be supplied to, for example, the following production of the optically active compound with the aid of a microorganism.

The microorganism to be employed in accordance with the method (A) may be any strain of microorganism that is capable of acting on a mixture of the enantiomers of the 2-amino-1-phenylethanol derivative of the general formula (I) or a salt thereof to produce the (R)-2-amino-1-phenylethanol compound of the general formula (IIa) or a salt thereof. Such microorganisms include, for example, microorganisms which selectively utilize the (S)-form among the both enantiomers of the 2-amino-1-phenylethanol derivative, and microorganisms which selectively convert the (S)-form to another compound including the (R)-form.

Examples of the microorganisms having such capability include a strain of microorganisms belonging to the genus Hansenula, the genus Geotrichum, the genus Candida, the genus Cryptococcus, the genus Rhodosporidium, the genus Rhodotorula, the genus Saccharomyces, the genus Sporobolomyces, the genus Kluyveromyces, the genus Issatchenkia, the genus Pichia, the genus Botryoascus, the genus Debaryomyces, the genus Lipomyces, the genus Metschnikowia, the genus Saccharomycodes, the genus Schizoblastosporion, the genus Stephanoascus, the genus Sterigmatomyces, the genus Zygosaccharomyces, the genus Sporidiobolus, the genus Malassezia, the genus Torulaspora, the genus Corynebacterium, the genus Gluconobacter, the genus Promicromonospora, the genus Pseudomonas, the genus Bordetella, the genus Acetobacter, the genus Bacillus, the genus Agrobacterium, the genus Arthrobacter, the genus Amauroascus, the genus Brevibacterium, the genus Micrococcus, the genus Aureobacterium, the genus Azotobacter, the genus Xanthomonas, the genus Klebsiella, the genus Comamonas, the genus Mycobacterium, the genus Terrabacter, the genus Agrocybe, the genus Trichoderma, the genus Alternaria, the genus Hamigera, the genus Moniliella, the genus Pholiota, the genus Podospola, the genus Aegerita, the genus Streptomyces, the genus Saccharomycopsis, the genus Leucosporidium, *Rhodococcus amidophilus* (IFM 0144) *Rhodococcus equi* and others.

Practical examples of the microorganisms capable of acting on a mixture of the enantiomers of the 2-amino-1-phenylethanol derivative of the general formula (I) to produce the corresponding (R)-2-amino-1-phenylethanol derivative include strains of microorganisms as mentioned below:

(1) the genus Hansenula: *Hansenula anomala* IFO 0707, etc., (2) the genus Geotrichum: *Geotrichum candidum* IFO 4601, *Geotrichum candidum* IFO 4598, etc., (3) the genus Candida: *Candida albicans* IFO 1594, *Candida albicans* IFO 1856, *Candida parapsilosis* IFO 1022, *Candida gropengiesseri* IFO 0659, *Candida aaseri* IFO 10404, *Candida beechii* IFO 10229, *Candida atmospherica* IFO 1969, *Candida natalensis* IFO 1981, *Candida paludigena* IFO 10330, *Candida sake* IFO 1149, *Candida pintolopesii* var. *pintolopesii* IFO 0729, etc., (4) the genus Cryptococcus: *Cryptococcus neoformans* IAM 4788, etc., (5) the genus Rhodosporidium: *Rhodosporidium sphaerocarpum* IFO 1438, *Rhodosporidium diobovatum* IFO 0688, etc., (6) the genus Rhodotorula: *Rhodotorula rubra* IFO 0406, *Rhodotorula rubra* AHU 3948, *Rhodotorula glutinis* var. *dairenensis* IFO 0415, etc., (7) the genus Saccharomyces: *Saccharomyces montanus* IFO 0021, etc., (8) the genus Sporobolomyces: *Sporobolomyces roseus* IFO 1040, etc., (9) the genus Kluyveromyces: *Kluyveromyces marxianus* var. *bulgaricus* IAM 4829, *Kluyveromyces lactis* IFO 1267, etc.,

(10) the genus Issatchenkia: *Issatchenkia scutulata* var. *scutulata* IFO 10069, *Issatchenkia scutulata* var. *scutulata* IFO 10070, etc.,

(11) the genus Pichia: *Pichia thermotolerans* IFO 10024, *Pichia farinosa* IFO 1163, etc.,

(12) the genus Botryoascus: *Botryoascus synnaedendrus* IFO 1604, etc.,

(13) the genus Debaryomyces: *Debaryomyces hansenii* var. *hansenii* IFO 0083, etc.,

(14) the genus Lipomyces: *Lipomyces starkeyi* IFO 1289, etc.,

(15) the genus Metschnikowia: *Metschnikowia bicuspidata* IFO 1408, etc.,

(16) the genus Saccharomycodes: *Saccharomycodes ludwigii* IFO 0798, etc.,

(17) the genus Schizoblastosporion: *Schizoblastosporion kobayashii* IFO 1644, etc.,

(18) the genus Stephanoascus: *Stephanoascus ciferrii* IFO 1854, etc.,

(19) the genus Sterigmatomyces: *Sterigmatomyces halophilus* IFO 1488, etc.,

(20) the genus Zygosaccharomyces: *Zygosaccharomyces rouxii* IFO 0510, *Zygosaccharomyces rouxii* IAM 4114, *Zygosaccharomyces fermentati* IFO 0021, etc.,

(21) the genus Sporidiobolus: *Sporidiobolus salmonicolor* IFO 1845, *Sporidiobolus pararoseus* IFO 1107, etc.,

(22) the genus Malassezia: *Malassezia furfur* IFO 0656, etc.,

(23) the genus Torulaspora: *Torulaspora delbrueckii* IFO 0955, etc.,

(24) the genus Corynebacterium: *Corynebacterium aquaticum* IFO 12154, *Corynebacterium mediolanum* JCM 3346, etc.,

(25) the genus Gluconobacter: *Gluconobacter asaii* IFO 3265, *Gluconobacter oxydans* IFO 3255, *Gluconobacter oxydans* IFO 3130, *Gluconobacter oxydans* IFO 3289, *Gluconobacter frateurii* IFO 3271, etc.,

(26) the genus Promicromonospora: *Promicromonospora citrea* IFO 12397, etc.,

(27) the genus Pseudomonas: *Pseudomonas aeruginosa* IFO 3899, *Pseudomonas riboflavina* IFO 13584, *Pseudomonas fluorescens* IFO 3925, *Pseudomonas putida* IFO 12996, *Pseudomonas syncyanea* IFO 3757, *Pseudomonas diminuta* IFO 12697, *Pseudomonas chlororaphis* IFO 3522, *Pseudomonas fragi* IFO 3458, *Pseudomonas sp.* ATCC 14676, etc.,

(28) the genus Bordetella: *Bordetella bronchiseptica* IFO 13691, etc.,

(29) the genus Acetobacter: Acetobacter sp. IFO 3248, Acetobacter sp. IFO 3297, *Acetobacter pasteurianus* ATCC 10245, *Acetobacter pasteurianus* IFO 3259, *Acetobacter pasteurianus* IFO 3277, etc.,

(30) the genus Bacillus: *Bacillus subtilis* IFO 3013, *Bacillus subtilis* IFO 3009, *Bacillus cereus* AHU 1355, *Bacillus cereus* AHU 1707, *Bacillus cereus* IFO 3001, *Bacillus coagulans* IAM 1115, *Bacillus brevis* IFO 3331, *Bacillus sphaericus* IFO 3525, etc.,

(31) the genus Agrobacterium: *Agrobacterium radiobacter* IFO 12664, etc.,

(32) the genus Arthrobacter: *Arthrobacter ureafaciens* IFO 12140, etc.,

(33) the genus Amauroascus: *Amauroascus reticulatus* IFO 9196, etc.,

(34) the genus Brevibacterium: *Brevibacterium linens* IFO 12141, etc.,

(35) the genus Micrococcus: *Micrococcus roseus* IFO 3764, etc.,

(36) the genus Aureobacterium: *Aureobacterium testaceum* IFO 12675, etc.,

(37) the genus Azotobacter: *Azotobacter vinelandii* IFO 13581, etc.,

(38) the genus Xanthomonas: *Xanthomonas campestris* pv *oryzae* IAM 1657, etc.,

(39) the genus Klebsiella: *Klebsiella pneumoniae* IFO 3317, etc.,

(40) the genus Comamonas: *Comamonas testosteroni* IFO 12048, *Comamonas testosteroni* IAM 1048, etc.,

(41) the genus Mycobacterium: *Mycobacterium diernhoferi* IFO 3707, etc.,

(42) the genus Terrabacter: *Terrabacter tumescens* IFO 12960, etc.,

(43) the genus Agrocybe: *Agrocybe cylindracea* IFO 30299, etc.,

(44) the genus Trichoderma: *Trichoderma viride* IFO 5720, etc.,

(45) the genus Alternaria: *Alternaria kikuchiana* IFO 5778, etc.,

(46) the genus Hamigera: *Hamigera avellanea* IFO 7721, etc.,

(47) the genus Moniliella: *Moniliella acetoabutans* IFO 9481, etc.,

(48) the genus Pholiota: *Pholiota nameko* IFO 6141, etc.,

(49) the genus Podospola: *Podospola carbonaria* IFO 30294, etc.,

(50) the genus Aegerita: *Aegerita candida* IFO 6988, etc.,

(51) the genus Streptomyces: *Streptomyces cinereoruber* HUT 6142, etc.,

(52) the genus Saccharomycopsis: *Saccharomycopsis capsularis* IFO 0672, etc.,

(53) the genus Leucosporidium: *Leucosporidium scottii* IFO 1923, *Leucosporidium scottii* IFO 1924, etc.,

(54) *Rhodococcus amidophilis*: *Rhodococcus amidophilus* (IFM 0144), etc.,

(55) *Rhodococcus equi*: *Rhodococcus equi* JCM 1313, etc.

At least one of these microorganisms may be used. By permitting the microorganism or a preparation thereof acting on a mixture of the enantiomers of the 2-amino-1-phenylethanol derivative of the general formula (I), the ratio of the (R)-form among the both enantiomers would be increased.

The microorganisms identified hereinabove by IFO numbers are described in the "List of Cultures, Ed. 9 (1992)" published by Institute for Fermentation, Osaka (IFO), Japan and are available from the same Institute. The microorganisms designated by JCM numbers are listed in "Catalogs of Microbial Strains, Ed. 5 (1992)" published by the Culture Collection of The Institute of Physical and Chemical Research, Japan and available from the same Culture Collection. The microorganisms identified by ATCC numbers are listed in "Catalogue of Bacteria and Bacteria Phages, Ed. 18 (1992)", "Catalogue of Yeasts, Ed. 18(1990)" and "Catalogue of Filamentous Fungi, Ed. 18 (1990)" each published by the American Type Culture Collection (ATCC) and are respectively available from the same organization. The microorganism designated by DSM numbers are listed in "Catalogue of strains (1989)" published by the German Collection of Microorganisms and Cell Cultures (DSM) and are available from the same organization. The microorganisms titled by IAM numbers are listed in "Catalogue of Strains" published by the Cell & Functional Polymer General Center, Institute of Molecular Cell Biology of Tokyo University, Japan, and are available by the same institute. The microorganisms designated by BGSC numbers are listed in "Strains and Data" published by the Bacillus Genetic Stock Center (BGSC), and are available from the same stock center. The microorganisms identified by AHU numbers are listed in "Catalogue of Cultures, Ed. 5 (1992)" published by the Japan Federation of Cell Collection, and are available from Faculty of Agriculture, Hokkaido University, Japan. The microorganisms titled by IFM numbers and HUT numbers are respectively available from Chiba University, Japan and Hiroshima University, Japan.

For the purposes of the invention, any of the wild strains, mutants and recombinant strains which can be obtained by a genetic engineering technique such as cell fusion or gene manipulation can suitably be used, as far as having the ability or capability of acting on a mixture of the enantiomers of the 2-amino-1-phenylethanol derivative of the general formula (I) to produce the corresponding (R)-form.

A microorganism such as above is, usually, grown in a culture medium and submitted to the reaction with a mixture of enantiomers of the compound of the general formula (I).

The medium used for growing the strain for use in the invention is not critical in composition only if the selected strain may grow and multiply therein. The medium may frequently be a fluid medium containing sources of carbon and nitrogen and other nutrients. Any carbon source which the strain can utilize may be employed. As the sources of carbon, there may be employed, for example, various carbohydrates or saccharides such as glucose, fructose, sucrose, dextrin, starch, etc.; alcohols such as sorbitol, methanol, ethanol, glycerol, etc.; organic acids such as fumaric acid, citric acid, acetic acid, propionic acid, etc. and the corresponding salts; hydrocarbons such as paraffin; and various mixtures thereof. The sources of nitrogen include, for instance, inorganic acid ammonium salts such as ammonium chloride, ammonium sulfate, ammonium phosphate, etc.; organic acid ammonium salts such as ammonium fumarate, ammonium citrate, etc.; inorganic or organic nitrogen-containing materials such as meat extract, yeast extract, malt extract, peptone (polypeptone), corn steep liquor, casein hydrolysate, urea, etc.; and various mixtures thereof.

In the medium, there may be incorporated appropriate amounts of those nutrients which are commonly employed in the cultivation of microorganisms, such as inorganic salts, trace metal salts and vitamins. Where necessary, there may also be incorporated factors which may promote growth of the strain used and/or factors which may augment its ability to produce the object compound of the invention, for example, the 2-amino-1-phenylethanol derivative of the general formula (I), as well as a buffer substance which may assist in the maintenance of the medium at a given pH.

The cultivation of the microorganism is carried out under conditions optimal for the growth of the particular strain, for example at a medium pH in the range of about 2.0 to 9.5, preferably about 3 to 8, and an incubation temperature in the range of about 20° to 45° C., preferably about 25° to 37° C. The cultivation may be aerobic or anaerobic. The cultivation time is, for example, about 5 to 120 hours, preferably about 12 to 72 hours.

The proportions of the (R)-form and the (S)-form in the substrate mixture of enantiomers of the 2-amino-1-phenylethanol derivative shown by the general formula (I) are not critical, but it is advantageous for commercial purposes to employ a racemic form of the 2-amino-1-phenylethanol derivative.

The method of asymmetric utilization is not critical so far as the function of a microorganism or a preparation thereof to act on the 2-amino-1-phenylethanol derivative of the general formula (I) to produce the (R)-2-amino-1-phenylethanol derivative of the general formula (IIa), and may, for example, be whichever of the following alternatives: (1) a technique adding a mixture of enantiomers of the 2-amino-1-phenylethanol derivative to the culture medium where the microorganism is cultivated, (2) a technique which comprises separating the microbial cells from the culture broth, e.g. by centrifugation, resuspending the cells, either as they are or after washing, in a buffer solution, water or the like, and adding a mixture of enantiomers of the 2-amino-1-phenylethanol derivative to the resulting cell suspension to treat the mixture therewith, (3) a technique which comprises permitting a treated preparation of cells such as disrupted cells, acetone-treated cells, lyophilized cells, instead of viable cells as such, to react with a mixture of enantiomers of the 2-amino-1-phenylethanol derivative, (4) a technique which comprises immobilizing the cells or preparation thereof can be employed as immobilized by known techniques such as the polyacrylamide gel method, sulfurcontaining polysaccharide gel method (e.g. carrageenin gel method), alginic acid gel method, agar gel method and so on, and permitting the cells or a preparation thereof to act on a mixture of enantiomers of the 2-amino-1-phenylethanol derivative. The enzyme purified from such a cell preparation can also be used. The enzyme can be obtained with the use of known purification processes in a suitable combination.

There are cases in which this reaction proceeds with advantage of a higher yield of the objective optically active compound in the presence of a carbon source such as glucose, sucrose, ethanol, methanol or paraffin; phosphoric acid; or a nitrogen source such as yeast extract or corn steep liquor which serve as an energy source.

A mixture of enantiomers of the 2-amino-1-phenylethanol derivative can be used as it is or in the form of a solution, suspension or dispersion containing a suitable solvent. As the solvent, water or an organic solvent which will not interfere with the reaction can be employed. A suspension or a dispersion prepared with a surfactant can also be used when necessary. The mixture of enantiomers of the 2-amino-1-phenylethanol derivative may be added in bolus at the beginning of the reaction or in several installments.

The optimal cell concentration of the reaction system can be selected from the range where the yield and the optical purity of the desired optically active compound will not be adversely affected. A typical cell concentration may for example be, on a dry cell basis, about 0.1 to 500 g/liter and preferably about 1 to 300 g/liter. The concentration of the substance mixture of enantiomers of the 2-amino-1-phenylethanol derivative is not particularly restricted and is, for example, about 0.01 to 20% by weight and preferably about 0.1 to 10% by weight.

The reaction conditions of the asymmetric utilization can be selected from the ranges that will not detract from the yield of the object compound. For example, the pH of the reaction system can be selected from the range of pH about 2 to 10 and preferably pH about 3 to 8. The reaction temperature is selected from the range of, for example, about 10° to 60° C. and preferably from about 20° to 40° C. and more preferably from about 20° to 35° C. The reaction can be conducted with stirring or under stationary conditions for about 1 to 120 hours. As a tendency, the longer the reaction time, the higher is the optical purity of the (R)-2-amino-1-phenylethanol derivative.

Thus, when permitting the specific microorganism or a preparation thereof to act on a mixture of enantiomers of the 2-amino-1-phenylethanol derivative, the asymmetric utilization can proceed smoothly or advantageously to produce the corresponding 2-amino-1-phenylethanol derivative having an (R)-configuration with a high selectivity.

The (R)-2-amino-1-phenylethanol derivative of the general formula (IIa) produced by the reaction can be recovered or harvested by the separation and purification procedures generally known. For example, the (R)-2-amino-1-phenylethanol derivative having a high optical purity can be easily obtained by subjecting the reaction mixture, directly or after separation of the cells, to the conventional purification procedure such as membrane separation, extraction with an organic solvent (for example, hexane, chloroform, ethyl acetate and the like), column chromatography, vacuum concentration, distillation, crystallization and recrystallization. The optical purity of the (R)-2-amino-1-phenylethanol derivative can be measured by, for instance, high performance liquid chromatography (HPLC) using an optical resolution column.

The method (B) where the compound of the general formula (IIa) is obtained from the compound of the general formula (VII) (aminoketone compound) with the aid of a microorganism is explained hereinbelow.

In the method (B), the compound of the general formula (IIa) or a salt thereof can easily or readily be obtained by permitting a microorganism or a preparation thereof to act on the compound of the general formula (VII) or a salt thereof (aminoketone derivative) to asymmetrically reduce and harvesting or recovering the produced (R)-2-amino-1-phenylethanol derivative.

As examples of the aminoketone derivative of the general formula (VII) used as a raw material, there may be mentioned aminoketone derivatives corresponding to the compounds as mentioned as practical examples of the (R)-2-amino-1-phenylethanol derivative of the general formula (II).

The aminoketone derivative can be used as a free amine-form but a salt with an inorganic acid or an organic acid may also be employed. The inorganic acid includes, for example, hydrochloric acid, sulfuric acid, phosphoric acid and so on. As the organic acid, for instance, the aliphatic monocarboxylic acids and aliphatic polycarboxylic acids and the like exemplified in the explanation of the isolation and purification of the 2-amino-1-phenylethanol derivative may be employed.

The compound of the general formula (VII) can be prepared by a known method, for example, by allowing the compound shown by the general formula (XVIII)

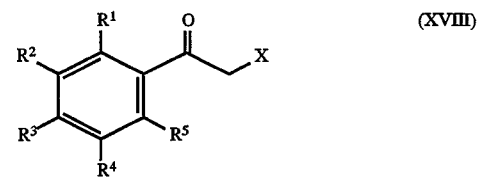

wherein $R^1$, $R^2$, $R^3$, $R^4$, $R^5$ have the same meanings as defined above, and X represents a halogen atom to react with an aminating agent. As the aminating agent, there may be employed hexamethylenetetramine and others, as well as the aminating agents as exemplified above. Examples of the halogen atom shown by X include fluorine atom, chlorine atom, bromine atom and iodine atom.

Any strain of microorganism can be used for the process, as far as being capable of acting on the aminoketone derivative of the general formula (VII) to produce the corresponding (R)-2-amino-1-phenylethanol derivative of the general formula (IIa).

Such microorganisms having the capability include, for instance, a strain of microorganism belonging to the genus Candida, the genus Lodderomyces, the genus Catenuloplanes, the genus Pilimelia, the genus Saccharothrix, the genus Seratia, the genus Enterococcus, the genus Lactobacillus, the genus Pediococcus and the genus Lactococcus.

Typical examples of the microorganism that is capable of acting on the aminoketone compound to produce the corresponding (R)-2-amino-1-phenylethanol derivative include following strains of microorganisms:

(56) the genus Candida: *Candida maltosa* IFO 1977, *Candida maltosa* IFO 1978, etc.,

(57) the genus Lodderomyces: *Lodderomyces elongisporus* IFO 1676, etc.,

(58) the genus Catenuloplanes: *Catenuloplanes japonicus* IFO 14176, etc.,

(59) the genus Pilimelia: *Pilimelia terevasa* IFO 14556, etc.,

(60) the genus Saccharothrix: *Saccharothrix australiensis* IFO 14444, etc.,

(61) the genus Seratia: *Seratia marcescens* IFO 3735, etc.,

(62) the genus Enterococcus: *Enterococcus faecalis* IFO 12964, etc.,

(63) the genus Lactobacillus: *Lactobacillus casei* subsp. *casei* NRIC 1042, etc.,

(64) the genus Pediococcus: *Pediococcus acidilactici* NRIC 1089, etc.,

(65) the genus Lactococcus: *Lactococcus lactis* subsp. *lactis* AHU 1089, etc.

At least one of these microorganisms can be employed. For the purposes of the invention, any of wild strains, mutants and recombinant strains which can be obtained by a genetic engineering technique such as cell fusion or gene manipulation can suitably be used, as far as having the above mentioned ability or capability.

The microorganisms identified hereinabove by IFO numbers and AHU number can be available from the organizations. The strain of microorganism designated by NRIC number is listed in "Catalogue of Microbial Strains 2nd Ed. (1992)" published by the Laboratory of Microbial Strain Collection, Tokyo Agriculture University, Japan and is available from the institution.

The cultivation, reaction, and recovery of the product can be carried out in the similar manner as in the method (A) using a mixture of enantiomers of the 2-amino-1-phenylethanol derivative of the general formula (I).

The methods (C) and (D) are illustrated and explained hereinbelow.

The method (C) can readily or easily be carried out by utilizing the optically active enantiomer of (R)-form respectively as the compound of the formula (III) or compound of the formula (IV) used as a reactant when isolating and purifying the 2-amino-1-phenylethanol derivative as a precipitated salt from the reaction products obtained in the aminating methods (b), (c) in the method (A).

The (R)-2-amino-1-phenylethanol derivative having high optical purity can be obtained in an expedient procedure with high yield according to this method.

The method (D) can readily be conducted, when isolating and purifying the 2-amino-1-phenylethanol derivative as a precipitated salt from the reaction products obtained in the aminating methods (b), (c) in the method (A), by utilizing an acid capable of optically resolving, for instance, an optically active organic acid, as the acid used for the formation of the salt. When using the optically active organic acid, not only the object compound can be isolated from the by-products such as the position-isomer and dimer but also the (S)-form and the (R)-form of the 2-amino-1-phenylethanol derivative can easily be isolated since the acid acts as an optically resoluting agent and a diastereomer salt is formed by the acid.

Examples of the optically active organic acid include aliphatic hydroxycarboxylic acids such as D-lactic acid, L-lactic acid, D-malic acid, L-malic acid, D-tartaric acid, L-tartaric acid, D-di-p-toluoyltartaric acid, L-di-p-toluoyltartaric acid, and the like; carbocyclic carboxylic acids such as (R)-2-phenylpropionic acid, (S)-ibuprofen, (R)-2-(2,5-dimethylphenyl)propionic acid, (S)-2-(2,5-dimethylphenyl)propionic acid, (R)-(−)-2-(2,4,6-trimethylphenyl)propionic acid, (S)-(+)-2-(2,4,6-trimethylphenyl)propionic acid and so on; aromatic hydroxycarboxylic acids such as D-mandelic acid, L-mandelic acid, etc.; sulfonic acids such as D-camphorsulfonic acid, L-camphorsulfonic acid, and the like; and optically active D- or L-amino acids which may be protected with a protective group on the amino group.

The amino acid includes, for example, amino acids having a non-polar group in the side chain such as non-polar amino acids including aliphatic non-polar amino acids such as alanine, valine, leucine, isoleucine, methionine and proline, aromatic non-polar amino acids such as tryptophan, phenylalanine and anthranic acid; amino acids having a polar group in the side chain including polar amino acids having no charge such as serine, threonine, cysteine tyrosine, asparagine and glutamine, polar amino acids having plus-charge such as lysine, histidine and arginine, polar amino acids having minus-charge such as aspartic acid and glutamic acid.

Examples of the protective group for amino group include an optionally substituted $C_{1-6}$ acyl group (e.g. formyl, acetyl group, etc.), an optionally substituted $C_{7-16}$ acyl group having an aromatic ring such as benzoyl and phthaloyl groups, an optionally substituted $C_{1-4}$ alkoxy-carbonyl group (for instance t-butoxycarbonyl group), an optionally substituted $C_{6-16}$ aryloxy-carbonyl group, an optionally substituted $C_{7-20}$ aralkyloxy-carbonyl group (for example benzyloxycarbonyl, p-nitrobenzyloxycarbonyl group, etc.), an optionally substituted $C_{7-20}$ aralkyl group such as benzyl and triphenylmethyl, and others. Practical examples of the protective group for the amino group include an optionally substituted $C_{1-4}$ alkoxy-carbonyl group such as t-butoxycarbonyl, and an optionally substituted $C_{7-20}$ aralkyloxy-carbonyl group such as benzyloxycarbonyl group.

The functional group in the side chain of the amino acid, for instance, a hydroxyl group, a mercapto group, a carboxyl group, or an amino group may be protected with a conventional protective group such as those exemplified above.

The (R)-2-amino-1-phenylethanol derivative can efficiently be obtained by selecting and using a suitable optical resoluting agent among these agents depending on the species of the object (R)-2-amino-1-phenylethanol derivative.

As preferred examples of the optically active organic acid, there may be mentioned optically active aliphatic or aromatic hydroxycarboxylic acids which may be protected with a protective group on the hydroxyl group, optically active amino acids which may be protected with a protective group on the amino group. Among these optically active hydroxy carboxylic acids, an optically active tartaric acid which may be protected with a protective group on the hydroxyl group such as D- (or L-) tartaric acid and D-(or L-)di-p-toluoyl tartaric acid can be preferably employed. As the optically active amino acid, preferred is an optically active aliphatic non-polar amino acid which may be protected with a protective group on the amino group such as N-(t-butoxycarbonyl)-L-(or D-)alanine, as well as an optically active amino acid having a polar group in the side chain such as polar non-charge amino acid which may be protected with a protective group on the amino group and/or on the functional group of the side chain such as N-(t-butoxycarbonyl) -O-benzyl-L-(or D-)threonine, N-(t-butoxycarbonyl)-S-benzyl-L (or D)-cysteine, N-(t-butoxycarbonyl)-L (or D)-tyrosine and others.

Formation and isolation of the salt can be conducted in the similar manner to those in the formation of the acid by using an organic acid in the method (A).

According to the method (D), the (R)-2-amino-1-phenylethanol derivative having an extremely high purity, for example, the content of the impurity is about 2% or less, and the optical purity of about 99% ee or more, can efficiently be obtained.

The compound of the general formula (IIa) can readily or easily be converted to the compound of the general formula (II) by, if necessary, introducing a suitable protective group to the hydroxyl group. Such compound of the general formula (II) is useful for the production of the (R,R)-1-phenyl-2-[(2-phenyl-1-alkylethyl)amino]ethanol derivative.

The process of producing the (R,R)-1-phenyl-2-[(2-phenyl-1-alkylethyl)amino]ethanol derivative of the general formula (XI) is illustrated hereinbelow.

In $R^7$ and $R^8$ of the general formula (XI), as the optionally substituted lower alkyl group, the carboxyl group which may be protected with a protective group, the optionally substituted lower alkoxycarbonyl group, the optionally substituted amino group, the optionally substituted alkylsulfonyl group and the optionally substituted arylsulfonyl group, there may be employed the optionally substituted lower alkyl group and the like as mentioned in the explanation of $R^1$ to $R^5$.

The optionally substituted aryl group, the optionally substituted aralkyl group and the optionally substituted acyl group in $R^7$ and $R^8$ include, for instance, an optionally substituted $C_{6-16}$ aryl group and an optionally substituted $C_{7-20}$ aralkyl group and an optionally substituted acyl group as exemplified in the explanation of the protective group for hydroxyl group.

As examples of the optionally substituted cycloalkyl group, there may be mentioned a $C_{3-10}$ cycloalkyl group (e.g. cyclopropyl, cyclobutyl, cyclopentyl, cyclohexyl, cycloheptyl, cyclooctyl, cyclononyl or cyclodecyl group) which may be substituted with a substituents such as a $C_{1-4}$ alkyl group, a hydroxyl group, a halogen atom and so on.

The protective group for hydroxyl group in $R^7$ and $R^8$ includes, for example, protective groups for hydroxyl group generally used in the field of organic synthesis such as the protective groups for hydroxyl group (A) to (D) exemplified in $R^1$ to $R^5$.

When $R^7$ and $R^8$ are respectively the group (IX): —O—$R^{7a}$ and the group (X): —O—$R^{8a}$, and $R^{7a}$ and $R^{8a}$ form a ring together with the adjacent oxygen atoms, the ring may for example be a 5- to 10-membered ring, preferably a 5- to 8-membered ring and more preferably a 5- or 6-membered ring. Such $R^{7a}$ and $R^{8a}$ includes, for instance, an optionally substituted alkylene group, a carbonyl group, a thiocarbonyl group and others.

As the alkylene group, there may be mentioned, for instance, an alkylene group having 1 to 4 carbon atoms such as methylene, ethylene, trimethylene and the like. Preferred alkylene group includes a methylene group.

The optionally substituted methylene group includes, for example, a group shown by the following formula (XII)

wherein $R^a$ and $R^b$ represent, (i) the same or different, a hydrogen atom, a $C_{1-4}$ alkyl group, a $C_{1-4}$ haloalkyl group, an optionally substituted $C_{6-20}$ aryl group, a $C_{1-4}$ alkoxy group, an optionally substituted amino group, a carboxyl group or a salt thereof, an optionally substituted alkoxycarbonyl group, a hydroxymethyl group or an optionally substituted alkoxymethyl group, or (ii) $R^a$ and $R^b$ may form a $C_{5-7}$ cycloalkyl group together with the adjacent carbon atom.

The $C_{1-4}$ alkyl group, the $C_{1-4}$ haloalkyl group and the $C_{1-4}$ alkoxy group in $R^a$ and $R^b$ include those exemplified in $R^1$ to $R^5$. The optionally substituted $C_{6-20}$ aryl group in $R^a$ and $R^b$ includes, for instance, phenyl, 4 methoxyphenyl, 2-nitrophenyl and others. As the substituted amino group, there may be mentioned, for example, a mono- or di-$C_{1-4}$ alkylamino group such as methylamino, dimethylamino, ethylamino, diethylamino and others.

As the substituents for the $C_{6-20}$ aryl group, amino group and the like, there may be referred to those mentioned in the explanation of $R^1$ to $R^5$.

As the salt of the carboxyl group represented by $R^a$ and $R^b$, any salt can be employed. A salt which is pharmacologically acceptable may frequently be used. Examples of such salt include a salt with an inorganic base such as an alkali metal salt (e.g. a sodium salt or a potassium salt), an alkaline earth metal salt (for instance, a magnesium salt, a calcium salt or a barium salt), a metal salt (e.g. a zinc salt or an aluminum salt) and an ammonium salt; a salt with an organic base such as a salt with pyridine, a tri-$C_{1-13}$ alkylamine (e.g. trimethylamine, triethylamine, etc.) and so on.

The optionally substituted alkoxycarbonyl group in $R^a$ and $R^b$ includes, for instance, an optionally substituted $C_{2-5}$ alkoxycarbonyl group as mentioned in $R^1$ to $R^5$.

As examples of the optionally substituted alkoxymethyl group in $R^a$ and $R^b$, there may be mentioned an optionally substituted a $C_{1-4}$ alkoxy-methyl group which may be substituted on the alkyl with a substituent. Such substituent for the alkoxymethyl group include, for example, a carboxyl group, a $C_{2-5}$ alkoxycarbonyl group, a hydroxyl group and a $C_{1-4}$ alkoxy group. The $C_{2-5}$ alkoxycarbonyl group and the $C_{1-4}$ alkoxy group in the $C_{1-4}$ alkoxy-methyl group can be referred to the groups as mentioned in $R^1$ to $R^5$. Typical examples of the optionally substituted alkoxymethyl group include (a) a $C_{1-4}$ alkoxy-methyl group such as methoxymethyl, ethoxymethyl, propoxymethyl, isopropoxymethyl, butoxymethyl, isobutoxymethyl, s-butoxymethyl and t-butoxymethyl; (b) a carboxy-$C_{1-4}$ alkoxy-methyl group such as carboxymethoxymethyl, carboxyethoxymethyl, carboxypropoxymethyl, carboxybutoxymethyl, etc.; (c) a $C_{2-5}$ alkoxycarbonyl-$C_{1-4}$ alkoxy-methyl group such as methoxycarbonylmethoxymethyl, ethoxycarbonylmethoxymethyl, isopropoxycarbonylmethoxymethyl, 2-butoxycarbonylethoxymethyl and others; (d) a hydroxy-$C_{1-4}$ alkoxy-methyl group such as 2-hydroxyethoxymethyl, 3-hydroxypropoxymethyl and the like; (e) a $C_{1-4}$ alkoxy-$C_{1-4}$ alkoxymethyl group such as 2-methoxyethoxymethyl, 2-ethoxyethoxymethyl, 3-methoxypropoxymethyl and so on.

The $C_{5-7}$ cycloalkyl group includes cyclopentyl, cyclohexyl and cycloheptyl groups.

As preferred examples of the optionally substituted methylene group shown by the formula (XII), there may be mentioned, for instance, (a) the group of the formula (XII) wherein $R^a$ and $R^b$ are, the same or different, a hydrogen atom, a $C_{1-4}$ alkyl group or a $C_{5-7}$ cycloalkyl group formed with $R^a$, $R^b$ and the adjacent carbon atom (e.g. a methylene group, a $C_{2-4}$ alkylidene group such as an ethylidene group and an isopropylidene group; a $C_{5-7}$ cycloalkylidene group such as a cyclopentylidene and a cyclohexylidene, and so on); (b) the group of the formula (XII) where $R^a$ and $R^b$ are respectively a carboxyl group or a salt thereof, an optionally substituted alkoxycarbonyl group, a hydroxymethyl group or an optionally substituted alkoxymethyl group. Specifically preferred is the group of the formula (XII) where $R^a$ and $R^b$ are, the same or different, a carboxyl group or a salt thereof, or a $C_{2-5}$ alkoxycarbonyl group.

As preferred examples of $R^7$ and $R^8$, there may be mentioned (1) a hydrogen atom, a hydroxyl group which may be protected with a protective group, or (2) $R^7$ is the group shown by the formula (IX): —O—$R^7$, and $R^8$ is the group of the formula (X) : —O—$R^{8a}$.

Practically preferred examples of $R^7$ and $R^8$ include, a hydrogen atom, a hydroxyl group which may be protected with a protective group selected from $C_{1-4}$ alkyl group, a $C_{7-20}$ aralkyl group or a $C_{1-6}$ acyl group; or $R^7$ and $R^8$ are respectively the group of the formula (IX)—O—$R^{7a}$ and the group (X)—O—$R^{8a}$, and in the optionally substituted methylene group if the general formula (XII) formed by incorporation of $R^1$ and $R^2$ where $R^a$ and $R^b$ are respectively a carboxyl group or a salt thereof, or a $C_{2-5}$ alkoxycarbonyl group.

The halogen atom, the optionally substituted lower alkyl group, the optionally substituted cycloalkyl group, the protective group for hydroxyl group, the optionally substituted alkoxy group, the optionally substituted cycloalkyloxy group, the optionally substituted aralkyloxy group, the optionally substituted aryloxy group, the optionally substituted lower alkylthio group, the optionally substituted acyl group, the protective group for carboxyl group, the optionally substituted lower alkoxy carbonyl group, the optionally substituted amino group in $R^6$, $R^9$ and $R^{10}$ include, for example, those mentioned in $R^1$ to $R^5$ and $R^7$, $R^8$.

As examples of the optionally substituted aralkylthio group, there may be mentioned a $C_{7-20}$ alkylthio group (for example, benzylthio, or naphthylthio group) which may be substituted with a substituent such as a $C_{1-4}$ alkyl group, a hydroxyl group, a $C_{1-4}$ alkoxy group, a nitro group, a halogen atom and others.

The optionally substituted aryl group and the optionally substituted aralkyl group include, for instance, the optionally substituted $C_{6-16}$ aryl group and the optionally substituted $C_{7-20}$ aralkyl group as mentioned in the explanation of the protective group for hydroxyl group.

As the substituent for the lower alkyl group and the lower alkoxy group, an optionally substituted amino group as mentioned above can also be employed.

Typical examples of $R^6$, $R^9$ and $R^{10}$ include a hydrogen atom, a $C_{1-4}$ alkyl group, specifically a hydrogen atom.

Examples of the lower alkyl group in $R^{11}$ include a $C_{1-4}$ alkyl group as mentioned in Rto $R^5$. Methyl group and ethyl group, specifically methyl group, can advantageously be used as $R^{11}$.

As examples of the compound of the general formula (VIII) there may be mentioned, methyl phenylmethyl ketone (phenyl acetone); a phenylacetone derivative such as ethyl benzyl ketone, propyl phenylmethyl ketone, isopropyl phenylmethyl ketone, butyl phenylmethyl ketone, isobutyl phenylmethyl ketone, s-butyl phenylmethyl ketone, t-butyl phenylmethyl ketone, and so on; a derivative having a substituent on the 2-position of the phenyl group such as methyl-2-methylphenylmethyl ketone, ethyl-2-chlorophenylmethyl ketone, methyl 2-ethylphenylmethyl ketone, ethyl 2-methylphenylmethyl ketone, methyl 2-methoxyphenylmethyl ketone, methyl 2-benzyloxyphenylmethyl ketone, ethyl 2-benzyloxyphenylmethyl ketone and so on; a derivative having a substituent on the 3-position of the phenyl group such as methyl 3-methylphenylmethyl ketone, ethyl 3-chlorophenylmethyl ketone, methyl 3-methoxycarbonyl-2-methoxyphenylmethyl ketone, ethyl 3-methoxycarbonyl-2-methoxyphenylmethyl ketone, methyl 2-methyl-3-aminoethoxyphenylacetone and others; a derivative substituted on the 4-position of the phenyl group such as methyl 4-methylphenylmethyl ketone, ethyl 4-methylphenylmethyl ketone, 4-ethylphenylmethyl ketone, ethyl 4-ethylphenylmethyl ketone, 4-hydroxyphenylmethyl ketone, ethyl 4-hydroxyphenylmethyl ketone, methyl-4-methoxyphenylmethyl ketone, ethyl 4-methoxyphenylketone, methyl-4-benzyloxyphenylmethyl ketone, ethyl-4-benzyloxyphenylmethyl ketone, methyl-4-hydroxyethoxyphenylmethyl ketone, methyl-4-(2-ethoxyethoxy)phenylmethyl ketone, methyl-4 (2-dimethylaminoethoxy)phenylmethyl ketone, methyl-4-methylthiophenylmethyl ketone, methyl-4-benzylthiophenylmethyl ketone, methyl-4-hydroxycarbonylphenylmethyl=ketone, methyl-4-methoxycarbonylphenylmethyl ketone, methyl 4-carbamoylphenylmethyl ketone, methyl4-dimethylaminocarbonylphenylmethyl ketone, methyl-4-benzylaminocarbonylphenylmethyl ketone, methyl 4-aminophenylmethyl ketone, methyl 4-acetylaminophenylmethyl=ketone, methyl 4-acetylaminomethylphenylmethyl ketone, methyl 4-ethoxycarbonylaminophenylmethyl ketone, methyl 4-methoxycarbonylmethylaminophenylmethyl ketone, methyl 4-acetylphenylmethyl ketone, methyl 4-(o-methoxyphenyl)phenylmethyl ketone, methyl 4-(m-methoxycarbonylphenyl)phenylmethyl ketone, methyl 4-(p-chlorophenyl)phenylmethyl ketone, methyl 4-(p-hydroxyphenyl)phenylmethyl ketone, methyl 4-(p-chlorophenylmethyl)phenylmethyl ketone, methyl 4-(p-methoxyphenylmethyl)phenylmethyl ketone, and the like; a derivative substituted with substituents on the 2,4-positions, 2,5-positions or 3,4-positions of the phenyl group such as methyl 2-methoxy-4-methoxycarbonylphenylmethyl ketone, methyl-3,4-dimethoxyphenylmethyl ketone, methyl 3,4-dihydroxyphenylmethyl ketone, ethyl 3,4-dihydroxyphenylmethyl ketone, methyl 3,4-dimethoxycarbonylphenylmethyl ketone, ethyl-3,4-dimethoxycarbonylphenylmethyl ketone, methyl-3-methoxy-4-methoxycarbonylphenylmethyl ketone, methyl 3-methyl-4-methoxyphenylmethyl ketone, methyl=3-methylamino-4-benzyloxyphenylmethyl ketone, methyl-3-methoxycarbonyl-4-hydroxyphenylmethyl ketone, methyl 3-chloro-4-hydroxyphenylmethyl ketone, methyl 3-fluoro-4-methoxycarbonylphenylmethyl ketone, methyl-3-fluoro-4-methylaminoethoxyphenylmethyl=ketone, 2-iodo-5-methoxyphenylmethyl ketone, etc.; a derivative substituted with substituents on the 2,3,4-positions or the 2,4,5-positions of the phenyl group such as 2,3,4-trimethoxyphenylmethyl ketone, methyl-3,5-difluoro-4-methoxyphenylmethyl ketone, and others; a $C_{1-4}$ alkyl (1,3- benzodioxol-5-yl)methyl ketone such as methyl (1,3-benzodioxol-5-yl)methyl ketone; a $C_{1-4}$ alkyl (2,2-di-$C_{1-4}$ alkyl-1,3-benzodioxol-5-yl)methyl ketone derivative such as methyl (2,2-dimethyl-1,3-benzodioxol-5-yl)methyl ketone; a $C_{1-4}$ alkyl [2,2-bis($C_{2-5}$ alkoxycarbonyl)-1,3-benzodioxol-5-yl]methyl ketone such as [dimethyl-5-(2-oxopropyl)-1,3-benzodioxole-2,2-dicarboxylate], methyl [diethyl 5-(2-oxopropyl)-1,3-benzodioxole-2,2-dicarboxylate], methyl (2,2-dimethoxycarbonyl-1,3-benzodioxol-5-yl) methyl ketone, ethyl (2,2-dimethoxycarbonyl-1,3-benzodioxol-5-yl) methyl ketone, methyl (2,2-bisethoxycarbonyl-1,3-benzodioxol-5-yl) methyl ketone and so on; a $C_{1-4}$ alkyl [2,2-di(hydroxy-$C_{1-4}$ alkoxy-$C_{1-4}$ alkyl)-1,3-benzodioxol-5-yl]methyl ketone such as methyl (2,2-dihydroxyethoxymethyl-1,3-benzodioxol-5-yl)methyl ketone; a $C_{1-4}$ alkyl [2,2-di-($C_{2-5}$ alkoxycarbonyl-$C_{1-4}$ alkoxy-$C_{1-4}$ alkyl)-1,3-benzodioxol-5-yl]methyl ketone derivative such as methyl [2,2-di (methoxycarbonylmethoxymethyl)-1,3-benzodioxol-5-yl] methyl ketone, ethyl=[2,2-di-(methoxycarbonylmethoxymethyl)-1,3-benzodioxol-5-yl] methyl ketone and so on; a $C_{1-4}$ alkyl (1,4-benzodioxin-6-yl)methyl ketone derivative such as methyl (1,4-benzodioxin-6-yl)methyl ketone and the like.

As preferred examples of the above compounds, there may be mentioned a $C_{1-4}$ alkyl=phenylmethyl ketone derivative; a $C_{1-4}$ alkyl 3,4-di-$C_{1-4}$ alkoxy-phenylmethyl ketone derivative; a $C_{1-4}$ alkyl 3,4-dihydroxyphenylmethyl ketone derivative; a $C_{1-4}$ alkyl 3,4-dihydroxyphenylmethyl ketone derivative; a $C_{1-4}$ alkyl [2,2-bis($C_{2-5}$ alkoxycarbonyl)-1,3-benzodioxol-5-yl]methyl ketone derivative; a $C_{1-4}$ alkyl [2,2-di-($C_{2-5}$ alkoxycarbonyl-$C_{1-4}$ alkoxy-$C_{1-4}$ alkyl)-1,3-benzodioxol-5-yl]methyl ketone derivative.

The compound shown by the general formula (XI) is a compound obtainable by a combination of the (R)-2-amino-1-phenylethanol derivative of the general formula (II) and the phenylacetone derivative of the general formula (VIII), and practically includes, for example, (a) an (R,R)-1-phenyl-2-[(2-phenyl-1-$C_{1-4}$ alkyl-ethyl)amino]ethanol derivative, (b) an (R,R)-1-phenyl-2-[[2-(2-substituted phenyl)-1-$C_{1-4}$ alkyl-ethyl]amino]ethanol derivative, (c) an (R,R)-1-phenyl-2-[[2-(3-substituted phenyl)-1-$C_{1-4}$ alkyl-ethyl]amino]ethanol derivative, (d) an (R,R)-1-phenyl-2-[[2-(4-substituted phenyl)-1-$C_{1-4}$ alkyl-ethyl]amino]ethanol derivative, (e) an (R,R)-1-phenyl-2-[[2-(3,4-di-substituted phenyl)-1-$C_{1-4}$ alkyl-ethyl]amino]ethanol derivative, (f) an (R,R)-1-(2-halophenyl)-2-[(2-phenyl-1-$C_{1-4}$ alkyl-ethyl)amino]ethanol derivative, (g) an (R,R)-1-(2-substituted phenyl)-2-[(2-phenyl-1-$C_{1-4}$ alkyl-ethyl)amino]ethanol derivative, (h) an (R,R)-1-(3-halophenyl)-2-[(2-phenyl-1-$C_{1-4}$ alkyl-ethyl)amino]ethanol derivative, (i) an (R,R)-1-(3-substituted phenyl)-2-[(2-phenyl-1-$C_{1-4}$ alkyl-ethyl)amino]ethanol derivative, (j) an (R,R)-1-(4-halophenyl)-2-[(2-phenyl-1-$C_{1-4}$ alkyl-ethyl)amino]ethanol derivative, (k) an (R,R)-1-(4-substituted phenyl)-2-[(2-phenyl-1-$C_{1-4}$ alkyl-ethyl)amino]ethanol derivative, (l) an (R,R)-1-(2,3-di-halophenyl)-2-[(2-phenyl-1-$C_{1-4}$ alkyl-ethyl)amino] ethanol derivative, (m) an (R,R)-1-(2,4-di-substituted phenyl)-2-[(2-phenyl-1-$C_{1-4}$ alkyl-ethyl)amino]ethanol derivative, (n) an (R,R)-1-(3,4-di-halophenyl)-2-[(2-phenyl-1-$C_{1-4}$ alkyl-ethyl)amino]ethanol derivative, (o) an (R,R)-1-(3,4-di-substituted phenyl)-2-[(2-phenyl-1-$C_{1-4}$ alkyl-ethyl)amino]ethanol derivative, (p) an (R,R)-1-(3,5-di-substituted phenyl)-2-[(2-phenyl-1-$C_{1-4}$ alkyl-ethyl)amino] ethanol derivative, (q) an (R,R)-1-(3,4,5-tri-substituted phenyl)-2-[(2-phenyl-1-$C_{1-4}$ alkyl-ethyl)amino]ethanol derivative and so on.

(a) The (R,R)-1-phenyl-2-[(2-phenyl-1-$C_{1-4}$ alkyl-ethyl) amino]ethanol derivative include, for example, (R,R)-1-phenyl-2-[(2-phenyl-1-methylethyl)amino]ethanol, (R,R)-1-phenyl-2-[(2-phenyl-1-ethylethyl)amino]ethanol, (R,R)-1-phenyl-2-[(2-phenyl-1-propylethyl)amino]ethanol, (R,R)-1-phenyl-2-[(2-phenyl-1-isopropylethyl)amino]ethanol, (R,R)-1-phenyl-2-[(2-phenyl-1-butylethyl)amino]ethanol, (R,R)-1-phenyl-2-[(2-phenyl-1-isobutylethyl)amino] ethanol, (R,R)-1-phenyl-2-[(2-phenyl-1-s-butylethyl) amino]ethanol, (R,R)-1-phenyl-2-[(2-phenyl-1-t-butylethyl) amino]ethanol and the like.

(b) Examples of the (R,R)-1-phenyl-2-[[2-(2-substituted phenyl)-1-$C_{1-4}$ alkyl-ethyl]amino]ethanol derivative include (R,R)-1-phenyl-2-[[2-(2-chlorophenyl)-1-methylethyl]amino]ethanol, (R,R)-1-phenyl-2-[[2-(2-methylphenyl)-1-methylethyl]amino]ethanol, (R,R)-1-phenyl-2-[[2-(2-methoxyphenyl)-1-methylethyl]amino] ethanol, (R,R)-1-phenyl-2-[[2-(2-benzyloxyphenyl)-1-methylethyl]amino]ethanol, and others.

(c) As the (R,R)-1-phenyl-2-[[2-(3-substituted phenyl)-1-$C_{1-4}$ alkyl-ethyl]amino]ethanol derivative, there may be mentioned, for example, (R,R)-1-phenyl-2-[[2-(3-methylphenyl)-1-methylethyl]amino]ethanol, (R,R)-1-phenyl-2-[[2-(3-methoxyphenyl)-1-methylethyl]amino] ethanol, (R,R)-1-phenyl-2-[[2-(3-methylaminoethoxyphenyl)-1-methylethyl]amino]ethanol and so on.

(d) The (R,R)-1-phenyl-2-[[2-(4-substituted phenyl)-1-$C_{1-4}$ alkyl-ethyl]amino]ethanol derivative includes, for instance, (R,R)-1-phenyl-2-[[2-(4-phenylphenyl)-1-methylethyl]amino]ethanol, (R,R)-1-phenyl-2-[[2-(4-methylphenyl)-1-methylethyl]amino]ethanol, (R,R)-1-phenyl-2-[[2-(4-ethylphenyl)-1-methylethyl]amino]ethanol, (R,R)-1-phenyl-2-[[2-(4-hydroxyphenyl)-1-methylethyl] amino]ethanol, (R,R)-1-phenyl-2-[[2-(4-methoxyphenyl)-1-methylethyl]amino]ethanol, (R,R)-1-phenyl-2-[[2-(4-benzyloxyphenyl) 1-methylethyl]amino]ethanol, (R,R)-1-phenyl-2-[[2-(4-hydroxyethoxyphenyl)-1-methylethyl] amino]ethanol, (R,R)-1-phenyl-2-[[2-(4-dimethylaminomethoxyphenyl)-1-methylethyl]amino] ethanol, (R,R)-1-phenyl-2-[[2-(4-methylthiophenyl)-1-methylethyl]amino]ethanol, (R,R)-1-phenyl-2-[[2-(4-benzylthiophenyl)-1-methylethyl]amino]ethanol, (R,R)-1-phenyl-2-[[2-(4-hydroxycarbonylphenyl)-1-methylethyl] amino]ethanol, (R,R)-1-phenyl-2-[[2-(4-methoxycarbonylphenyl)-1-methylethyl]amino]ethanol, (R,R)-1-phenyl-2-[[2-(4-carbamoylphenyl)-1-methylethyl] amino]ethanol, (R,R)-1-phenyl-2-[[2-(4-dimethylaminocarbonylphenyl)-1-methylethyl]amino] ethanol, (R,R)-1-phenyl-2-[[2-(4-benzylaminocarbonylphenyl)-1-methylethyl]amino] ethanol, (R,R)-1-phenyl-2-[[2-(4-acetylaminocarbonylphenyl)-1-methylethyl]amino] ethanol, (R,R)-1-phenyl-2-[[2-(4-acetylaminomethylphenyl)-1-methylethyl]amino]ethanol, (R,R)-1-phenyl-2-[[2-(4-acetylphenyl)-1-methylethyl] amino]ethanol and others.

(e) Examples of the (R,R)-1-phenyl-2-[[2-(3,4-di-substituted phenyl)-1-$C_{1-4}$ alkyl-ethyl]amino]ethanol derivative include (R,R)-1-phenyl-2-[[2-(3,4-dimethoxyphenyl)-1-methylethyl]amino]ethanol, (R,R)-1-phenyl-2-[[2-(3,4-dimethoxyphenyl)-1-ethylethyl]amino] ethanol, (R,R)-1-phenyl-2-[[2-(3,4-dimethoxyphenyl)-1-propylethyl]amino]ethanol, (R,R)-1-phenyl-2-[[2-[3,4-(bismethoxycarbonylmethoxy)methylenedioxyphenyl]1-methylethyl]amino]ethanol and the like.

(f) As the (R,R)-1-(2-halophenyl)-2-[(2-phenyl-1-$C_{1-4}$ alkyl-ethyl)amino]ethanol derivative, there may be mentioned, for instance, (R,R)-1-o-chlorophenyl-2-[(2-phenyl-1-methylethyl)amino]ethanol, (R,R)-1-(2-chlorophenyl)-2-[[2-(2-chlorophenyl)-1-methylethyl] amino]ethanol, (R,R)-1-(2-chlorophenyl)-2-[[2-(2-methylphenyl)-1-methylethyl]amino]ethanol, (R,R)-1-(2-chlorophenyl)-2-[[2-(2-methoxyphenyl)-1-methylethyl] amino]ethanol, (R,R)-1-(2-chlorophenyl)-2-[[2-(3,4-dimethoxyphenyl)-1-methylethyl]amino]ethanol, (R,R)-1-(2-fluorophenyl)-2-[(2-phenyl-1-methylethyl)amino] ethanol, (R,R)-1-(2-fluorophenyl)-2-[[2-(2-chlorophenyl)-1-methylethyl]amino]ethanol, (R,R)-1-(2-fluorophenyl)-2-[ [2-(2-methylphenyl)-1-methylethyl]amino]ethanol, (R,R)-1-(2-fluorophenyl)-2-[[2-(2-methoxyphenyl)-1-methylethyl]amino]ethanol, (R,R)-1-(2-fluorophenyl)-2-[ [2-(3,4-dimethoxyphenyl)-1-methylethyl]amino]ethanol, etc.

(g) Examples of the (R,R)-1-(2-substituted phenyl)-2-[(2-phenyl-1-$C_{1-4}$ alkyl-ethyl)amino]ethanol derivative include (R,R)-1-(2-methylphenyl)-2-phenyl-1-methylethyl)amino] ethanol, (R,R)-1-(2-methylphenyl)-2-[[2-(2-chlorophenyl)-1-methylethyl]amino]ethanol, (R,R)-1-(2-methylphenyl)-2-[[2-(2-methylphenyl)-1-methylethyl]amino]ethanol, (R,R)-1-(2-methylphenyl)-2-[[2-(2-methoxyphenyl)-1-methylethyl]amino]ethanol, (R,R)-1-(2-methylphenyl)-2-[ [2-(3,4-dimethoxyphenyl)-1-methylethyl]amino]ethanol, (R,R)-1-(2-hydroxyphenyl)-2-[(2-phenyl-1-methylethyl) amino]ethanol, (R,R)-1-(2-hydroxyphenyl)-2-[[2-(2-chlorophenyl)1-methylethyl]amino]ethanol, (R,R)-1-(2-hydroxyphenyl)-2-[[2-(2-methylphenyl)-1-methylethyl] amino]ethanol, (R,R)-1-(2-hydroxyphenyl)-2-[[2-(2-methoxyphenyl)-1-methylethyl]amino]ethanol, (R,R)-1-(2-hydroxyphenyl)-2-[[2-(3,4-dimethoxyphenyl)-1-methylethyl]amino]ethanol, (R,R)-1-(2-methoxyphenyl)-2-[ (2-phenyl-1-methylethyl)amino]ethanol, (R,R)-1-(2-methoxyphenyl)-2-[[2-(2-chlorophenyl)-1-methylethyl] amino]ethanol, (R,R)-1-(2-methoxyphenyl)-2-[[2-(2-methylphenyl)-1-methylethyl]amino]ethanol, (R,R)-1-(2-methoxyphenyl)-2-[[2-(2-methoxyphenyl)-1-methylethyl] amino]ethanol, (R,R)-1-(2-methoxyphenyl)-2-[[2-(3,4-dimethoxyphenyl)-1-methylethyl]amino]ethanol, (R,R)-1-(2-benzyloxyphenyl)-2-[(2-phenyl-1-methylethyl)amino] ethanol, (R,R)-1-(2-benzyloxyphenyl)-2-[[2-(2-chlorophenyl)-1-methylethyl]amino]ethanol, (R,R)-1-(2-benzyloxyphenyl)-2-[[2-(2-methylphenyl)-1-methylethyl] amino]ethanol, (R,R)-1-(2-benzyloxyphenyl)-2-[[2-(2-methoxyphenyl)-1-methylethyl]amino]ethanol, (R,R)-1-(2-benzyloxyphenyl)-2-[[2-(3,4-dimethoxyphenyl)-1-methylethyl]amino]ethanol, (R,R)-1-(2-benzylcarbonylphenyl)-2-[(2-phenyl-1-methylethyl)amino] ethanol and so on.

(h) As the (R,R)-1-(3-halophenyl)-2-[(2-phenyl-1-$C_{1-4}$ alkyl-ethyl)amino]ethanol derivative, there may be mentioned, for example, (R,R)-1-(3-chlorophenyl)-2-[(2-phenyl-1-methylethyl)amino]ethanol, (R,R)-1-(3-chlorophenyl)-2-[[2-(2-chlorophenyl)1-methylethyl]amino] ethanol, (R,R)-1-(3-chlorophenyl)-2-[[2-(2-methylphenyl)-1-methylethyl]amino]ethanol, (R,R)-1-(3-chlorophenyl)-2-[ [2-(2-methoxyphenyl)-1-methylethyl]amino]ethanol, (R,R)-1-(3-chlorophenyl)-2-[[2-(2-benzyloxyphenyl)-1-methylethyl]amino]ethanol, (R,R)-1-(3-chlorophenyl)-2-[ [2-(3-methylphenyl)-1-methylethyl]amino]ethanol, (R,R)-1-(3-chlorophenyl)-2-[[2-(3-methoxyphenyl)-1-methylethyl]amino]ethanol, (R,R)-1-(3-chlorophenyl)-2-[ [2-(3-methylaminoethoxyphenyl)-1-methylethyl]amino] ethanol, (R,R)-1-(3-chlorophenyl)-2-[[2-(4-methylphenyl)-1-methylethyl]amino]ethanol, (R,R)-1-(3-chlorophenyl)-2-[ [2-(4-ethylphenyl)-1-methylethyl]amino]ethanol, (R,R)-1-(3-chlorophenyl)-2-[[2-(4-phenylphenyl)-1-methylethyl] amino]ethanol, (R,R)-1-(3-chlorophenyl)-2-[[2-(4-hydroxyphenyl)-1-methylethyl]amino]ethanol, (R,R)-1-(3-chlorophenyl)-2-[[2-(4-hydroxyphenyl)-1-ethylethyl] amino]ethanol, (R,R)-1-(3-chlorophenyl)-2-[[2-(4-methoxyphenyl)-1-methylethyl]amino]ethanol, (R,R)-1-(3-chlorophenyl)-2-[[2-(4-benzyloxyphenyl)1-methylethyl] amino]ethanol, (R,R)-1-(3-chlorophenyl)-2-[[2-(4-hydroxyethoxyphenyl)-1-methylethyl]amino]ethanol, (R,R)-1-(3-chlorophenyl)-2-[[2-(4-dimethylaminomethoxyphenyl)-1-methylethyl]amino] ethanol, (R,R)-1-(3-chlorophenyl)-2-[[2-(4-methylthiophenyl)-1-methylethyl]amino]ethanol, (R,R)-1-(3-chlorophenyl)-2-[[2-(4-benzylthiophenyl)-1-methylethyl]amino]ethanol, (R,R)-1-(3-chlorophenyl)-2-[ [2-(4-hydroxycarbonylphenyl)-1-methylethyl]amino] ethanol, (R,R)-1-(3-chlorophenyl)-2-[[2-(4-methoxycarbonylphenyl)-1-methylethyl]amino]ethanol, (R,R)-1-(3-chlorophenyl)-2-[[2-(4-carbamoylphenyl)-1-methylethyl]amino]ethanol, (R,R)-1-(3-chlorophenyl)-2-[ [2-(4-dimethylaminocarbonylphenyl)-1-methylethyl] amino]ethanol, (R,R)-1-(3-chlorophenyl)- 2-[[2-(4-benzylaminocarbonylphenyl)-1-methylethyl]amino] ethanol, (R,R)-1-(3-chlorophenyl)-2-[[2-(4-acetylaminocarbonylphenyl)-1-methylethyl]amino]ethanol, (R,R)-1-(3-chlorophenyl)-2-[[2-(4-acetylaminomethylphenyl)1-methylethyl]amino]ethanol, (R,R)-1-(3-chlorophenyl)-2-[[2-(4-acetylphenyl)-1-methylethyl]amino]ethanol, (R,R)-1-(3-chlorophenyl)-2-[ [2-(3,4-dimethoxyphenyl)-1-methylethyl]amino]ethanol, (R,R)-1-(3-chlorophenyl)-2-[[2-(3,4-dimethoxyphenyl)-1-ethylethyl]amino]ethanol, (R,R)-1-(3-chlorophenyl)-2-[[2-[3,4-(bismethoxycarbonylmethoxy)methylenedioxyphenyl] -1-methylethyl]amino]ethanol, (R,R)-1-(3-chlorophenyl)-2-[[2-[3,4-(bismethoxycarbonylmethoxy) methylenedioxyphenyl]-1-ethylethyl]amino]ethanol, (R,R)-1-(3-fluorophenyl)-2-[(2-phenyl-1-methylethyl)amino] ethanol and so on.

(i) As examples of the (R,R)-1-(3-substituted phenyl)-2-[(2-phenyl-1-$C_{1-4}$ alkyl-ethyl)amino]ethanol derivative, there may be mentioned (R,R)-1-(3-methylphenyl)-2-[(2-phenyl-1-methylethyl)amino]ethanol, (R,R)-1-(3-methylphenyl)-2-[[2-(2-chlorophenyl)-1-methylethyl] amino]ethanol, (R,R)-1-(3-methylphenyl)-2-[[2-(2-methoxyphenyl)-1-methylethyl]amino]ethanol, (R,R)-1-(3-methylphenyl)-2-[[2-(3,4-dimethoxyphenyl)-1-methylethyl]amino]ethanol, (R,R)-1-(3-hydroxyphenyl)-2-[ (2-phenyl)-1-methylethylamino]ethanol, (R,R)-1-(3-trifluoromethylphenyl)-2-[(2-phenyl)-1-methylethylamino] ethanol, (R,R)-1-(3-trifluoromethylphenyl)-2-[[2-(2-chlorophenyl)-1-methylethyl]amino]ethanol, (R,R)-1-(3-trifluoromethylphenyl)-2-[[2-(2-methylphenyl)-1-methylethyl]amino]ethanol, (R,R)-1-(3-trifluoromethylphenyl)-2-[[2-(2-methoxyphenyl)-1-methylethyl]amino]ethanol, (R,R)-1-(3-trifluoromethylphenyl)-2-[[2-(4-benzylphenyl)-1-methylethyl]amino]ethanol, (R,R)-1-(3-trifluoromethylphenyl)-2-[[2-(3,4-dimethoxyphenyl)-1-methylethyl]amino]ethanol, (R,R)-1-(3-trifluoromethylphenyl)-2-[[2-(3,4-dimethoxyphenyl)-1-ethylethyl]amino]ethanol, etc.

(j) The (R,R)-1-(4-halophenyl)-2-[(2-phenyl-1-$C_{1-4}$ alkyl-ethyl)amino]ethanol derivative includes, for instance, (R,R)-1-(4-chlorophenyl)-2-[(2-phenyl-1-methylethyl] amino]ethanol, (R,R)-1-(4-chlorophenyl)-2-[[2-(2-chlorophenyl)-1-methylethyl]amino]ethanol, (R,R)-1-(4-chlorophenyl)-2-[[2-(2-methylphenyl)-1-methylethyl]

amino]ethanol, (R,R)-1-(4 chlorophenyl)-2-[[2-(2-methoxyphenyl)-1-methylethyl]amino]ethanol, (R,R)-1-(4-chlorophenyl)-2-[[2-(3,4-dimethoxyphenyl)-1-methylethyl]amino]ethanol and the like.

(k) Examples of the (R,R)-1-(4-substituted phenyl)-2-[(2-phenyl-1-$C_{1-4}$ alkyl-ethyl)amino]ethanol derivative include, (R,R)-1-(4-methylphenyl)-2-[(2-phenyl- 1-methylethyl) amino]ethanol, (R,R)-1-(4-methylphenyl)-2-[[2-(2-chlorophenyl)-1-methylethyl]amino]ethanol, (R,R)-1-(4-methylphenyl)-2-[[2-(2-methoxyphenyl)-1-methylethyl] amino]ethanol, (R,R)-1-(4-methylphenyl)-2-[[2-(3,4-dimethoxyphenyl)-1-methylethyl]amino]ethanol, (R,R)-1-(4-hydroxyphenyl)-2-[(2-phenyl-1-methylethyl) amino] ethanol, (R,R)-1-(4-hydroxyphenyl)-2-[[2-(3,4-dimethoxyphenyl)-1-methylethyl]amino]ethanol, (R,R)-1-(4-trifluoromethylphenyl)-2-[(2-phenyl-1-methylethyl]amino]ethanol, (R,R)-1-(4-trifluoromethylphenyl)-2-[[2-(2-chlorophenyl)-1-methylethyl]amino]ethanol, (R,R)-1-(4-trifluoromethylphenyl)-2-[[2-(2-methylphenyl)-1-methylethyl]amino]ethanol, (R,R)-1-(4-trifluoromethylphenyl)-2-[[2-(2-methoxyphenyl)-1-methylethyl]amino]ethanol, (R,R)-1-(4-trifluoromethylphenyl)-2-[[2-(3,4-dimethoxyphenyl)-1-methylethyl]amino]ethanol, (R,R)-1-(4-methoxyphenyl)-2-[[2-(4-methoxyphenyl)-1-methylethyl]amino]ethanol and so on.

(1) As the (R,R)-1-(2,3-di-substituted phenyl)-2-[(2-phenyl-1-$C_{1-4}$ alkyl-ethyl)amino]ethanol derivative, there may be mentioned, for instance, (R,R)-1-(2-fluoro-3-chlorophenyl)-2-[(2-phenyl-1-methylethyl]amino]ethanol, (R,R)-1-(2-fluoro-3-chlorophenyl)-2-[[2-(2-chlorophenyl)-1-methylethyl]amino]ethanol, (R,R)-1-(2-fluoro-3-chlorophenyl)-2-[[2-(2-methylphenyl)-1-methylethyl] amino]ethanol, (R,R)-1-(2-fluoro-3-chlorophenyl)-2-[[2-(2-methoxyphenyl)-1-methylethyl]amino]ethanol, (R,R)-1-(2-fluoro-3-chlorophenyl)-2-[[2-(3,4-dimethoxyphenyl)1-methylethyl]amino]ethanol, (R,R)-1-(2-fluoro-3-chlorophenyl)-2-[[2-[3,4-(bismethoxycarbonylmethoxy)methylenedioxyphenyl]-1-methylethyl]amino]ethanol, (R,R)-1-(2-chloro-3-hydroxyphenyl)-2-[(2-phenyl-1-ethylethyl]amino]ethanol and others.

(m) The (R,R)-1-(2,4-di-substituted phenyl)-2-[(2-phenyl-1-$C_{1-4}$ alkyl-ethyl)amino]ethanol derivative includes, for example, (R,R)-1-(2-chloro-4-hydroxyphenyl)-2-[(2-phenyl-1-methylethyl]amino]ethanol, (R,R)-1-(2-chloro-4-benzyloxyphenyl)-2-[(2-phenyl-1-methylethyl]amino]ethanol, and the like.

(n) Examples of the (R,R)-1-(3,4-di-halophenyl)-2-[(2-phenyl-1-$C_{1-4}$ alkyl-ethyl)amino]ethanol derivative include (R,R)-1-(3,4-dichlorophenyl)-2-[(2-phenyl-1-methylethyl]amino]ethanol, (R,R)-1-(3,4-dichlorophenyl)-2-[[2-(2-chlorophenyl)-1-methylethyl]amino]ethanol, (R,R)-1-(3,4-dichlorophenyl)-2-[[2-(2-methylphenyl)-1-methylethyl] amino]ethanol, (R,R)-1-(3,4-dichlorophenyl)-2-[[2-(2-methoxyphenyl)-1-methylethyl]amino]ethanol, (R,R)-1-(3,4-dichlorophenyl)-2-[[2-(3,4-dimethoxyphenyl)-1-methylethyl]amino]ethanol, (R,R)-1-(3,4-dichlorophenyl)-2-[[2-(3,4-dimethoxyphenyl)-1-ethylethyl]amino]ethanol, (R,R)-1-(3,4-dichlorophenyl)-2-[[2-[3,4-(bismethoxycarbonylmethoxy)methylenedioxyphenyl]-1-methylethyl]amino]ethanol and so on.

(o) As the (R,R)-1-(3,4-di-substituted phenyl)-2-[(2-phenyl-1-$C_{1-4}$ alkyl-ethyl)amino]ethanol derivative, there may be mentioned, for instance, (R,R)-1-(3,4-dihydroxyphenyl)-2-[(2-phenyl-1-methylethyl)amino] ethanol, (R,R)-1-(3,4-dihydroxyphenyl)-2-[[2-(3,4-dihydroxyphenyl)-1-methylethyl]amino]ethanol, (R,R)-1-(3,4-dihydroxyphenyl)-2-[(2-phenyl-1-ethylethyl)amino] ethanol, (R,R)-1-(3,4-dimethoxyphenyl)-2-[(2-phenyl-1-methylethyl)amino]ethanol, (R,R)-1-(3-fluoro-4-methoxyphenyl)-2-[(2-phenyl-1-methylethyl)amino] ethanol, (R,R)-1-[3-(2-hydroxyethoxy)-4-(t-butoxy)phenyl]-2-[(2-phenyl-1- methylethyl)amino]ethanol, (R,R)-1-(3-acetylamino-4-hydroxyphenyl)-2-[(2-phenyl-1-methylethyl)amino]ethanol, (R,R)-1-(3-acetylamino-4-methoxyphenyl)-2-[(2-phenyl-1-methylethyl)amino] ethanol, (R,R)-1-(3-methylthio-4-hydroxyphenyl)-2-[(2-phenyl-1-methylethyl)amino]ethanol, (R,R)-1-(3-hydroxymethyl-4-hydroxyphenyl)-2-[(2-phenyl-1-methylethyl)amino]ethanol, (R,R)-1-(3-methoxycarbonyl-4-hydroxyphenyl)-2-[(2-phenyl-1-methylethyl)amino] ethanol, (R,R)-1-(3-methoxycarbonyl-4-cyclohexyloxyphenyl)-2-[(2-phenyl-1-methylethyl)amino] ethanol, (R,R)-1-(3-carbamoyl-4-hydroxyphenyl)-2-[(2-phenyl-1-methylethyl)amino]ethanol, (R,R)-1-[3-hydroxymethylcarbonylamino-4-(4-methoxyphenylmethyl)phenyl]-2-[(2-phenyl-1-methylethyl)amino]ethanol, etc.

(p) As examples of the an (R,R)-1-(3,5-di-substituted phenyl)-2-[(2-phenyl-1-$C_{1-4}$ alkyl-ethyl)amino]ethanol derivative, (R,R)-1-(3,5-dihydroxyphenyl)-2-[(2-phenyl-1-methylethyl)amino]ethanol, (R,R)-1-(3,5-dibenzyloxyphenyl)-2-[(2-phenyl-1-methylethyl)amino] ethanol, (R,R)-1-(3,5-di-t-butoxycarbonylphenyl)-2-[(2-phenyl-1-methylethyl)amino]ethanol, and the like.

(q) The (R,R)-1-(3,4,5-tri-substituted phenyl)-2-[(2-phenyl-1-$C_{1-4}$ alkyl-ethyl)amino]ethanol derivative includes, for example, (R,R)-1-(3,5-dichloro-4-methylaminophenyl)-2-[(2-phenyl-1-methylethyl)amino] ethanol, (R,R)-1-(4-amino-3-bromo-5-fluorophenyl)-2-[(2-phenyl-1-methylethyl)amino]ethanol, (R,R)-1-(4-benzyloxy-3-chloro-5-methoxyphenyl)-2-[(2-phenyl-1-methylethyl)amino]ethanol, (R,R)-1-(4,5-dihydroxy-3-methylphenyl)-2-[(2-phenyl-1-methylethyl)amino]ethanol and others.

Typical examples of the compounds mentioned above include an (R,R)-1-phenyl-2-[(2-phenyl-1-$C_{1-4}$ alkyl-ethyl) amino]ethanol derivative such as (R,R)-1-phenyl-2-[(2-phenyl-1-methylethyl)amino]ethanol, (R,R)-1-phenyl-2-[(2-phenyl-1-ethylethyl)amino]ethanol and the like; (R,R)-1-phenyl-2-[[2-[3,4-di-substituted (e.g. di-$C_{1-4}$ alkoxy)-phenyl]-1-$C_{1-4}$ alkyl-ethyl]amino]ethanol derivative such as (R,R)-1-phenyl-2-[[2-(3,4-dimethoxyphenyl)-1-methylethyl]amino]ethanol; an (R,R)-1-(3-halophenyl)-2-[(2-phenyl-1-$C_{1-4}$ alkyl-ethyl)amino]ethanol derivative such as (R,R)-1-(3-chloro)phenyl-2-[(2-phenyl-1-methylethyl)amino]ethanol; an (R,R)-1-(3-halophenyl)-2-[[2-[3,4-di-substituted (e.g. 3,4-di-$C_{1-4}$ alkoxy)-phenyl]-1-$C_{1-4}$ alkyl-ethyl]amino]ethanol derivative such as (R,R)-1-(3-chlorophenyl)-2-[[2-(3,4-dimethoxyphenyl)-1-methylethyl]amino]ethanol; an (R,R)-1-(3-substituted phenyl)-2-[(2-phenyl-1-methylethyl)amino]ethanol derivative such as (R,R)-1-(3-methylphenyl)-2-[(2-phenyl-1-methylethyl)amino]ethanol, (R,R)-1-(3-trifluoromethylphenyl)-2-[(2-phenyl-1-methylethyl)amino]ethanol; an (R,R)-1-(3-substituted phenyl)-2-[[2-[3,4-di-substituted (e.g. 3,4-di-$C_{1-4}$ alkoxy)-phenyl]-1-$C_{1-4}$ alkyl-ethyl]amino]ethanol derivative such as (R,R)-1-(3-methylphenyl)-2-[[2-(3,4-dimethoxyphenyl)-1-methylethyl]amino]ethanol, (R,R)-1-(3-trifluoromethylphenyl)-2-[[2-(3,4-dimethoxyphenyl)-1-methylethyl]amino]ethanol and the like; an (R,R)-1-(4-substituted phenyl)-2-[(2-phenyl-1-$C_{1-4}$ alkyl-ethyl)amino] ethanol derivative such as (R,R)-1-(4-chlorophenyl)- 2-[(2-phenyl-1-methylethyl)amino]ethanol; an (R,R)-1-(-4-halophenyl)-2-[[2-[3,4-di-substituted (e.g. 3,4-di-$C_{1-4}$ alkoxy)phenyl]-1-C alkyl-ethyl]amino]ethanol derivative such as (R,R)-1-(4 chlorophenyl)-2-[[2-(3,4-dimethoxyphenyl)-1-methylethyl]amino]ethanol; an (R R)-1-(3 4-di-halophenyl)-2-[(2-phenyl-1-C$_{1-4}$ alkyl-ethyl) amino]ethanol derivative such as (R,R)-1-(3,4 dichlorophenyl)-2-[(2-phenyl-1-methylethyl)amino] ethanol; an (R,R)-1-(3,4 dihalophenyl)-2-[[2-[3,4-di-substituted (e.g. 3,4-di-C$_{1-4}$ alkoxy)phenyl]-1-C$_{1-4}$ alkyl-ethyl]amino]ethanol derivative such as (R,R)-1-(3,4 dichlorophenyl)-2-[[2-(3 4-dimethoxyphenyl)-1-methylethyl]amino]ethanol and so on.

In this method, the phenylacetone derivative of the general formula (VIII) used as a raw material can easily be obtained by a conventional method, for example, dry distillation of a mixture of an acetic acid salt such as an acetic acid with an alkaline earth metal (e.g. calcium acetate and barium acetate) and a phenylacetic acid salt corresponding to the compound of the general formula (VIII) such as a phenyl acetic acid salt with an alkaline earth metal salt (for instance, calcium phenylacetate, barium phenylacetate, etc.) or others (see Org. Synth., Coll. Vol. II, 389 (1943), etc.)

The method of the present invention is characterized by comprising a reaction of the (R)-2-amino-1-phenylethanol compound of the general formula (II) or a salt thereof with the compound of the general formula (VIII) (phenylacetone derivative) and a reducing reaction of the reaction product of the above reaction. The (R,R)-1-phenyl-2-[[2-(phenyl)-1-methylethyl]amino]ethanol derivative of the general formula (XI) obtained in the method includes a corresponding salt.

The reducing reaction may for example be conducted with using a reducing agent. The reaction may also be carried out in the presence of a catalyst for catalytic reduction. The reaction may be carried out, for instance, by (1) a method which comprises dehydrating-condensing the (R)-2-amino-1-phenylethanol derivative of the general formula (II) or a salt thereof and the compound of the general formula (VIII), and then hydrogenating the resultant compound (hereinafter refereed to as stepwise method), (2) a method of allowing the (R)-2-amino-1-phenylethanol compound of the general formula (II) or a salt thereof to react with the compound of the general formula (VIII) and hydrogen in the presence of a catalyst for catalytic reduction (hereinafter referred to as one-pot method), and others.

According to the reductive aminating method as above using an optically active 2-amino-1-phenylethanol compound or a salt thereof and a phenylacetone derivative, the products are only two species of optical isomers. Further, when hydrogenation is conducted using hydrogen in the presence of a catalyst for catalytic reduction, the diastereomer-ratio can be increased significantly and the object optical isomer can be advantageously obtained. Moreover, such a method using a catalyst for catalytic reduction is suitable for commercial production, since the object compound can be isolated only by filtrating off the catalyst for catalytic reduction and distilling off a solvent, and thus after-treatment is easy.

The stepwise method (1) is illustrated hereinbelow.

The stepwise method (1) is characterized in that an imine-form or an enamine-form can certainly or reliably be obtained by conducting dehydrating-condensation before hydrogenation, and the conversion ratio of the raw materials to the object compound can be increased, thus the purification can be carried out easily.

The dehydrating-condensation of the 2-amino-1-phenylethanol compound of the general formula (II) or a salt thereof and the phenylacetone derivative of the general formula (VIII) can be carried out by a conventional manner, for instance, using an inert solvent which can be boiled azeotropically with water, removing the water out of the reaction system by means of, for example, a trap means such as Dene-Stark trap. The solvent is not restricted as far as being inert and boiling with water azeotropically, and includes, for instance, organic solvents such as hydrocarbons including aromatic hydrocarbons (e.g. benzene, toluene, xylene, ligroin, petroleum ether, etc.) and aliphatic hydrocarbons (for example, pentane, hexane, heptane, octane, and others) as exemplified in the explanation of the production of the compound of the general formula (IIa).

The dehydrating-condensation may also be conducted by using a solvent, for example, an inert solvent which is capable of boiling with water azeotropically and removing water out of the reaction system with distilling off the solvent. Such solvent includes, for example, organic solvents such as lower alcohols (e.g. a C$_{1-4}$ alcohol such as methanol, ethanol, propyl alcohol, isopropyl alcohol, butanol, t-butanol, etc.) as well as aromatic hydrocarbons and aliphatic hydrocarbons mentioned above.

The reaction may be carried out in the presence of an acid catalyst. As such an acid, acids used in the following one-pot method (2) can be employed.

The ratio of the (R)-2-amino-1-phenylethanol compound of the general formula (II) or a salt thereof relative to the phenylacetone derivative of the general formula (VIII) is usually such that the former/the latter equals about 0.5 to 2.0 (molar ratio) and preferably about 0.8 to 1.2 (molar ratio).

As the reducing agent, there may be mentioned, for example, a metal hydride such as sodium cyanoborohydride and sodium borohydride, hydrogen and others. Hydrogen may usually be employed in combination with a catalyst for catalytic reduction. Use of hydrogen as the reducing agent can render the object (R,R)-1-phenyl-2-[(2-phenyl-1-alkyl-ethyl)amino]ethanol derivative to be produced preferently among the two species of diastereomers by asymmetric induction. The catalyst for catalytic reduction include, for instance, a nickel catalyst such as Raney-nickel catalyst; a platinum group catalyst including a platinum catalyst such as platinum carbon, platinum black, platinum oxide (e.g. Adams catalyst), etc., a palladium catalyst, a rhodium catalyst, a ruthenium catalyst such as ruthenium carbon, ruthenium oxide and ruthenium black, and a rhenium catalyst. These catalysts can be employed singly or in combination. Preferred catalysts, include for example, a platinum catalyst and a ruthenium catalyst. Among them a platinum catalyst, specifically platinum oxide, can advantageously be used.

The amount of the catalyst for catalytic reduction can be selected from a range with regard to the reaction rate and economic factors, and is, generally, about 0.01 to 20 parts by weight, preferably about 0.01 to 10 parts by weight, more preferably about 0.01 to 5 parts by weight (e.g 0.5 to 5 parts by weight), and specifically 0.5 to 3 parts by weight relative to 100 parts by weight of the compound of the general formula (II).

The reaction temperature depends on the species or amount of the raw materials, the species of the catalyst, the pressure condition and other factors, and is usually about 0° to 100° C., preferably about 10° to 80° C. and more preferably about 10° to 60° C. The reaction may be carried out under atmospheric condition or under pressure. The reaction pressure may range, usually, about from 1 to 100 atm, preferably about from 1 to 20 atm. The reaction time may be selected from a shorter time (for example about 10 minutes to 10 hours) under pressure, and about 1 to 48 hours at atmospheric condition.

The hydrogenation can be conducted in an inert solvent. The solvent includes, for instance, organic solvents including alcohols such as $C_{1-4}$ alcohols (e.g. methanol, ethanol, propyl alcohol, isopropyl alcohol, butanol, t-butanol, etc.); aromatic hydrocarbons such as benzene, toluene, xylene, ethylbenzene, petroleum ether, and others; aliphatic hydrocarbons such as pentane, hexane, heptane, octane, and the like; alicyclic hydrocarbons such as cyclohexane, methylcyclohexane, cycloheptane, etc.; halogenated hydrocarbons such as chloroform, dichloromethane, 1,2-dichloroethane and so on; ethers such as diethyl ether, diisopropyl ether, dibutyl ether, dioxane, tetrahydrofuran and the like; esters such as methyl acetate, ethyl acetate, isopropyl acetate and others. Such solvents can be employed independently or in combination.

The explanation of the one-pot method (2) is illustrated hereinbelow. According to the one-pot method (2), the (R,R)-1-phenyl-2-[(2-phenyl-1-alkyl-ethyl)amino]ethanol derivative of the general formula (XI) can be obtained by allowing the (R)-2-amino-1-phenylethanol compound of the general formula (II) or a salt thereof to react with the phenylacetone derivative of the general formula (VIII) and hydrogen in the presence of a catalyst for catalytic reduction.

The reaction may be conducted in the absence of an acid, but the reaction can also be conducted advantageously in the presence of an acid. Hydrogenation in the presence of an acid where the acid acts as a catalyst can increase the conversion ratio of the raw materials to the object compound, thus the object compound can be purified easily or readily. The acid may be whichever of an inorganic acid or an organic acid. The inorganic acid and the organic acid can be referred to the inorganic acids and organic acids including optically active organic acids as exemplified in the explanation of the production of the compound of the general formula (IIa).

As the acid, an acid whereby in the reaction, an adduct having high solubility to the solvent can be selected from the above exemplified acids according to the species of the solvent. Among the inorganic acids, preferred is hydrochloric acid, sulfuric acid, nitric acid, phosphoric acid and boric acid, and typically hydrochloric acid, sulfuric acid and nitric acid. Especially, hydrochloric acid can advantageously be employed. As the organic acid, favorable includes, for instance, a saturated aliphatic monocarboxylic acid, a saturated aliphatic dicarboxylic acid, an unsaturated aliphatic carboxylic acid, a sulfuric acid and the like. More preferred is a saturated aliphatic monocarboxylic acid, a saturated aliphatic dicarboxylic acid, an unsaturated aliphatic carboxylic acid. A $C_{1-4}$ carboxylic acid such as formic acid, acetic acid and propionic acid can advantageously be employed.

The amount of the acid used may be selected from a wide range depending on the reaction rate and other factors, and is, for instance, relative to 100 parts by weight of the compound of the general formula (II), about 0.1 to 80 parts by weight, preferably about 0.1 to 50 parts by weight (e.g. about 0.1 to 10 parts by weight) and more preferably about 0.5 to 10 parts by weight (for instance, about 0.5 to 5 parts by weight).

The hydrogenation in the one-pot method (2) can be carried out with the use of a similar reducing agent, catalyst for catalytic reduction, reaction solvent and others under a similar reaction conditions as in the hydrogenation of the stepwise method (1).

According to the method which comprises a reaction of the compound of the general formula (II) or a salt thereof with the compound of the general formula (VIII) and a reducing reaction of the resultant product, the object compound, that is, the (R,R)-1-phenyl-2-[[2-(phenyl)-1-alkylethyl]amino]ethanol derivative can efficiently be obtained with high selectivity. Further, the (R)-2-amino-1-phenylethanol compound of the general formula (II) and the compound of the general formula (VIII) used as raw materials are both easy to handle or treat and obtainable conveniently. Furthermore, among two of the raw materials, the phenylacetone derivative is not necessary optically active, thus the production process is expedient.

The (R,R)-1-phenyl-2-[[2-(phenyl)-1-alkylethyl]amino]ethanol derivative having high optical purity can easily or readily obtained by subjecting the product (R,R)-1-phenyl-2-[[2-(phenyl)-1-alkylethyl]amino]ethanol derivative of the general formula (XI) to purification, if necessary after adjusting the pH of the reaction mixture, such as extraction with an organic solvent, vacuum concentration, column chromatography, distillation, crystallization and recrystallization.

When the corresponding (R,S)-isomer, that is a compound of the general formula (XIII)

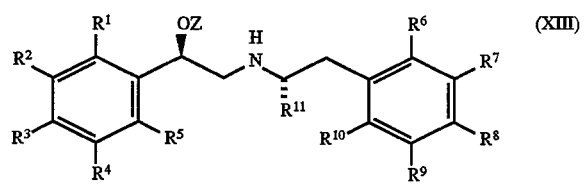

wherein $R^1$, $R^2$, $R^3$, $R^4$, $R^5$, $R^6$, $R^7$, $R^8$, $R^9$, $R^{10}$, $R^{11}$ and Z have the same meanings as defined above, is by-produced, the object (R,R)-isomer can efficiently and selectively be recovered by adding an acid to the reaction products and subjecting the resultant salt to fractional crystallization.

The acid includes an inorganic acid and organic acid. Examples of the inorganic acid and the organic acid include the inorganic acids and the organic acids (including optically active organic acids) as mentioned in the explanation of the production of the compound of the general formula (IIa). The acids can be employed independently or in combination.

Preferred examples of the inorganic acid include hydrochloric acid, and preferred of the organic acid includes, for instance, a carbocyclic carboxylic acid, an amino acid which may be protected on the amino group with a protective group, a sulfonic acid and the like. Utilization of such acid can reduce the content of an impurity, thus the (R,R)-isomer having higher optical purity can be obtained.

In case of a mixture of the compound of the general formula (XI) wherein $R^1$, $R^2$, $R^3$, $R^5$, $R^6$, $R^9$, $R^{10}$ are respectively a hydrogen atom, $R^{11}$ is a methyl group, $R^4$ is chlorine atom, $R^7$ and $R^8$ are respectively a methoxy group, and the corresponding (R,S)-isomer of the general formula (XIII), an organic acid, especially an optionally substituted 2-alkylphenylpropionic acid such as (R)- or (S)-2-(2,5-dimethylphenyl) propionic acid, or a mixture of these enantiomers, and (R)-(−)- or (S)-(+)-2-(2,4,6-trimethylphenyl)propionic acid or a mixture of these enantiomers can advantageously be used. By using these acids, the (R,R)-isomer can selectively be recovered efficiently.

The proportion of the acid may be selected from a broad range depending on the species of the acid, and is, usually, about 0.5 to 2 gram equivalents, preferably about 0.5 to 1.5 gram equivalents and more preferably about 0.5 to 1.3 gram equivalents relative to 1 mole of the total of the (R,R)-isomer of the general formula (XI) and (R,S)-isomer of the general formula (XIII). The acid is frequently used in a proportion of about 0.8 to 1.2 gram equivalents and more preferably about 0.9 to 1.1 gram equivalents relative to 1 mole of the total of the mixture of the (R,R)-isomer and the (R,S)-isomer.

After formation of the salt, if required, a base may be added. As such base, those exemplified in the explanation of the isolation and purification of the 2-amino-1-phenylethanol derivative of the general formula (I) can be employed. Typically preferred examples of the base include a tertiary amine, specifically an aliphatic tertiary amine. A tri-$C_{1-8}$ alkylamine can preferably or advantageously be used among them.

The amount of base to be added may be selected with regard to the amount of the (R,R)-isomer of the general formula (XI) or other factors, and is, for example, relative to 1 mole of the total amount of the (R,R)-isomer and the (R,S)-isomer, about 0.05 to 0.8 gram equivalent, preferably about 0.05 to 0.6 gram equivalent (for instance, about 0.05 to 0.5 gram equivalent) and more preferably about 0.1 to 0.5 gram equivalent.

Probably because the (R,R)-isomer has a higher basicity than the (R,S)-isomer, the addition of a base may render the (R,S)-isomer to be liberated selectively, thus the (R,R)-isomer having high optical purity can be obtained efficiently.

The reaction temperature depends on the species of the (R,R)-isomer and (R,S)-isomer, and the species of the solvent, and crystals of the object compound can be obtained, for example, by heating the mixture to the neighborhood of the boiling point of the solvent to be dissolved, and (a) cooling to room temperature by leaving to cool, or (b) cooling to room temperature to about −10° C. with preventing from formation of an oil. When the melting point of the compound is lower than the boiling point of solvent, formation of the salt may preferably be carried out at a temperature lower than the melting point of the compound.

The formation of the salt and fractional crystallization may be conducted in an inert solvent. As the solvent, there may be mentioned the lower alcohols, aromatic hydrocarbons, aliphatic hydrocarbons, alicyclic hydrocarbons, halogenated hydrocarbons, ethers, esters and others as exemplified in the hydrogenation. Such solvents can be employed separately or in association. Typical examples of the solvent include esters (e.g. ethyl acetate, etc.), lower alcohols (for instance, methanol, ethanol, isopropyl alcohol, and the like), a mixture of an ester and a lower alcohol (for instance, ethyl acetate-methanol mixed solvent, ethyl acetate-ethanol mixed solvent, etc.), a mixture of a lower alcohol and an ether (for example, isopropyl alcohol-diisopropyl ether mixed solvent and the like). Ethyl acetate, isopropyl alcohol, isopropyl alcohol-diisopropyl ether mixed solvent, and others can advantageously be employed.

The (R,R)-1-phenyl-2-[(2-phenyl-1-alkyl-ethyl)amino] ethanol derivative and a salt thereof thus obtained can selectively react with the $\beta_3$-receptor in vivo to decrease or reduce blood sugar significantly and to remarkably restrain or suppress obesity. The pharmacological activity in the (R,R)-isomer is extremely higher than those in the other optical isomers. (R,R)-[disodium 5-[2-[[2-(3-chlorophenyl) -2-hydroxyethyl]amino]propyl]-1,3-benzodioxole-2,2-dicarboxylate]shows, for example, a higher activity than the corresponding (S,S)-form by a factor of 47-(see the above-mentioned U.S. Patent).

When the corresponding (S)-form is used instead of the (R)-2-amino-1-phenylethanol derivative in the reaction, the object compound (R,R)-1-phenyl-2-[(2-phenyl-1-alkyl-ethyl)amino]ethanol derivative can hardly be produced. Further, use of the racemic 2-amino-1-phenylethanol derivative produces the objective compound only with a low yield, and 4 species of optical isomers are produced, thus an isolating process for isolation and removal of a by-produced optical isomers will be complicated.

As described above, the (R)-2-amino-1-phenylethanol derivative used in the present invention a remarkably usable and effective intermediate to selectively obtain the (R,R)-1-phenyl-2-[(2-phenyl-1-alkyl-ethyl)amino]ethanol derivative efficiently with a high yield, thus the (R)-form is remarkably more usable than the corresponding (S)-form and the racemic form.

Further, the (R)-2-amino-1-phenylethanol derivative, differing from the (R)-1-methyl-2-phenylethylamine derivative conventionally used as the intermediate, does not have an antihypnotic or arousal action, therefore is easy to handle or treat and suited for a use in commercial production.

$R^7$, $R^8$ or the both of the compound of the general formula (XI) can be converted from one substituent to another by a conventional manner. As such a manner, for example, (R,R) -1-phenyl-2-[(2-phenyl-1-alkylethyl)amino]ethanol derivative where $R^7$ and $R^8$ are both methoxy groups can easily be converted to the compound where $R^{7a}$ and $R^{8a}$ together form the group shown by the formula (XII) in accordance with a method shown by the following scheme.

In the following scheme, only the moiety of the phenyl group where $R^7$ and $R^8$ are substituted on is illustrated for convenience.

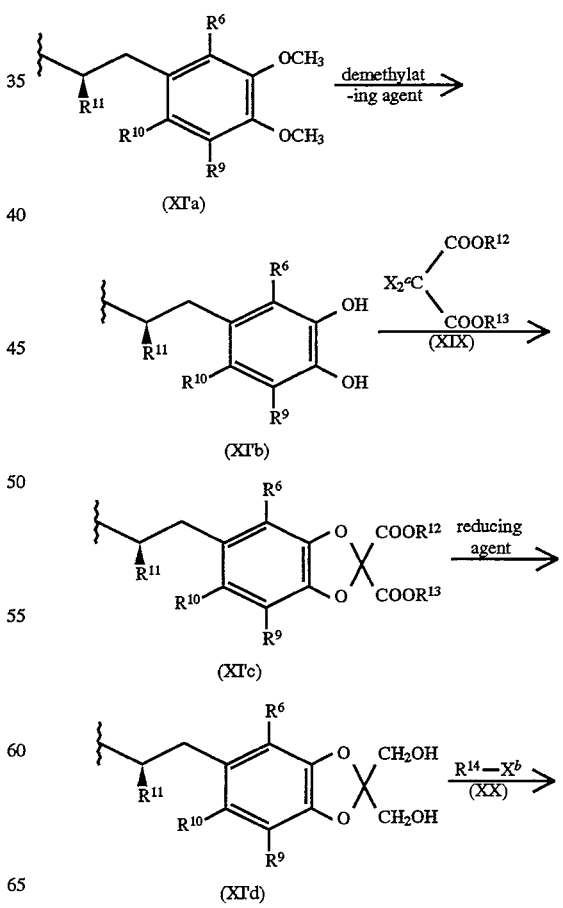

-continued

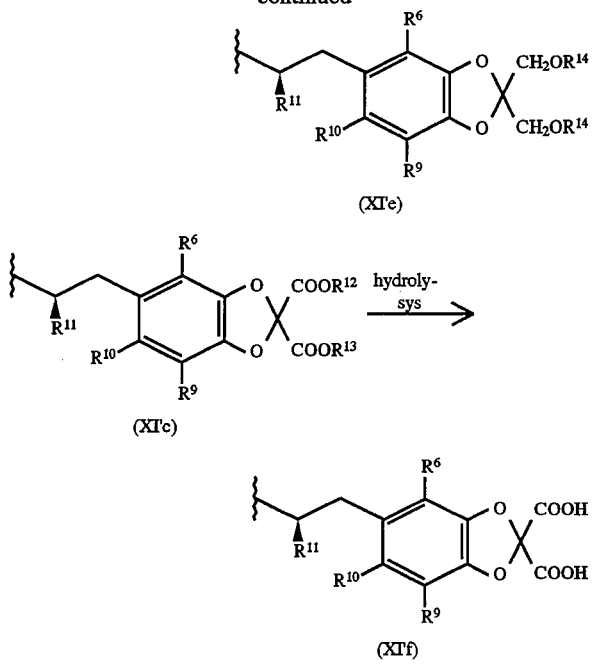

In the scheme, $R^{12}$, $R^{13}$ and $R^{14}$ respectively represent an optionally substituted alkyl group; $X^a$ and $X^b$ separately represent a halogen atom; and $R^6$, $R^9$, $R^{10}$ and $R^{11}$ have the same meanings as defined above.

In the reaction, a compound having a group of the formula (XII) where $R^a$ and $R^b$ are both optionally substituted alkoxycarbonyl groups, can easily be prepared by allowing a demethylating agent such as $BBr_3$ to react with the compound of the general formula (XI'a) where R and $R^2$ are both methyl groups for demethylation, and allowing a dihalomalonic acid ester shown by the formula (XIX) such as diethyl dibromomalonate to react with the demethylated compound in the presence of a base such as potassium carbonate. The resultant compound can be introduced to a compound having the group of the formula (XI'd) where $R^a$ and $R^b$ are both hydroxyl groups by using a reducing agent such as lithium borohydride. When allowing an alkyl halide of the formula (XX) to react with the resulting compound in the presence of a base such as sodium hydride, a compound having the group of the formula (XII) where $R^a$ and $R^b$ are respectively an optionally substituted alkoxymethyl group can be prepared.

Further, hydrolysis of the compound (XI'c) having the group of the formula (XII) where $R^a$ and $R^b$ are respectively an optionally substituted alkoxycarbonyl group, in accordance with a conventional hydrolyzing method such as alkali hydrolysis using an alkali such as an alkali metal hydroxide (e.g. sodium hydroxide) or the like can easily or readily afford a compound having the group of the formula (XII) wherein $R^a$ and $R^b$ are, the same or different, a carboxyl group or a salt thereof.

With regard to the method, the disclosures and descriptions in the above mentioned U.S. Pat. No. 5,061,727 and J. Med. Chem., 35, 3081 (1992) can be referred and incorporated with the present specification.

The (R,R)-1-phenyl-2-[(2-phenyl-1-alkylethyl)amino] ethanol derivative or a salt thereof can advantageously be used, as intact or, where necessary, subjected to a suitable chemical modification, as a medicament such as an anti-obesity agent and an anti-diabetic agent. The processes for such chemical modification may be referred to the descriptions and disclosures in, for example, the above-mentioned U.S. Pat. No. 5,061,727, J. Med. Chem., 35, 3081 (1992) and "Protective groups in Organic Synthesis" (T. W. Greene, A Wiley-Interscience Publication, John Wiley & Sons (1981)).

The production of the (S)-2-amino-1-phenylethanol derivative of the general formula (XV) is illustrated as follows.

As examples and preferred $R^1$ to $R^5$ of the general formula (XV), there may be mentioned the substituents as mentioned above for the general formula (IIa).

Practical examples and preferred examples of the (S)-2-amino-1-phenylethanol derivative of the general formula (XV) include (S)-forms corresponding to the compounds exemplified as the (R)-forms of the general formula (IIa).

The (S)-2-amino-1-phenylethanol derivative of the general formula (XV) can be prepared by a variety of methods, for example, those analogous to the methods mentioned in the (R)-2-amino-1-phenylethanol derivative of the general formula (IIa). The object compound of the formula (XV) can by produced by a chemical synthesis, and can advantageously be produced with the use of an action of a microorganism or a preparation thereof.

For instance, the (S)-form of the formula (XV) can readily and expediently be obtained by, for example, (E) permitting a specific microorganism or a preparation thereof to act on a mixture of enantiomers of the 2-amino-1-phenylethanol compound of the general formula (I) or a salt thereof and harvesting or recovering the product (S)-2-amino-1-phenylethanol compound or a salt thereof (hereinafter referred to as asymmetrically utilization method), or (F) permitting a specific microorganism or a preparation thereof to the compound of the general formula (VII) or a salt thereof to asymmetrically reduce and harvesting or recovering the product optionally active (S)-form or a salt thereof (hereinafter refereed to as asymmetric reduction method).

Hereinbelow, explained is the asymmetrically utilization method (E).

Any strain of microorganism that is capable of acting on a mixture of enantiomers of the 2-amino-1-phenylethanol compound of the general formula (I) or a salt thereof to produce the corresponding (S)-form. Such microorganisms includes, for instance, microorganisms which can selectively utilize the (R)-form among the both enantiomers, and microorganisms which can selectively convert the (R)-form to another compound including the (S)-form, and others.

Examples of such microorganisms include a strain of microorganism belonging to the genus Saccharomyces, the genus Pichia, the genus Schizosaccharomyces, the genus Candida, the genus Hansenula, the genus Yarrowia, the genus Geotrichum, *Micrococcus luteus*, the genus Brevibacterium, the genus Corynebacterium, the genus Xanthomonas, the genus Actinomaqura, the genus Enterobacter, the genus Pseudomonas, the genus Hafnia, the genus Actinoplanes, the genus Escherichia, the genus Bacillus, the genus Listonella, the genus Nosardioides, the genus Amycolata, the genus Aspergillus, the genus Penicillium, the genus Corynespora, the genus Fusarium, the genus Gelasinospora, the genus Helminthosporium, the genus Mortierelia, the genus Neosartorya, the genus Phytophthora, the genus Talaromyces, the genus Scolecobasidium, the genus Rhodococcus and so on.

Practical examples of a strain of microorganism that is capable of acting on a mixture of enantiomers of the compound of the general formula (I) or a salt thereof to produce the corresponding (S)-form include following strains of microorganisms:

(66) the genus Saccharomyces: *Saccharomyces cerevisiae* IFO 0718, *Saccharomyces cerevisiae* IFO 0735, Saccharomyces cerevisiae IFO 0206, etc.,

(67) the genus Pichia: *Pichia fabianii* IFO 1254, etc.

(68) the genus Schizosaccharomyces: *Schizosaccharomyces pombe* IAM 4890, etc.,

(69) the genus Candida: *Candida guilliermondii* IFO 0566, *Candida melibiosica* IFO 10238, etc.,

(70) the genus Hansenula: *Hansenula polymorpha* DSM 70277, etc.,

(71) the genus Yarrowia: *Yarrowia lipolytica* IFO 0746, etc.,

(72) the genus Geotrichum: *Geotrichum capitatum* IFO 0743, *Geotrichum capitatum* IFO 1197, etc.,

(73) Micrococcus luteus: *Micrococcus luteus* IAM 12009, *Micrococcus luteus* IAM 12144, *Micrococcus luteus* IAM 1157, *Micrococcus luteus* IFO 3333, etc.,

(74) the genus Brevibacterium: *Brevibacterium iodinum* IFO 3558, etc.,

(75) the genus Corynebacterium: *Corynebacterium sepedonicum* IFO 3306, etc.,

(76) the genus Xanthomonas: *Xanthomonas sp.* IFO 997, etc.,

(77) the genus Actinomaqura: *Actinomaqura cremea* subsp. *cremea* IFO 14182, etc.,

(78) the genus Enterobacter: *Enterobacter aerogenes* IFO 12010, etc.,

(79) the genus Pseudomonas: *Pseudomonas aeruginosa* IFO 3445, etc.,

(80) the genus Hafnia: *Hafnia alvei* IFO 3731, etc.,

(81) the genus Actinoplanes: *Actinoplanes lobatus* IFO 12513, etc.,

(82) the genus Escherichia: *Escherichia coli* IAM 39, etc.,

(83) the genus Bacillus: *Bacillus licheniformis* BGSC 5A18, etc.,

(84) the genus Listonella: *Listonella anguillarum* IFO 12710, etc.,

(85) the genus Nosardioides: *Nosardioides flavus* IFO 14396, etc.,

(86) the genus Amycolata: *Amycolata autotrophica* IFO 12743, etc.,

(87) the genus Aspergillus: *Aspergillus niger* IFO 4415, *Aspergillus niger* AHU 7115, *Aspergillus ficuum* IFO 4318, *Aspergillus cavdidus* IFO 4389, *Aspergillus oryzae* IFO 4390, *Aspergillus oryzae* var. *brunneus* JCM 2240, *Aspergillus tamarii* IAM 2138, etc.,

(88) the genus Penicillium: *Penicillium chrysogenum* IAM 7142, etc.,

(89) the genus Corynespora: *Corynespora cassiicola* IFO 6724, etc.,

(90) the genus Fusarium: *Fusarium solani* IFO 5232, etc.,

(91) the genus Gelasinospora: *Gelasinospora cerealis* IFO 6759, etc.,

(92) the genus Helminthosporium: *Helminthosporium sigmoideum* var. *irreavl* IFO 5273, etc.,

(93) the genus Mortierelia: *Mortierelia isabellina* IFO 6336, *Mortierelia ramanniana* var. *ramanniana* IFO 7825, etc.,

(94) the genus Neosartorya: *Neosartorya fischeri* var. *spinosa* IFO 5955, etc.,

(95) the genus Phytophthora: *Phytophthora capsici* IFO 8386, etc.,

(96) the genus Talaromyces: *Talaromyces flavus* var. *flavus* IFO 7231, etc.,

(97) the genus Scolecobasidium: *Scolecobasidium terreum* IFO 8854, etc.,

(98) the genus Rhodococcus: *Rhodococcus luteus* JCM 6162, *Rhodococcus erythropolis* JCM 6821, *Rhodococcus erythropolis* JCM 6827, *Rhodococcus globerrulus* IFO 14531, and so on.

These microorganisms can be used singly or in combination. This includes allowing the microorganism or a preparation thereof to act on a mixture of enantiomers of the amino-1-phenylethanol derivative of the general formula (I) to make the ratio of the (S)-form increased among the both enantiomers.

The microorganisms respectively designated by IFO, JCM, ATCC, DSM, IAM, BGSC and AHU numbers are available from the organizations mentioned above.

For producing the optically active (S)-2-amino-1-phenylethanol derivative of the formula (XV), any of wild strains, mutants and recombinant strains which can be obtained by a genetic engineering technique such as cell fusion or gene manipulation can preferably be employed as far as having the above mentioned ability or capability.

The cultivation of the microorganisms, reaction and recovery of the reaction product can be carried out in a similar manner as in the production of the (R)-2-amino-1-phenylethanol derivative of the general formula (IIa).

The asymmetric reduction method (F) is illustrated hereinbelow.

As the microorganism used in the method, any strain of microorganism which is capable of asymmetrically reducing the compound of the general (VII) to produce the corresponding optically active (S)-2-amino-1-phenylethanol derivative of the general formula (XV) can be employed.

Such a microorganism includes, for instance, a strain of microorganism belonging to the genus Botryoascus, the genus Brettanomyces, the genus Candida, the genus Citeromyces, the genus Clavispora, the genus Debaryomyces, the genus Dipodascus, the genus Eremascus, the genus Galactomyces, the genus Geotrichum, the genus Issatchenkia, the genus Kluyveromyces, the genus Kondoa, the genus Lipomyces, the genus Malassezia, the genus Oosporidium, the genus Pachysolen, the genus Pichia, the genus Rhodosporidium, the genus Rhodotorula, the genus Saccharomyces, the genus Saccharomycodes, the genus Saccharomycopsis, the genus Schizoblastosporion, the genus Schizosaccharomyces, the genus Sporidiobolus, the genus Sporobolomyces, the genus Wickerhamiella, the genus Wingea, the genus Zygosaccharomyces, the genus Bacillus, the genus Comamonas, the genus Rhodobacter, the genus Enterococcus, the genus Lactobacillus, the genus Pediococcus, the genus Leuconostoc, the genus Streptococcus and so on.

As practical examples of the microorganism capable of acting on the aminoketone derivative of the general formula (VII) to produce the (S)-2-amino-1-phenylethanol derivative of the general formula (XV), there may be mentioned following strains of microorganisms:

(99) the genus Botryoascus: *Botryoascus synnaedendrus* IFO 1604, etc., (100) the genus Brettanomyces: *Brettanomyces anomalus* IFO 0642, etc., (101) the genus Candida: *Candida albicans* IFO 1856, *Candida beechii* IFO 10229, *Candida ergatensis* IFO 10233, *Candida fusiformata* IFO 10225, *Candida guilliermondii* IFO 0566, *Candida halonitratophila* IFO 1595, *Candida oregonensis* IFO 1980, *Candida peltata* IFO 1853, *Candida parapsilosis* IFO 10305, *Candida sorboxylosa* IFO 1578, etc., (102) the genus Citeromyces: *Citeromyces matritensis* IFO 0954, etc., (103) the genus Clavispora: *Clavispora lusitaniae* IFO 1019, etc., (104) the genus Debaryomyces: *Debaryomyces hansenii* var. *hansenii* IFO 0083, etc., (105) the genus Dipodascus: *Dipodascus ovetensis* IFO 1201, etc., (106) the genus Eremascus: *Eremascus fertilis* IFO 0691, etc., (107) the genus Galactomyces: *Galactomyces reessii* IFO 1112, etc., (108) the genus Geotrichum: *Geotrichum fermentans* CBS 452.83, *Geotrichum candidum* IFO 4601, *Geotrichum capitatum* IFO 1197, *Geotrichum klebahnii* JCM 2171, etc., (109) the genus Issatchenkia: *Issatchenkia scutulata* var. *scutulata* IFO 10069, etc., (110) the genus Kluyveromyces: *Kluyveromyces lactis* IFO 1267, *Kluyveromyces marxianus* var. *bulgaricus* IAM 4829, etc., (111) the genus Kondoa: *Kondoa malvinella* IFO 1935, etc., (112) the genus Lipomyces: *Lipomyces starkeyi* IFO 1289, etc., (113) the genus Malassezia: *Malassezia furfur* IFO 0656, etc., (114) the genus Oosporidium: *Oosporidium margaritiferum* IFO 1208, etc., (115) the genus Pachysolen: *Pachysolen tannophilus* IFO 1007, etc., (116) the genus Pichia: *Pichia farinosa* IFO 1163, *Pichia holstii* IFO 0986, *Pichia subpelliculosa* IFO 0808, *Pichia toletana* IFO 0950, etc., (117) the genus Rhodosporidium: *Rhodosporidium diobovatum* IFO 0688, etc., (118) the genus Rhodotorula: *Rhodotorula glutinis* IFO 0389, *Rhodotorula glutinis* var. *dairenensis* IFO 0415, etc., (119) the genus Saccharomyces: *Saccharomyces kluyveri* IFO 1894, *Saccharomyces paradoxus* IFO 0259, etc., (120) the genus Saccharomycodes: *Saccharomycodes ludwigii* IFO 0798, etc., (121) the genus Saccharomycopsis: *Saccharomycopsis capsularis* IFO 0672, etc., (122) the genus Schizoblastosporion: *Schizoblastosporion kobayasii* IFO 1644, etc., (123) the genus Schizosaccharomyces: *Schizosaccharomyces pombe* IFO 0358, etc., (124) the genus Sporidiobolus: *Sporidiobolus pararoseus* JCM 5350, etc., (125) the genus Sporobolomyces: *Sporobolomyces pararoseus* IFO 0471, *Sporobolomyces salmonicolor* AHU 3982, etc., (126) the genus Wickerhamiella: *Wickerhamiella domercquii* IFO 1857, etc., (127) the genus Wingea: *Wingea robertsii* IFO 1277, etc., (128) the genus Zygosaccharomyces: *Zygosaccharomyces bailii* DSM 70492, *Zygosaccharomyces fermentati* IFO 0021, etc., (129) the genus Bacillus: *Bacilus subtilis* IFO 3037, etc., (130) the genus Comamonas: *Comamonas terrigena* IFO 13299, etc., (131) the genus Rhodobacter: *Rhodobacter sphaeroides* IFO 12203, etc., (132) the genus Enterococcus: *Enterococcus faecalis* NRIC 1142, etc., (133) the genus Lactobacillus: *Lactobacillus lactis* AHU 1059, etc., (134) the genus Pediococcus: *Pediococcus acidilactici* IFO 3076, etc., (135) the genus Leuconostoc: *Leuconostoc mesenteroides* subsp. *dextranicum* NRIC 1085, *Leuconostoc mesenteroides* AHU 1071, *Leuconostoc oenos* DSM 20252, etc., (136) the genus Streptococcus: *Streptpcoccus uberis* NRIC 1153, and so on.

According to this method, any of wild strains, mutants and recombinant strains which can be obtained by a genetic engineering technique such as cell fusion or gene manipulation can suitable be employed so far as having the ability or capability mentioned above.

The microorganisms identified hereinabove by IFO, AHU, DSM, JCM numbers are available from the above organizations. The microorganisms designated by IAM numbers are listed "IAM Catalogue of strains, 1st Ed. (1993) published by the Institute for Research Promotion of Applied Microbiology, and are available from General Center of Microbial Algae, Institute of Applied Microbiology, Tokyo University, Japan.

The microorganism titled by CBS number is listed in "List of cultures FUNGI and YEAST, Ed. 32 (1990)" published by the CENTRAALBUREAU VOOR SCHIMMELCULTURES (CBS) and is available from the same organization. The microorganisms identified by NRIC numbers are described in "Catalogue of Microbial Strains, Ed. 2 (1992)" published by Laboratory of Cell Collection, Tokyo Agricultural University, Japan and are available from the same Laboratory.

For the processes for the cultivation of the microorganism, asymmetric reduction and recovery of the product compound, those in the production of the (R)-2-amino-1-phenylethanol derivative of the general formula (IIa) may be referred to.

Further, the (S)-2-amino-1-phenylethanol derivative of the general formula (XV) can also be prepared by methods similar to the methods (C) and (D) of the production of the (R)-2-amino-1-phenylethanol derivative of the general formula (IIa). Namely, the (S)-form of the general formula (XV) can easily or readily be prepared by utilizing corresponding (S)-form respectively as the compound of the formula (III) or the compound of the formula (IV) as the reactant in the method (C). The (S)-form can readily be isolated from the corresponding (R)-form in the method (D) by, for instance, fractional crystallization.

The (S)-2-amino-1-phenylethanol derivative of the general formula (XV) may be converted to the (R)-2-amino-1-phenylethanol derivative of the formula (IIa) by, for example, subjecting the (S)-form to nucleophilic substitution reaction accompanied with a steric inversion. Such reaction can be conducted with the use of a nucleophilic reagent.

The (S)-2-amino-1-phenylethanol derivative of the general formula (XV) can easily be converted to the (R)-2-amino-1-phenylethanol derivative shown by the general formula (IIa) by selecting an reagent, a catalyst and reaction conditions from a suitable range wherein the reaction is proceeded with steric inversion. For example, the reaction can be carried out in accordance with the following scheme:

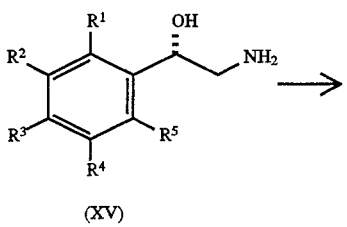

(XV)

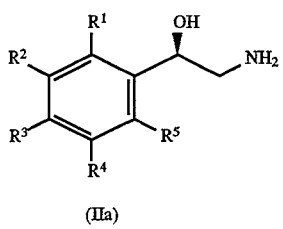

(IIa)

In the general formula (XV), $R^1$, $R^2$, $R^3$, $R^4$ and $R^5$ have the same meanings as defined above.

The conversion of the compound of the general formula (XV) to the compound of the general formula (IIa) can be carried out by, for example, the following method according to Mitsunobu reaction.

The (R)-2-amino-1-phenylethanol derivative can be obtained by allowing an organic acid to react with the compound of the general formula (XV) in the presence of triarylphosphine (e.g. triphenylphosphine, etc.) and an azodicarboxylic acid ester such as ethyl azodicarbonate to form the sterically inverted corresponding organic acid ester, and hydrolyzing the resulting ester. The organic acid includes, for example, formic acid, acetic acid, trichloroacetic acid, trifluoroacetic acid, benzoic acid and the like. The formation of the organic acid ester may be conducted, for example, at a temperature of about −60° to 60° C. The reaction may be carried out in an inert solvent such as an aromatic hydrocarbon (for example, benzene, toluene and so on) and an ether (e.g. tetrahydrofuran, etc.). The proportions of trialkylphosphine, organic acid and azodicarboxylic acid ester based on 1 mole of the compound of the general formula (XV) are respectively about 0.7 to 2.0 moles. The hydrolysis of the organic acid ester can be conducted by a conventional manner such as acid-hydrolysis or alkali-hydrolysis.

Such method utilizing Mitsunobu reaction wherein an optically active alcohol is sterically inverted to the corresponding optically active alcohol may refer to methods or those analogous thereto described, for example, in Synthesis, 1 (1981); Tetrahedron Lett., 1619 (1973); and Bull. Chem. Soc. Jpn., 44, 3427 (1971), and these descriptions can be incorporated into the present specification.

For the conversion of the optically active alcohol to the corresponding enantiomer, following methods can also be applied:

(a) the method comprising esterifying an optically active alcohol to a carboxylic acid ester such as trichloroacetic acid ester, and hydrolyzing the resultant carboxylic acid ester, in a water-ether solvent such as 75% $H_2O$ dioxane, can also be applied (see Chem. Lett., 1976, 893), and (b) the method which comprises (a) converting an optically active alcohol to a sulfonic acid ester such as p-toluenesulfonic acid ester, (b) allowing an organic acid salt such as tetraethylammonium acetate and sodium acetate (and acetic acid) to react with the resulting sulfonic acid ester to sterically invert to the corresponding organic acid ester, and (c) hydrolyzing the resultant organic acid ester (J. Am. Chem. Soc., 87, 3682, (1965); and J. Chem. Soc., 1954, 965).

The obtained (R)-2-amino-1-phenylethanol derivative of the general formula (IIa) is, as described above, an specifically important intermediate for production of the (R,R)-1-phenyl-2-[[2-(phenyl)-1-alkylethyl]amino]ethanol derivative. Accordingly, the (S)-2-amino-1-phenylethanol derivative of the general formula (XV) used in the present invention is remarkably usable as an intermediate for the (R)-2-amino-1-phenylethanol derivative.

The methods for conversion of the (S)-2-amino-1-phenylethanol derivative of the general formula (XV) to the (R)-2-amino-1-phenylethanol derivative of the general formula (IIa) can also be applied to the conversion of the corresponding (R)-form to the (S)-form.

In the each method as described above, where a compound used as a raw material has a hydroxyl group or an amino group, the compound may be subjected to the reaction, if necessary, with being protected on the hydroxyl group or the amino group with a suitable protective group (e.g. the protective group for hydroxyl group, the protective group for amino group as referred to above, and the like).

The following examples are intended to illustrate the invention in further detail and should by no means be construed as delimiting the scope of the invention.

EXAMPLES

The quantitative determination and optical purity determination of product 2-amino-1-phenylethanol derivative in the reaction mixture were carried out, unless specifically mentioned, by subjecting the reaction mixture to high performance liquid chromatography using an optical resolution column (column: Crownpack CR (trade name), Daicel Chemical Industries, Ltd.; mobile phase: perchloric acid buffer (pH 2.0); wavelength: 220 nm; flow rate: 1 ml/min.; column temperature: 40° C.). Under the determination condition, for example, the retention time for (R)-2-amino-1-(3-chlorophenyl)ethanol is 16.8 minutes and (S)-2-amino-1-(3-chlorophenyl)ethanol is 18.5 minutes.

Examples 1 to 100

These Examples pertain to the production of (R)-2-amino-1-(3-chlorophenyl)ethanol.

The following media (1) and (2) were prepared to grow microbial strains.

The medium for the preparation of cells (1), i.e. for yeast and fungi was:

| | |
|---|---|
| Glucose | 2.0% by weight |
| Yeast extract | 0.3% by weight |
| Malt extract | 0.3% by weight |
| Polypeptone | 0.5% by weight |
| Deionized water (pH 6.0) | 96.9% by weight |

The medium for the preparation of cells (2), i.e. for bacterium and actinomyces was:

| | |
|---|---|
| Glucose | 2.0% by weight |
| Yeast extract | 0.5% by weight |
| Meat extract | 0.3% by weight |
| Polypeptone | 0.3% by weight |
| Ammonium sulfate | 0.2% by weight |

| | |
|---|---|
| Potassium primary phosphate | 0.1% by weight |
| Deionized water (pH 7.0) | 96.6% by weight |

A test tube of 21 mm in inner diameter was charged with 5 ml of the above mentioned medium respectively. After sterilization, the tube was inoculated with one of the following microbial strains. A yeast or fungus was inoculated to the Medium (1) and a bacterium or actinomyces was inoculated to the Medium (2) respectively, and the inoculated tube was incubated under shaking at 30° C. for 48 hours. After the incubation, the wet viable cells were isolated by centrifuging.

[Yeasts]

Example 1: *Hansenula anomala* IFO 0707
Example 2: *Geotrichum candidum* IFO 4601
Example 3: *Geotrichum candidum* IFO 4598
Example 4: *Candida albicans* IFO 1594
Example 5: *Candida albicans* IFO 1856
Example 6: *Candida parapsilosis* IFO 1022
Example 7: *Candida gropengiesseri* IFO 0659
Example 8: *Candida aaseri* IFO 10404
Example 9: *Candida beechii* IFO 10229
Example 10: *Candida atmospherica* IFO 1969
Example 11: *Candida natalensis* IFO 1981
Example 12: *Candida paludigena* IFO 10330
Example 13: *Candida sake* IFO 1149
Example 14: *Candida pintolopesii* var. *pintolopesii* IFO 0729
Example 15: *Cryptococcus neoformans* IAM 4788
Example 16: *Rhodosporidium sphaerocarpum* IFO 1438
Example 17: *Rhodosporidium diobovatum* IFO 0688
Example 18: *Rhodotorula rubra* IFO 0406
Example 19: *Rhodotorula rubra* AHU 3948
Example 20: *Rhodotorula glutinis* var. *dairenensis* IFO 0415
Example 21: *Sporobolomyces roseus* IFO 1040
Example 22: *Kluyveromyces marxianus* var. *bulgaricus* IAM 4829
Example 23: *Kluyveromyces lactis* IFO 1267
Example 24: *Issatchenkia scutulata* var. *scutulata* IFO 10069
Example 25: *Issatchenkia scutulata* var. *scutulata* IFO 10070
Example 26: *Pichia thermotolerans* IFO 10024
Example 27: *Pichia farinosa* IFO 1163
Example 28: *Botryoascus synnaedendrus* IFO 1604
Example 29: *Debaryomyces hansenii* var. *hansenii* IFO 0083
Example 30: *Lipomyces starkeyi* IFO 1289
Example 31: *Metschnikowia bicuspidata* IFO 1408
Example 32: *Saccharomycodes ludwigii* IFO 0798
Example 33: *Schizoblastosporion kobayashii* IFO 1644
Example 34: *Stephanoascus ciferrii* IFO 1854
Example 35: *Sterigmatomyces halophilus* IFO 1488
Example 36: *Zygosaccharomyces rouxii* IFO 0510
Example 37: *Zygosaccharomyces rouxii* IAM 4114
Example 38: *Zygosaccharomyces fermentati* IFO 0021
Example 39: *Sporidiobolus salmonicolor* IFO 1845
Example 40: *Sporidiobolus pararoseus* IFO 1107
Example 41: *Malassezia furfur* IFO 0656
Example 42: *Torulaspora delbrueckii* IFO 0955
Example 43: *Saccharomycopsis capsularis* IFO 0672
Example 44: *Leucosporidium scottii* IFO 1923
Example 45: *Leucosporidium scottii* IFO 1924

[Fungi]

Example 46: *Agrocybe cylindracea* IFO 30299
Example 47: *Trichoderma viride* IFO 5720
Example 48: *Alternaria kikuchiana* IFO 5778
Example 49: *Hamigera avellanea* IFO 7721
Example 50: *Moniliella acetoabutans* IFO 9481
Example 51: *Pholiota nameko* IFO 6141
Example 52: *Podospola carbonaria* IFO 30294
Example 53: *Aegerita candida* IFO 6988

[Bacteria and Actinomyces]

Example 54: *Corynebacterium aquaticum* IFO 12154
Example 55: *Corynebacterium mediolanum* JCM 3346
Example 56: *Gluconobacter asaii* IFO 3265
Example 57: *Gluconobacter oxydans* IFO 3255
Example 58: *Gluconobacter oxydans* IFO 3130
Example 59: *Gluconobacter oxydans* IFO 3289
Example 60: *Gluconobacter frateurii* IFO 3271
Example 61: *Promicromonospora citrea* IFO 12397
Example 62: *Pseudomonas aeruginosa* IFO 3899
Example 63: *Pseudomonas riboflavina* IFO 13584
Example 64: *Pseudomonas fluorescens* IFO 3925
Example 65: *Pseudomonas putida* IFO 12996
Example 66: *Pseudomonas syncyanea* IFO 3757
Example 67: *Pseudomonas diminuta* IFO 12697
Example 68: *Pseudomonas chlororaphis* IFO 3522
Example 69: *Pseudomonas fragi* IFO 3458
Example 70: Pseudomonas sp. ATCC 14676
Example 71: *Bordetella bronchiseptica* IFO 13691
Example 72: Acetobacter sp. IFO 3248
Example 73: Acetobacter sp. IFO 3297
Example 74: *Acetobacter pasteurianus* ATCC 10245
Example 75: *Acetobacter pasteurianus* IFO 3259
Example 76: *Acetobacter pasteurianus* IFO 3277
Example 77: *Bacillus subtilis* IFO 3013
Example 78: *Bacillus subtilis* IFO 3009
Example 79: *Bacillus cereus* AHU 1355
Example 80: *Bacillus cereus* AHU 1707
Example 81: *Bacillus cereus* IFO 3001
Example 82: *Bacillus coagulans* IAM 1115
Example 83: *Bacillus brevis* IFO 3331
Example 84: *Bacillus sphaericus* IFO 3525
Example 85: *Agrobacterium radiobacter* IFO 12664
Example 86: *Arthrobacter ureafaciens* IFO 12140
Example 87: *Amauroascus reticulatus* IFO 9196
Example 88: *Brevibacterium linens* IFO 12141
Example 89: *Micrococcus roseus* IFO 3764
Example 90: *Aureobacterium testaceum* IFO 12675
Example 91: *Azotobacter vinelandii* IFO 13581
Example 92: *Xanthomonas campestris* pv *oryzae* IAM Example 93: *Klebsiella pneumoniae* IFO 3317
Example 94: *Comamonas testosteroni* IFO 12048
Example 95: *Comamonas testosteroni* IAM 1048
Example 96: *Mycobacterium diernhoferi* IFO 3707
Example 97: *Terrabacter tumescens* IFO 12960
Example 98: *Streptomyces cinereoruber* HUT 6142
Example 99: *Rhodococcus amidophilus* (IFM 0144)
Example 100: *Rhodococcus equi* JCM 1313

A test tube of 21 mm φ in inner diameter was charged with 1 ml of 0.1M potassium phosphate buffer (pH 7.0), and the wet viable cells obtained above was suspended therein. A racemic 2-amino-1-(3-chlorophenyl)ethanol (5 μl) was added to the suspension and reaction was conducted on a reciprocating shaker at 30 C. for 48 hours.

After completion of the reaction, cells were removed from the reaction mixture by centrifugation, and the supernatant was subjected to high performance liquid chromatography to determine the amount, absolute configuration and optical purity of the obtained optically active 2-amino-1-(3-chlorophenyl)ethanol. The results are set forth in Tables 1 to 5. In the following Tables, the term "amount" means the amount (mg/ml) of the optical active 2-amino-1-(3-chlorophenyl)ethanol contained in the reaction mixture.

TABLE 1

| Example No. | Absolute configuration | Optical purity (% e e) | Amount (mg/ml) |
|---|---|---|---|
| 1 | R | 100 | 0.01 |
| 2 | R | 61 | 0.2 |
| 3 | R | 68 | 0.08 |
| 4 | R | 66 | 1.1 |
| 5 | R | 100 | 0.02 |
| 6 | R | 57 | 0.6 |
| 7 | R | 100 | 0.9 |
| 8 | R | 82 | 0.4 |
| 9 | R | 69 | 0.8 |
| 10 | R | 75 | 1.3 |
| 11 | R | 57 | 0.1 |
| 12 | R | 77 | 0.7 |
| 13 | R | 68 | 1.5 |
| 14 | R | 63 | 0.1 |
| 15 | R | 100 | 0.03 |
| 16 | R | 100 | 1.0 |
| 17 | R | 55 | 1.0 |
| 18 | R | 100 | 0.01 |
| 19 | R | 61 | 0.1 |
| 20 | R | 82 | 0.5 |

TABLE 2

| Example No. | Absolute configuration | Optical purity (% e e) | Amount (mg/ml) |
|---|---|---|---|
| 21 | R | 77 | 1.3 |
| 22 | R | 100 | 0.01 |
| 23 | R | 56 | 1.1 |
| 24 | R | 78 | 1.1 |
| 25 | R | 70 | 1.4 |
| 26 | R | 52 | 1.2 |
| 27 | R | 99 | 0.9 |
| 28 | R | 100 | 1.4 |
| 29 | R | 93 | 0.7 |
| 30 | R | 100 | 0.02 |
| 31 | R | 57 | 1.1 |
| 32 | R | 100 | 0.02 |
| 33 | R | 77 | 0.1 |
| 34 | R | 100 | 0.01 |
| 35 | R | 100 | 1.0 |
| 36 | R | 95 | 0.4 |
| 37 | R | 78 | 0.3 |
| 38 | R | 67 | 0.04 |
| 39 | R | 100 | 0.9 |
| 40 | R | 100 | 1.2 |

TABLE 3

| Example No. | Absolute configuration | Optical purity (% e e) | Amount (mg/ml) |
|---|---|---|---|
| 41 | R | 100 | 0.2 |
| 42 | R | 100 | 0.03 |
| 43 | R | 100 | 0.6 |
| 44 | R | 63 | 1.0 |
| 45 | R | 81 | 0.1 |
| 46 | R | 48 | 0.8 |
| 47 | R | 14 | 0.2 |
| 48 | R | 39 | 0.2 |
| 49 | R | 11 | 0.8 |
| 50 | R | 31 | 0.6 |
| 51 | R | 14 | 0.4 |
| 52 | R | 14 | 0.8 |
| 53 | R | 29 | 2.2 |
| 54 | R | 100 | 0.1 |
| 55 | R | 14 | 1.5 |
| 56 | R | 100 | 2.2 |
| 57 | R | 90 | 1.3 |
| 58 | R | 79 | 1.6 |
| 59 | R | 30 | 3.8 |
| 60 | R | 62 | 2.5 |

TABLE 4

| Example No. | Absolute configuration | Optical purity (% e e) | Amount (mg/ml) |
|---|---|---|---|
| 61 | R | 100 | 0.4 |
| 62 | R | 72 | 1.8 |
| 63 | R | 40 | 1.9 |
| 64 | R | 35 | 2.6 |
| 65 | R | 26 | 1.6 |
| 66 | R | 20 | 2.6 |
| 67 | R | 19 | 2.3 |
| 68 | R | 12 | 2.2 |
| 69 | R | 12 | 3.5 |
| 70 | R | 14 | 2.1 |
| 71 | R | 100 | 0.3 |
| 72 | R | 100 | 1.8 |
| 73 | R | 100 | 1.6 |
| 74 | R | 24 | 3.2 |
| 75 | R | 75 | 2.2 |
| 76 | R | 15 | 4.2 |
| 77 | R | 100 | 0.9 |
| 78 | R | 45 | 1.3 |
| 79 | R | 94 | 1.6 |
| 80 | R | 30 | 2.3 |

TABLE 5

| Example No. | Absolute configuration | Optical purity (% e e) | Amount (mg/ml) |
|---|---|---|---|
| 81 | R | 21 | 2.2 |
| 82 | R | 76 | 1.3 |

TABLE 5-continued

| Example No. | Absolute configuration | Optical purity (% e e) | Amount (mg/ml) |
|---|---|---|---|
| 83 | R | 33 | 1.7 |
| 84 | R | 13 | 1.9 |
| 85 | R | 90 | 1.5 |
| 86 | R | 20 | 1.4 |
| 87 | R | 75 | 0.8 |
| 88 | R | 74 | 3.5 |
| 89 | R | 63 | 2.2 |
| 90 | R | 43 | 0.7 |
| 91 | R | 37 | 1.6 |
| 92 | R | 20 | 3.3 |
| 93 | R | 13 | 5.1 |
| 94 | R | 100 | 1.8 |
| 95 | R | 21 | 2.2 |
| 96 | R | 100 | 0.4 |
| 97 | R | 16 | 1.3 |
| 98 | R | 13 | 1.4 |
| 99 | R | 12 | 2.7 |
| 100 | R | 14 | 3.9 |

Examples 101 to 111

These examples pertain to the production of (R)-2-amino-1-phenylethanol.

A medium for preparation of cells (3) having the following composition was prepared. For yeasts and fungi, the media for preparation of cells (1) used in Examples 1 to 100 was employed.

The medium for the preparation of cells (2), i.e. for bacteria was:

| | |
|---|---|
| Glucose | 2.0% by weight |
| Yeast extract | 0.5% by weight |
| Meat extract | 0.3% by weight |
| Polypeptone | 0.3% by weight |
| Ammonium sulfate | 0.2% by weight |
| Potassium primary phosphate | 0.1% by weight |
| Magnesium sulfate | 0.05% by weight |
| Deionized water (pH 7.0) | 96.55% by weight |

A test tube of inner diameter of 21 mm was charged with 5 ml of the media respectively. After sterilization, the tube was inoculated with one of following microorganism. The medium (1) was used for a yeast and fungus and the medium (3) was employed for a bacterium respectively. The inoculated tube was incubated under shaking at 30° C. for 48 hours.

Example 101: *Candida maltosa* IFO 1977

Example 102: *Candida maltosa* IFO 1978

Example 103: *Lodderomyces elongisporus* IFO 1676

Example 104: *Catenuloplanes japonicus* IFO 14176

Example 105: *Pilimelia terevasa* IFO 14556

Example 106: *Saccharothrix australiensis* IFO 14444

Example 107: *Seratia marcescens* IFO 3735

Example 108: *Enterococcus faecalis* IFO 12964

Example 109: *Lactobacillus casei* subsp. *casei* NRIC 1042

Example 110: *Pediococcus acidilactici* NRIC 1089

Example 111: *Lactococcus lactis* subsp. *lactis* AHU 1089

Cells were collected by centrifuging and a test tube of inner diameter of 21 mm was charged with 1 ml of 0.1M phosphate buffer (pH 7.0) containing 0.5% by weight of aminomethyl phenyl ketone hydrochloride and 5% by weight of glucose. To the charged tube, were suspended the cells and the reaction was carried out on a reciproshaker at 30° C. for 48 hours. After completion of the reaction, the cells were removed off by centrifuging, and the supernatant was submitted to high performance liquid chromatography to determine the amount, the absolute configuration and the optical purity of the product (R)-2-amino-1-phenylethanol. The results are shown in Table 6. In the Table, the term "amount" refers to the amount of the product (R)-2-amino-1-phenylethanol in the reaction mixture.

TABLE 6

| Example No. | Absolute configuration | Optical purity (% e e) | Amount (mg/ml) |
|---|---|---|---|
| 101 | R | 68 | 2.4 |
| 102 | R | 89 | 3.1 |
| 103 | R | 100 | 3.7 |
| 104 | R | 100 | 1.6 |
| 105 | R | 100 | 1.6 |
| 106 | R | 100 | 1.7 |
| 107 | R | 100 | 1.6 |
| 108 | R | 76 | 1.8 |
| 109 | R | 100 | 1.5 |
| 110 | R | 65 | 2.2 |
| 111 | R | 84 | 2.1 |

Examples 112 to 115

These Examples pertain to the production of (R)-2-amino-1-(3-chlorophenyl)ethanol The procedures of cultivation, reaction and determination in Example 101 were repeated, except for using the following strains of microorganisms and using aminomethyl-3-chlorophenyl ketone hydrochloride instead of aminomethyl-phenyl ketone hydrochloride. The proportion, the absolute configuration and the optical purity of the product (R)-2-amino-1-(3-chlorophenyl)ethanol were determined. The results were set forth in Table 7. In the Table, the term "amount" means the amount of (R)-2-amino-1-(3-chlorophenyl)ethanol in the reaction mixture (mg/ml).

Example 112: *Lodderomyces elongisporus* IFO 1676

Example 113: *Candida maltosa* IFO 1978

Example 114: *Candida maltosa* IFO 1977

Example 115: *Pilimelia terevasa* IFO 14556

TABLE 7

| Example No. | Absolute configuration | Optical purity (% e e) | Amount (mg/ml) |
|---|---|---|---|
| 112 | R | 100 | 2.3 |
| 113 | R | 100 | 2.3 |
| 114 | R | 100 | 1.9 |
| 115 | R | 95 | 1.3 |

Examples 116 to 118

These examples pertain to the production of (R)-2-amino-1-(3,4-dihydroxyphenyl)ethanol.

The procedures for cultivation, reaction and analysis were conducted in the same manner as in Example 101, except for using the following strains of microorganisms respectively, and using aminomethyl-3,4-dihydroxyphenyl ketone hydrochloride instead of aminomethyl phenyl ketone hydrochloride to determine the proportion, the absolute configuration and the optical purity of the product (R)-2-amino-1-(3,4-dihydroxyphenyl)ethanol. The results are shown in Table 8. In the Table 8, the term "amount" means the amount of the (R)-2-amino-1-(3,4-dihydroxyphenyl)ethanol in the reaction mixture (mg/ml).

Example 116: *Lodderomyces elongisporus* IFO 1676
Example 117: *Candida maltosa* IFO 1977
Example 118: *Candida maltosa* IFO 1978

TABLE 8

| Example No. | Absolute configuration | Optical purity (% e e) | Amount (mg/ml) |
|---|---|---|---|
| 116 | R | 100 | 1.9 |
| 117 | R | 100 | 1.7 |
| 118 | R | 100 | 2.1 |

Example 119

This Example pertains tot he production of (R)-2-amino-1-(3-chlorophenyl)ethanol.

A 2.6-liter jar fermenter was charged with 1.5 liter of GY medium containing 2.4% by weight of glucose, 1.8% by weight of yeast extract, 0.2% by weight of ammonium sulfate, 0.1% by weight of potassium primary phosphate, 15 ppm of ferrous sulfate heptahydrate, 15 ppm of zinc sulfate heptahydrate. After sterilized by an autoclave, the jar fermenter was inoculated with *Candida maltosa* IFO 1978. The inoculated jar fermenter was incubated at pH 6.0, at 30° C., under aeration at 1 vvm, with stirring at a rate of 400 rpm for 24 hours.

After completion of incubation, the cells were collected and suspended to 1 liter of 0.1M phosphate buffer (pH 6.5) charged in a 2.6-liter jar fermenter. To the mixture, was added 20 g of aminomethyl-3-chloro-phenyl ketone and 50 g of glucose, and the reaction was carried out at 30° C., without aeration, and stirring at a rate of 200 rpm for 48 hours. In the course of the reaction, the pH of the reaction mixture was adjusted at 6.5 with the use of an 20% aqueous solution of sodium hydroxide. On the way of the reaction, according to the analysis of the reaction mixture, (R)-2-amino-1-(3-chlorophenyl)ethanol was produced in a concentration of 13.2 g per liter.

After completion of the reaction, the reaction mixture was acidified to pH 2 or less by using a concentrated hydrochloric acid, and the cells were removed off by centrifugation. The obtained supernatant was subjected to dehydration-concentration with using a vacuum rotary evaporator at a bath-temperature of 50° C. The resultant concentrated was adjusted to pH 9.0 by adding a 20% aqueous solution of sodium hydroxide and was added with 50 g of sodium chloride and extracted three times with 300 ml of methylene chloride. The methylene chloride extract was dried over anhydrous sodium sulfate and the solvent was removed off under reduced pressure to obtain 9.8 g of an oily substance. The optical purity of the obtained (R)-2-amino-1-(3-chlorophenyl)ethanol was 100% e e by the analysis with high performance liquid chromatography using an optical resolution column [column: product of Daicel Chemical Industries, Ltd., Crownpack CR (+) (trade name)]

In the following Examples 120 to 172, the determination of optical purity of the obtained (R,R)-1-phenyl-2-[(2-phenyl-1-alkyl-ethyl)amino]ethanol derivative or a salt thereof was carried out with high performance liquid chromatography using an optical resoluting column (column: manufactured by Daicel Chemical Industries, Ltd., Chiralpack AD (trade name); solvent: n-hexane/2-propanol/diethylamine=90/10/0.1; flow rate: 0.5 ml/minute; temperature: 25° C.; wavelength: 230 nm).

Example 120

Example 120 to the production of (R,R)-1-(3-chlorophenyl)-2-[3,4-dimethoxyphenyl)-1-methylethyl]amino]ethanol.

To 5.83 g of methyl=3,4-dimethoxyphenylmethyl=ketone, 5.15 g of (R)-2-amino-1-(3-chlorophenyl)ethanol and 50 mg of platinum oxide, were added 15 ml of isopropyl alcohol, 30 ml of diisopropyl ether and 2 drops of acetic acid. The mixture was subjected to reduction at room temperature and at 1 atm under hydrogen atmosphere for 24 hours. After completion of the reaction, platinum oxide was removed off by filtration and the solvent was distilled off under reduced pressure to obtain 8.43 g of white oil of (R,R)-1-(3-chlorophenyl)-2-[[2-(3,4-dimethoxyphenyl)-1-methylethyl]amino]ethanol (yield: 80.3%). The optical purity of the obtained (R,R)-isomer was 80%.

Example 121 to 128

These Examples relate to the production of (R,R)-1-(3-chlorophenyl)-2-[[2-(3,3-dimethoxyphenyl)-1-methyl]aminoethanol (R,R)-1-(3-Chlorophenyl)-2-[[2-(3,4-dimethoxyphenyl)-1-methylethyl]amino]ethanol was obtained in the same manner as in Example 120 except for using 0.344 g of methyl=3,4-dimethoxyphenylmethyl=ketone, 0.304 g of (R)-2-amino-1-(3-chlorophenyl)ethanol, 50 mg of platinum oxide and 10 ml of a solvent. The solvent, the yield and the optical purity of the (R,R)-isomer are set forth in Table 9. In the following Tables 9 to 13, the term "OMe" means a methoxy group, the term "Me" refers to a methyl group, the term "NHAc" means an amino group substituted with an acetyl group, and the term "PTsOH" refers to p-toluenesulfonic acid. The term "optical purity" refers to the optical purity of the (R,R)-isomer.

TABLE 9

| Example No. | Solvent used | Yield (%) | Optical purity (%) |
|---|---|---|---|
| 121 | Methanol | 73 | 75 |
| 122 | Ethanol | 74 | 75 |
| 123 | Isopropyl alcohol | 70 | 74 |
| 124 | Toluene-methanol | 78 | 72 |
| 125 | Toluene | 58 | 73 |
| 126 | Tetrahydrofuran | 63 | 74 |
| 127 | Acetonitrile | 50 | 68 |
| 128 | Ethyl acetate | 55 | 70 |

Example 129 to 141

Examples 129 to 141 describe the production of (R,R(-1-phenyl-2-[[2-(phenyl)-1-alkylethyl]amino]ethanol derivatives.

The procedures of Example 120 were repeated to obtain an (R,R)-1-phenyl-2-[(2-phenyl-1-alkylethyl)amino]ethanol derivative except for using platinum oxide as the catalyst for catalytic reduction, isopropyl alcohol-diisopropyl ether (1:2) as the solvent, acetic acid as the acid, and the compounds shown in Table 10 as the raw materials. The raw materials, the yields, the optical purity of the (R,R)-isomer were set forth in Table 10.

TABLE 10

| Example No. | $R^1$ | $R^2$ | $R^3$ | $R^4$ | $R^5$ | Z | $R^6$ | $R^7$ | $R^8$ | $R^9$ | $R^{10}$ | $R^{11}$ | Yield (%) | Optical purity (%) |
|---|---|---|---|---|---|---|---|---|---|---|---|---|---|---|
| 129 | H | H | H | H | H | H | H | H | H | H | H | Me | 80 | 75 |
| 130 | H | H | H | H | H | H | H | OMe | OMe | H | H | Me | 82 | 75 |
| 131 | H | H | H | H | H | H | H | OH | OH | H | H | Me | 78 | 75 |
| 132 | H | $CF_3$ | H | H | H | H | H | H | H | H | H | Me | 84 | 80 |
| 133 | H | H | Cl | H | H | H | H | H | H | H | H | Me | 83 | 78 |
| 134 | H | H | Cl | H | H | H | H | OMe | OMe | H | H | Me | 85 | 78 |
| 135 | H | Cl | Cl | H | H | H | H | H | H | H | H | Me | 80 | 79 |
| 136 | H | Cl | Cl | H | H | H | H | OMe | OMe | H | H | Me | 82 | 79 |
| 137 | H | OMe | H | H | H | H | H | OMe | OMe | H | H | Me | 80 | 78 |
| 138 | H | OMe | H | H | H | H | H | H | H | H | H | Me | 78 | 78 |
| 139 | H | NHAc | OMe | H | H | H | H | OMe | OMe | H | H | Me | 81 | 82 |
| 140 | H | H | $CF_3$ | H | H | H | H | H | H | H | H | Me | 77 | 83 |
| 141 | H | H | $CF_3$ | H | H | H | H | OMe | OMe | H | H | Me | 82 | 80 |

Example 142

This Example describes the production of (R,R)-1-(3-chlorophenyl)-2-[[2-(3,4-dimethoxyphenyl)-1-methylethyl]amino]ethanol.

142 by using isopropyl alcohol-diisopropyl ether (1:2) as the solvent, and the raw materials and the catalysts for catalytic reduction are set forth in Table 11. The raw materials, the catalysts for catalytic reduction, yields and the optical purity of the (R,R)-isomers are shown in Table 11.

TABLE 11

| Example No. | $R^1$ | $R^2$ | $R^3$ | $R^4$ | $R^5$ | Z | $R^6$ | $R^7$ | $R^8$ | $R^9$ | $R^{10}$ | $R^{11}$ | Catalyst | Yield (%) | Optical purity (%) |
|---|---|---|---|---|---|---|---|---|---|---|---|---|---|---|---|
| 143 | H | Cl | H | H | H | H | H | OMe | OMe | H | H | Me | Pt—C | 75 | 80 |
| 144 | H | H | H | H | H | H | H | OMe | OMe | H | H | Me | Platinum oxide | 85 | 78 |
| 145 | H | H | H | H | H | H | H | OMe | OMe | H | H | Me | Pt—C | 76 | 77 |
| 146 | H | H | H | H | H | H | H | H | H | H | H | Me | Platinum oxide | 82 | 75 |
| 147 | H | H | H | H | H | H | H | H | H | H | H | Me | Pt—C | 74 | 72 |
| 148 | H | H | H | H | H | H | H | H | H | H | H | Me | Pd—C | 60 | 70 |
| 149 | H | H | H | H | H | H | H | H | H | H | H | Me | Ru | 65 | 73 |
| 150 | H | H | H | H | H | H | H | H | H | H | H | Me | Rh | 77 | 77 |

To 40 ml of benzene solution of (R)-2-amino-1-(3-chlorophenyl)ethanol (0.304 g), was added 0.344 g of methyl=3,4-dimethoxyphenylmethyl=ketone. The mixture was refluxed in an apparatus equipped with a water-trap for one hour and the water produced was removed from the reaction system. After cooling the reaction mixture, the solvent was distilled off under reduced pressure, and the residue was dissolved into 10 ml of methanol. To the mixture was added platinum oxide, and the reducing reaction was conducted at room temperature at 1 atm pressure under hydrogen atmosphere for 24 hours. After removing off platinum oxide by filtration, the solvent was distilled off under reduced pressure to give 0.501 g of white oil of (R,R)-1-(3-chlorophenyl)-2-[[2-(3,4-dimethoxyphenyl)-1-methylethyl]amino]ethanol (yield 81.0%). The optical purity of the (R,R)-isomer was 80%.

Examples 143 to 150

These Examples described the production of (R,R)-1-phenyl-2-[[2-(phenyl)-1-alkylethyl]amino]ethanol derivatives.

(R,R)-1-Phenyl-2-[(2-phenyl-1-alkylethyl)amino]ethanol derivatives were obtained in the same manner as in Example Example 151

This Example describes the production of (R,R)-1-(3-chlorophenyl)-2-[[2-(3,4-dimethoxyphenyl)-1-methylethyl]amino]ethanol.

To 12.36 g of (R,R)-1-(3-chlorophenyl)-2-[[2-(3,4-dimethoxyphenyl)-1-methylethyl]amino]ethanol having an optical purity of 89%, was added toluene solution of hydrogen chloride to obtain a hydrochloride of the titled compound, and the solvent was distilled off under reduced pressure to give an oil. The oil was subjected to recrystallization by using a mixture of isopropyl alcohol and diisopropyl ether to give 7.57 g of white powder. A mixture of a 10% sodium hydroxide/ethyl acetate was added to the powder and the solvent was distilled off to give (R,R)-1-(3-chlorophenyl)-2-[[2-(3,4-dimethoxyphenyl)-1-methylethyl]amino]ethanol (7.58 g, optical purity 98%).

Example 152

This Example describes the production of (R,R)-1-(3-chlorophenyl)-2-[[2-(3,4-dimethoxyphenyl)-1-methylethyl]amino]ethanol.

To 1 ml of isopropyl alcohol was added 0.103 g of (R,R)-1-(3-chlorophenyl)-2-[[2-(3,4-dimethoxyphenyl)-1-methylethyl]amino]ethanol having an optical purity of 64% to be dissolved, and 0.057 g of (R)-(−)-2-(2,4,6-trimethylphenyl)propionic acid and 2 ml of diisopropyl ether were added to the solution successively to give 0.102 g of white powder. To the powder was added 10% sodium hydroxide/ethyl acetate, and the solvent was distilled off to afford 0.065 g of (R,R)-1-(3-chlorophenyl)-2-[[2-(3,4-dimethoxyphenyl)-1-methylethyl]amino]ethanol having an optical purity of 92%.

Example 152

This Example describes the production of (R,R)-1-(3-chlorophenyl)-2-[[2-(3,4-dimethoxyphenyl)-1-methylethyl]amino]ethanol.

To 1 ml of isopropyl alcohol was added 0.103 g of (R,R)-1-(3-chlorophenyl)-2-[[2-(3,4-dimethoxyphenyl)-1-methylethyl]amino]ethanol having an optical purity of 64% to be dissolved and 0.056 g of (S)-2-(2,5-dimethylphenyl)propionic acid and 4 ml of diisopropyl ether were added to the solution successively to give 0.046 g of white powder. A mixture of 10% sodium hydroxide/ethyl acetate was added to the white powder and the solvent was distilled off to yield 0.030 g of (R,R)-1-(3-chlorophenyl)-2-[[2-(3,4-dimethoxyphenyl)-1-methylethyl]amino]ethanol having an optical purity of 99.4%.

Examples 154 to 168

These Examples describe the production of (R,R)-1-phenyl-2-[(2-phenyl-1-alkylethyl)amino]ethanol derivatives.

The procedures of Example 153 were repeated except that isopropyl alcohol-diisopropyl ether (1:2) was used as the solvent and the raw materials and the acids shown in Table 12 were employed to give (R,R)-1-phenyl-2-[(2-phenyl-1-alkyl-ethyl)amino]ethanol derivatives. The optical purity of the raw materials was 65%. The optical purity of the (R,R)-isomer thus obtained was set forth in Table 12.

Example 169

This Example describes the production of (R,R)-1-3-chlorophenyl)-2-[[2-(3,4-dimethoxyphenyl)-1-methylethyl]amino]ethanol.

To (R,R)-1-(3-chlorophenyl)-2-[[2-(3,4-dimethoxyphenyl)-1-methylethyl]amino]ethanol (1.05 g) having an optical purity of 65% was added a toluene solution of hydrogen chloride to give a hydrochloride, and the solvent was distilled off under reduced pressure to afford an oily substance. Triethylamine (0.15 g) was added to the obtained oily substance, and the mixture was subjected to recrystallization with the use of a mixture of isopropyl alcohol and diisopropyl ether to give 0.80 g of white powder. To the white powder was added 10% sodium hydroxide/ethyl acetate, and the solvent was distilled off to afford 0.70 g of (R,R)-1-(3-chlorophenyl)-2-[[2-(3,4-dimethoxyphenyl)-1-methylethyl]amino]ethanol (optical purity 90%).

Examples 170 to 171

These Examples describe the production of (R,R)-1-phenyl-2-[(2-phenyl-1-alkylethyl)amino]ethanol derivatives.

(R,R)-1-phenyl-2-[(2-phenyl-1-alkyl-ethyl)amino] ethanol derivatives were obtained in the same manner as in Example 169 by using isopropyl alcohol-diisopropyl ether (1:2) as the solvent, and the acids and bases shown in Table 13 as the acids and bases. The raw materials, the acids, the bases and the optical purity of the product (R,R)-isomer are set forth in Table 13. The optical purity of the raw material was 65%. In the Table, the term "HCl" means hydrochloric acid.

TABLE 12

| Example No. | $R^1$ | $R^2$ | $R^3$ | $R^4$ | $R^5$ | Z | $R^6$ | $R^7$ | $R^8$ | $R^9$ | $R^{10}$ | $R^{11}$ | Acid | Optical purity (%) |
|---|---|---|---|---|---|---|---|---|---|---|---|---|---|---|
| 154 | H | Cl | H | H | H | H | H | OMe | OMe | H | H | Me | Hydrochloric acid | 85 |
| 155 | H | Cl | H | H | H | H | H | OMe | OMe | H | H | Me | Acetic acid | 85 |
| 156 | H | Cl | H | H | H | H | H | OMe | OMe | H | H | Me | Benzoic acid | 80 |
| 157 | H | Cl | H | H | H | H | H | OMe | OMe | H | H | Me | Oxalic acid | 82 |
| 158 | H | Cl | H | H | H | H | H | OMe | OMe | H | H | Me | 3,5-Dimethylbenzoic acid | 85 |
| 159 | H | Cl | H | H | H | H | H | OMe | OMe | H | H | Me | o-Toluic acid | 88 |
| 160 | H | Cl | H | H | H | H | H | OMe | OMe | H | H | Me | m-Toluic acid | 88 |
| 161 | H | Cl | H | H | H | H | H | OMe | OMe | H | H | Me | pTsOH | 95 |
| 162 | H | H | H | H | H | H | H | OMe | OMe | H | H | Me | Hydrochloric acid | 80 |
| 163 | H | H | H | H | H | H | H | H | H | H | H | Me | Hydrochloric acid | 83 |
| 164 | H | $CF_3$ | H | H | H | H | H | H | H | H | H | Me | Hydrochloric acid | 82 |
| 165 | H | OMe | H | H | H | H | H | H | H | H | H | Me | Hydrochloric acid | 83 |
| 166 | H | H | $CF_3$ | H | H | H | H | OMe | OMe | H | H | Me | Hydrochloric acid | 80 |
| 167 | H | Cl | H | H | H | H | H | H | H | H | H | Me | Hydrochloric acid | 83 |
| 168 | H | Cl | H | H | H | H | H | H | H | H | H | Me | Hydrochloric acid | 80 |

TABLE 13

| Example No. | R¹ | R² | R³ | R⁴ | R⁵ | Z | R⁶ | R⁷ | R⁸ | R⁹ | R¹⁰ | R¹¹ | Acid | Base | Optical purity (%) |
|---|---|---|---|---|---|---|---|---|---|---|---|---|---|---|---|
| 170 | H | H | H | H | H | H | H | OMe | OMe | H | H | Me | HCl | Triethylamine | 88 |
| 171 | H | Cl | H | H | H | H | H | OMe | OMe | H | H | Me | Acetic acid | Triethylamine | 85 |

Example 172

This Example describes the production of (R,R)-1-(3-chlorophenyl)-2-[[2-(3,4-dimethoxyphenyl)-1-methylethyl]amino]ethanol.

To a mixture of 5.83 g of methyl-3,4-dimethoxyphenylmethyl ketone, 5.15 g of (R)-2-amino-1-(3-chlorophenyl)ethanol and 50 mg of platinum oxide were added 15 ml of isopropyl alcohol and 30 ml of diisopropyl ether, and the reducing reaction was carried out at room temperature, at 1 atm under hydrogen atmosphere for 24 hours. After removing off platinum oxide by filtration, the solvent was distilled off under reduced pressure to give 6.51 g of white oil of (R,R)-1-(3-chlorophenyl)-2-[[2-(3,4-dimethoxyphenyl)1-methylethyl]amino]ethanol (yield 62%). The optical purity of the (R,R)-isomer was 65%.

Examples 173 to 222

These Examples describe the production of (S)-2-amino-1-(3-chlorophenyl)ethanol.

(S)-2-Amino-1-(3-chlorophenyl)ethanol was produced in the similar manner as in Examples 1 to 100, except that the following strains of microorganisms were used respectively.

The results of determination of the amount, the absolute configuration and the optical purity of the obtained (S)-2-amino-1-phenylethanol are shown in Tables 14 to 16. In the Tables 14 to 16, the term "amount" means the amount (mg/ml) of (S)-2-amino-1-(3-chlorophenyl)ethanol in the reaction mixture.

[Yeasts]

Example 173: *Saccharomyces cerevisiae* IFO 0718
Example 174: *Saccharomyces cerevisiae* IFO 0735
Example 175: *Saccharomyces cerevisiae* IFO 0206
Example 176: *Pichia fabianii* IFO 1254
Example 177: *Schizosaccharomyces pombe* IAM 4890
Example 178: *Candida guilliermondii* IFO 0566
Example 179: *Candida melibiosica* IFO 10238
Example 180: *Hansenula polymorpha* DSM 70277
Example 181: *Yarrowia lipolytica* IFO 0746
Example 182: *Geotrichum capitatum* IFO 0743
Example 183: *Geotrichum capitatum* IFO 1197

[Fungi]

Example 184: *Aspergillus niger* IFO 4415
Example 185: *Aspergillus niger* AHU 7115
Example 186: *Aspergillus ficuum* IFO 4318
Example 187: *Aspergillus cavdidus* IFO 4389
Example 188: *Aspergillus oryzae* IFO 4390
Example 189: *Aspergillus oryzae* var. *brunneus* JCM 2240
Example 190: *Aspergillus tamarii* IAM 2138
Example 191: *Penicillium chrysogenum* IAM 7142
Example 192: *Corynespora cassiicola* IFO 6724
Example 193: *Fusarium solani* IFO 5232
Example 194: *Gelasinospora cerealis* IFO 6759
Example 195: *Helminthosporium sigmoideum* var. irreavl IFO 5273
Example 196: *Mortierelia isabellina* IFO 6336
Example 197: *Mortierelia ramanniana* var. *ramanniana* IFO 7825
Example 198: *Neosartorya fischeri* var. *spinosa* IFO
Example 199: *Phytophthora capsici* IFO 8386
Example 200: *Talaromyces flavus* var. *flavus* IFO 7231
Example 201: *Scolecobasidium terreum* IFO 8854

[Bacteria & Actinomyces]

Example 202: *Micrococcus luteus* IAM 12009
Example 203: *Micrococcus luteus* IAM 12144
Example 204: *Micrococcus luteus* IAM 1157
Example 205: *Micrococcus luteus* IFO 3333
Example 206: *Brevibacterium iodinum* IFO 3558
Example 207: *Corynebacterium sepedonicum* IFO 3306
Example 208: *Xanthomonas* sp. IFO 12997
Example 209: *Actinomaqura cremea* subsp. *cremea* IFO 14182
Example 210: *Enterobacter aerogenes* IFO 12010
Example 211: *Pseudomonas aeruginosa* IFO 3445
Example 212: *Hafnia alvei* IFO 3731
Example 213: *Actinoplanes lobatus* IFO 12513
Example 214: *Escherichia coli* IAM 1239
Example 215: *Bacillus licheniformis* BGSC 5A18
Example 216: *Listonella anguillarum* IFO 12710
Example 217: *Nosardioides flavus* IFO 14396
Example 218: *Amycolata autotrophica* IFO 12743
Example 219: *Rhodococcus luteus* JCM 6162
Example 220: *Rhodococcus erythropolis* JCM 6821
Example 221: *Rhodococcus erythropolis* JCM 6827
Example 222: *Rhodococcus globerrulus* IFO 14531

TABLE 14

| Example No. | Absolute configuration | Optical purity (% e e) | Amount (mg/ml) |
|---|---|---|---|
| 173 | S | 59 | 0.3 |
| 174 | S | 100 | 0.1 |
| 175 | S | 54 | 0.5 |
| 176 | S | 69 | 0.9 |
| 177 | S | 70 | 0.3 |
| 178 | S | 67 | 0.05 |
| 179 | S | 78 | 0.1 |
| 180 | S | 66 | 0.4 |
| 181 | S | 100 | 0.04 |
| 182 | S | 100 | 0.2 |
| 183 | S | 73 | 0.5 |
| 184 | S | 21 | 0.8 |
| 185 | S | 64 | 0.3 |
| 186 | S | 57 | 0.6 |
| 187 | S | 19 | 0.8 |
| 188 | S | 22 | 0.7 |

TABLE 14-continued

| Example No. | Absolute configuration | Optical purity (% e e) | Amount (mg/ml) |
|---|---|---|---|
| 189 | S | 24 | 1.0 |
| 190 | S | 57 | 0.5 |
| 191 | S | 17 | 0.6 |
| 192 | S | 14 | 0.5 |

TABLE 15

| Example No. | Absolute configuration | Optical purity (% e e) | Amount (mg/ml) |
|---|---|---|---|
| 193 | S | 52 | 0.7 |
| 194 | S | 38 | 0.4 |
| 195 | S | 72 | 0.4 |
| 196 | S | 31 | 0.8 |
| 197 | S | 61 | 0.9 |
| 198 | S | 10 | 1.0 |
| 199 | S | 24 | 0.8 |
| 200 | S | 13 | 0.2 |
| 201 | S | 20 | 0.8 |
| 202 | S | 97 | 1.0 |
| 203 | S | 34 | 5.5 |
| 204 | S | 31 | 5.2 |
| 205 | S | 55 | 1.0 |
| 206 | S | 75 | 1.4 |
| 207 | S | 64 | 1.8 |
| 208 | S | 53 | 1.6 |
| 209 | S | 47 | 1.1 |
| 210 | S | 41 | 1.1 |
| 211 | S | 12 | 6.2 |
| 212 | S | 13 | 3.2 |

TABLE 16

| Example No. | Absolute configuration | Optical purity (% e e) | Amount (mg/ml) |
|---|---|---|---|
| 213 | S | 13 | 0.9 |
| 214 | S | 13 | 2.2 |
| 215 | S | 12 | 2.9 |
| 216 | S | 12 | 6.2 |
| 217 | S | 11 | 1.4 |
| 218 | S | 10 | 1.4 |
| 219 | S | 28 | 2.5 |
| 220 | S | 47 | 1.8 |
| 221 | S | 40 | 2.2 |
| 222 | S | 48 | 1.8 |

Examples 223 to 282

These Examples describe the production of (S)-2-amino-1-phenylethanol.

A test tube of 21 mm in inner diameter was charged with 5 ml of YM medium containing 2.0% by weight of glucose, 0.3% by weight of yeast extract, 0.3% by weight of malt extract and 0.5% by weight of polypeptone (pH 6.0) for yeast or fungus, or 5 ml of PM medium containing 2.0% by weight of glucose, 0.5% by weight of yeast extract, 0.3% by weight of meat extract, 0.3% by weight of polypeptone, 0.2% by weight of ammonium sulfate, 0.1% by weight of potassium phosphate and 0.05% by weight of magnesium sulfate (pH 7.0). After sterilization, the tube was respectively inoculated with one of the following strains of microorganisms. The inoculated tube was incubated under shaking at 30° C. for 48 hours.

[Yeasts and fungi]

Example 223: *Botryoascus synnaedendrus* IFO 1604
Example 224: *Brettanomyces anomalus* IFO 0642
Example 225: *Candida albicans* IFO 1856
Example 226: *Candida beechii* IFO 10229
Example 227: *Candida ergatensis* IFO 10233
Example 228: *Candida fusiformata* IFO 10225
Example 229: *Candida guilliermondii* IFO 0566
Example 230: *Candida halonitratophila* IFO 1595
Example 231: *Candida oregonensis* IFO 1980
Example 232: *Candida peltata* IFO 1853
Example 233: *Candida parapsilosis* IFO 10305
Example 234: *Candida sorboxylosa* IFO 1578
Example 235: *Citeromyces matritensis* IFO 0954
Example 236: *Clavispora lusitaniae* IFO 1019
Example 237: *Debaryomyces hansenii* var. hansenii IFO 0083
Example 238: *Dipodascus ovetensis* IFO 1201
Example 239: *Eremascus fertilis* IFO 0691
Example 240: *Galactomyces reessii* IFO 1112
Example 241: *Geotrichum fermentans* CBS 452.83
Example 242: *Geotrichum candidum* IFO 4601
Example 243: *Geotrichum capitatum* IFO 1197
Example 244: *Geotrichum klebahnii* JCM 2171
Example 245: *Issatchenkia scutulata* var. scutulata IFO 10069
Example 246: *Kluyveromyces lactis* IFO 1267
Example 247: *Kluyveromyces marxianus* var. bulgaricus IAM 4829
Example 248: *Kondoa malvinella* IFO 1935
Example 249: *Lipomyces starkeyi* IFO 1289
Example 250: *Malassezia furfur* IFO 0656
Example 251: *Oosporidium margaritiferum* IFO 1208
Example 252: *Pachysolen tannophilus* IFO 1007
Example 253: *Pichia farinosa* IFO 1163
Example 254: *Pichia holstii* IFO 0986
Example 255: *Pichia subpelliculosa* IFO 0808
Example 256: *Pichia toletana* IFO 0950
Example 257: *Rhodosporidium diobovatum* IFO 0688
Example 258: *Rhodotorula glutinis* IFO 0389
Example 259: *Rhodotorula glutinis* var. dairenensis IFO 0415
Example 260: *Saccharomyces kluyveri* IFO 1894
Example 261: *Saccharomyces paradoxus* IFO 0259
Example 262: *Saccharomycodes ludwigii* IFO 0798
Example 263: *Saccharomycopsis capsularis* IFO 0672
Example 264: *Schizoblastosporion kobayasii* IFO 1644
Example 265: *Schizosaccharomyces pombe* IFO 0358
Example 266: *Sporidiobolus pararoseus* JCM 5350
Example 267: *Sporobolomyces pararoseus* IFO 0471
Example 268: *Sporobolomyces salmonicolor* AHU 3982
Example 269: *Wickerhamiella domercquii* IFO 1857
Example 270: *Wingea robertsii* IFO 1277
Example 271: *Zygosaccharomyces bailii* DSM 70492
Example 272: *Zygosaccharomyces fermentati* IFO 0021

[Bacteria]

Example 273: *Bacilus subtilis* IFO 3037
Example 274: *Comamonas terrigena* IFO 13299
Example 275: *Rhodobacter sphaeroides* IFO 12203
Example 276: *Enterococcus faecalis* NRIC 1142

Example 277: *Lactobacillus lactis* AHU 1059

Example 278: *Pediococcus acidilactici* IFO 3076

Example 279: *Leuconostoc mesenteroides* subsp. dextranicum NRIC 1085

Example 280: *Leuconostoc mesenteroides* AHU 1071

Example 281: *Leuconostoc oenos* DSM 20252

Example 282: *Streptpcoccus uberis* NRIC 1153

The cells were isolated by centrifuging and suspended in 1 ml of 0.1M phosphate buffer (pH 7.0) containing 0.5% by weight of aminomethyl phenyl ketone hydrochloride and 5% by weight of glucose. A test tube of 21 mm inner diameter was charged with the suspension and reaction was conducted on a reciprocating shaker at 30° C. for 48 hours.

After completion of the reaction, the cells were removed from the reaction suspension by centrifuging. The supernatant was subjected to the analysis with high performance liquid chromatography to determine the amount, the absolute configuration and the optical purity of the product (S)-2-amino-1-phenylethanol. The results are set forth in Tables 17 to 19. In the Tables 17 to 19, the term "amount" refers to the amount of the (S)-2-amino-1-phenylethanol in the reaction mixture (mg/ml) and the term "optical purity" means the optical purity of the (S)-form.

TABLE 17

| Example No. | Absolute configuration | Optical purity (% e e) | Amount (mg/ml) |
|---|---|---|---|
| 223 | S | 100 | 1.6 |
| 224 | S | 100 | 1.9 |
| 225 | S | 100 | 1.9 |
| 226 | S | 100 | 1.6 |
| 227 | S | 91 | 2.0 |
| 228 | S | 95 | 1.8 |
| 229 | S | 92 | 1.7 |
| 230 | S | 100 | 1.8 |
| 231 | S | 100 | 1.6 |
| 232 | S | 100 | 1.8 |
| 233 | S | 100 | 1.7 |
| 234 | S | 100 | 1.8 |
| 235 | S | 100 | 2.6 |
| 236 | S | 74 | 1.7 |
| 237 | S | 100 | 1.7 |
| 238 | S | 65 | 1.9 |
| 239 | S | 66 | 1.9 |
| 240 | S | 88 | 2.8 |
| 241 | S | 84 | 2.0 |
| 242 | S | 100 | 1.7 |

TABLE 18

| Example No. | Absolute configuration | Optical purity (% e e) | Amount (mg/ml) |
|---|---|---|---|
| 243 | S | 90 | 2.1 |
| 244 | S | 78 | 3.2 |
| 245 | S | 100 | 1.7 |
| 246 | S | 100 | 2.4 |
| 247 | S | 100 | 1.7 |
| 248 | S | 100 | 1.9 |
| 249 | S | 71 | 2.0 |
| 250 | S | 100 | 1.7 |
| 251 | S | 100 | 2.5 |
| 252 | S | 74 | 1.8 |
| 253 | S | 100 | 1.7 |
| 254 | S | 100 | 2.2 |
| 255 | S | 100 | 1.7 |
| 256 | S | 100 | 1.6 |
| 257 | S | 100 | 1.9 |
| 258 | S | 76 | 1.9 |
| 259 | S | 90 | 1.9 |

TABLE 18-continued

| Example No. | Absolute configuration | Optical purity (% e e) | Amount (mg/ml) |
|---|---|---|---|
| 260 | S | 100 | 3.4 |
| 261 | S | 100 | 1.9 |
| 262 | S | 100 | 1.5 |

TABLE 19

| Example No. | Absolute configuration | Optical purity (% e e) | Amount (mg/ml) |
|---|---|---|---|
| 263 | S | 100 | 1.7 |
| 264 | S | 69 | 1.7 |
| 265 | S | 100 | 1.6 |
| 266 | S | 100 | 1.8 |
| 267 | S | 72 | 1.6 |
| 268 | S | 100 | 2.4 |
| 269 | S | 100 | 1.7 |
| 270 | S | 100 | 3.1 |
| 271 | S | 100 | 2.0 |
| 272 | S | 85 | 1.9 |
| 273 | S | 96 | 1.6 |
| 274 | S | 94 | 2.0 |
| 275 | S | 100 | 1.7 |
| 276 | S | 63 | 2.9 |
| 277 | S | 100 | 2.9 |
| 278 | S | 100 | 1.5 |
| 279 | S | 74 | 2.4 |
| 280 | S | 100 | 1.6 |
| 281 | S | 100 | 2.3 |
| 282 | S | 81 | 2.7 |

In the following Examples 283 to 303, the chemical purity and the optical purity of the product compound were determined with high performance liquid chromatography using the following columns, and unless specifically defined, the term "%" refers to % by weight.

chemical purity: column; manufactured by G. L. Science, Ltd., Innertosyl ODS-2-(trade name)

optical purity: column; manufactured by Daicel Chemical Industries, Ltd., Crownpack CR (trade name)

Example 283

This Example describes the production of 2-amino-1-phenylethanol.

A mixture of 3 kg of a 25% aqueous solution of $NH_3$ (44 moles) and 1 kg of methanol was heated at 40° C., and 120 g of styrene oxide (1.0 mole) was added dropwise to the mixture with taking 30 minutes. After completion of adding, the reaction mixture was left at 40° C. for 3.5 hours for aging or digesting, and $NH_3$ was removed under reduced pressure at 20° C. Consecutively, the mixture was heated at 40° to 60° C. to remove a substance having a lower boiling point, to give 135 g of a concentrate. The concentrate contained 67% by weight of 2-amino-1-phenylethanol (0.66 mole), 19% by weight of the corresponding position-isomer and 14% by weight of other by-products.

The obtained concentrate (13.5 g) was dissolved in 135 g of dichloroethane, and 3.8 g (0.038 mole) of triethylamine was added to the solution. The mixture was heated at 50° C. and 1.67NL (0.075 mole) of gaseous hydrochloric acid was bubbled into the mixture with taking one hour. After accomplishment of bubbling, the resultant mixture was left for 30 minutes for aging, and was cooled at 20° C., and was subjected to vacuum filtration to give crystals. The obtained wet crystals were dried in vacuo to give 11.4 g of hydrochloride. The composition of the crystals were such that 93.4% by weight of 2-amino-1-phenylethanol hydrochloride, 0.7% by weight of the corresponding position-isomer and 6% by weight of triethylamine hydrochloride, and the other by-products were not detected. The yield of the object compound from the reaction concentrate was 93.5%.

The obtained crystals were dispersed in 10 g of water, and to the dispersion, was added 11 g of a 25% aqueous solution of sodium hydroxide (0.068 mole) at 25° C. with taking 20 minutes to liberate the impurity. The resultant mixture was extracted with 120 g of dichloroethane and the dichloroethane extract was washed twice with 20 g of saturated aqueous solution of sodium chloride, and the distillation of the solvent at 40° C. under reduced pressure gave 7.87 g of crystals of 2-amino-1-phenylethanol having the purity of 99.1%. The yield from the reaction concentration was 86%.

Example 284

This Example describes the production of 2-amino-1-phenylethanol.

In 100 g of ethyl acetate was dissolved 13.5 g of the concentrate obtained in Example 283 by the reaction of styrene oxide, containing 67% by weight of 2-amino-1-phenylethanol (0.066 mole), 19% by weight of the corresponding position-isomer and 14% by weight of other by-product. Hydrochloric acid gas (1.46NL, 0.065 mole) was bubbled into the solution at 60° C. for 20 minutes, and the resultant mixture was cooled at 20° C. The resultant crystals were isolated by filtration and were dried in vacuo to give 10.5 g of crystals of salts formed with hydrochloric acid. The crystals contained 98% by weight of 2-amino-1-phenylethanol hydrochloride and 1.9% by weight of the corresponding position-isomer, and the other by-products were not detected. The yield of the object compound from the reaction concentrate was 90%.

The liberation in the same manner as in Example 283 gave 7.65 g of 2-amino-1-phenylethanol having a purity of 98.1%. The yield of the compound from the reaction concentrate was 83%.

Example 285

This Example describes the production of 2-amino-1-phenylethanol.

The concentrate (13.5 g) obtained from the reaction of styrene oxide in Example 283 was dissolved in 135 g of dichloromethane, and into the solution, was bubbled 2.24NL (0.1 mole) of gaseous hydrochloric acid at 30° C. with taking 30 minutes. The reaction mixture was filtrated to give crystals and the resultant crystals were dried in vacuo to give 14.0 g of crystals of salts formed with hydrochloric acid. The composition of the crystals was such that 78% by weight of 2-amino-1-phenylethanol hydrochloride and 21.5% by weight of the corresponding position-isomer, and the other by-products were not detected.

The crystals were dispersed in 80 g of dichloromethane, and to the dispersion was added 4.1 g (0.04 mole) of triethylamine at 40° C. The resultant mixture was left for 30 minutes for aging and was cooled at 20° C. The resultant crystalline were isolated by filtration and dried in vacuo to afford 10.6 g of crystals of the acid formed with hydrochloric acid containing 99.2% by weight of 2-amino-1-phenylethanol hydrochloride and 0.6% by weight of the corresponding position-isomer. The other by-products were not detected. The yield of the object compound from the reaction concentrate was 92.6%.

The liberation of the salts of hydrochloric acid was conducted in the same manner as in Example 283 to give 7.78 g of crystals of 2-amino-1-phenylethanol having a chemical purity of 99.3%, where the yield of the desired from the reaction concentration was 85.4%.

Examples 286 to 293

These Examples describe the production of 2-amino-1-phenylethanol derivatives.

The procedures of Example 283 were repeated except for using the following compounds instead of styrene oxide to obtain the corresponding 2-amino-1-phenylethanol derivatives.

Example 286: 3-chlorostyrene oxide

Example 287: 3,4-dichlorostyrene oxide

Example 288: 2-methoxystyrene oxide

Example 289: 3,4-dimethoxystyrene oxide

Example 290: 4-hydroxystyrene oxide

Example 291: 3-chloro-4,5-dihydroxystyrene oxide

Example 292: 2-benzylcarbonylstyrene oxide

Example 293: 3-hydroxymethyl-4-benzyloxystyrene oxide

The composition at each step, and the yield are shown in Table 20. In the Table 20, the symbol "A" represents the 2-amino-1-phenylethanol derivatives, the symbol "B" means the corresponding position-isomer, and the symbol "C" refers to other by-product. The numerals in the Table means the composition ratio (% by weight), and the term "yield" refers to the yield from the reaction concentrate.

TABLE 20

| Example No. | Ring-cleavage of epoxide | | | Hydrochloride | | | Liberation | | | Yield (%) |
|---|---|---|---|---|---|---|---|---|---|---|
| | A | B | C | A | B | C | A | B | C | |
| 286 | 76 | 11 | 13 | 99 | 1 | 0 | 99 | 1 | 0 | 88 |
| 287 | 79 | 9 | 12 | 99 | 1 | 0 | 99 | 1 | 0 | 89 |
| 288 | 71 | 13 | 16 | 99 | 1 | 0 | 99 | 1 | 0 | 84 |
| 289 | 72 | 12 | 16 | 99 | 1 | 0 | 99 | 1 | 0 | 84 |
| 290 | 65 | 11 | 24 | 98 | 1 | 1 | 98 | 1 | 1 | 75 |
| 291 | 60 | 12 | 28 | 97 | 1 | 2 | 97 | 1 | 2 | 75 |
| 292 | 70 | 15 | 15 | 99 | 1 | 0 | 99 | 1 | 0 | 81 |
| 293 | 68 | 14 | 18 | 98 | 1 | 1 | 98 | 1 | 1 | 77 |

Example 294

This Example describes the production of 2-amino-1-phenylethanol.

A mixture of 265 g of a 25% aqueous solution of $NH_3$ (3.9 moles) and 90 g of methanol was heated at 40° C., and 13.4 g (0.086 mole) of styrene chlorohydrin was added dropwise to the mixture for 30 minutes. After completion of addition, the resultant mixture was left for 4 hours for aging. The mixture was cooled at 20° C. and $NH_3$ was removed off under reduced pressure, followed by heating to distill off the solvent until the amount of the concentrate was reached at 50 g. The concentrate was extracted twice with 100 g of ethyl acetate to transfer 2-amino-1-phenylethanol and a by-product to the organic extract. The total amount of the ethyl acetate extract was 210 g containing 3.53% by weight (0.054 mole) of 2-amino-1-phenylethanol, 0.3% by weight of the corresponding position-isomer and 0.7% by weight of other by-products.

The ethyl acetate extract was dehydrated with the use of 10 g of sodium sulfate. The resultant extract was heated at 50° C., and 1.12NL (0.05 mole) of hydrochloric acid gas was bubbled thereto with taking one hour. After cooling at 20° C., the resultant was filtrated and was dried to give 8.4 g of salts formed with hydrochloric acid, containing 98.5% by weight of 2-amino-1-phenylethanol salt and 1.3% by weight of the corresponding position-isomer salt without detecting the other by-products. The yield from the organic extract was 89%.

The salts were liberated in the same manner as in Example 283 to afford 6.2 g of 2-amino-1-phenylethanol having a chemical purity of 98.6%, where the yield from the organic extract was 83%.

Example 295

This Example describes the production of 2-amino-1-(3-chlorophenyl)ethanol.

To 712 g of a 25% aqueous solution of $NH_3$ (10.47 moles) was added 242 g of methanol, and the mixture was heated at 40° C. m-Chlorostyrene oxide (36 g, 0.23 mole) was added dropwise to the heated mixture for one hour, and after addition, the resultant mixture was aged for 3.5 hours. With cooling at 20° C., $NH_3$ was removed off from the mixture under reduced pressure, and in succession, the solvent was distilled off by heating to afford 40 g of a concentrate. The composition of the concentrate was such that 76% by weight (0.175 mole) of 2-amino-1-(3-chlorophenyl)ethanol, 11% by weight of the corresponding position-isomer and 13% by weight of the other by-products.

The concentrate was dissolved in 65 g of ethyl acetate, and the resultant solution was heated to 70° C. and was added dropwise with 320 g of ethyl acetate solution containing 67 g (0.35 mole) of N-t-butoxycarbonyl-D-alanine (hereinafter referred to as Boc-D-alanine) with taking 30 minutes. After addition, the mixture was aged for 30 minutes, cooled to 5° C. gradually and filtrated to isolate crystals. The obtained wet crystals comprised 99.9% by weight of the salt of (R)-2-amino-1-(3-chlorophenyl)ethanol and 0.1% by weight or less of the position isomer, while the other by-product was not detected.

The wet crystals were dispersed in 620 g of dichloroethane, and to the dispersion, was added dropwise 272 g of a 8% aqueous solution of sodium hydroxide (0.54 mole) for 30 minutes to liberate. The water layer was removed from the mixture by separation, and the organic layer was washed twice with 247 g of saturated aqueous solution of sodium chloride. Further the layer was dehydrated over 10 g of sodium sulfate followed by distilling off the solvent to give 11 g of (R)-2-amino-1-(3-chlorophenyl)ethanol. The chemical purity and the optical purity of the compound were 99.5% and 100% e e respectively, and the corresponding position-isomer and the other by-products were not detected.

Example 296

This Example describes the production of (R)-2-amino-1-phenylethanol.

The procedures of Example 295 were followed, except that 27.7 g (0.23 mole) of styrene oxide was employed instead of 3-chlorostyrene oxide, to give 7.3 g of (R)-2-amino-1-phenylethanol having a chemical purity of 99.2% and an optical purity of 100% e e. The position-isomer and the other by-products were not detected.

Example 297

This Example describes the production of 2-amino-1-phenylethanol.

The title compound (26.8 g) having a chemical purity of 99% in the same manner as in Example 295, except for using 30.4 g (0.2 mole) of D,L-mandelic acid instead of 67 g (0.35 mole) of Boc-D-alanine. The corresponding position-isomer was by-produced in a proportion of 0.9% by weight and the other by-products were not detected.

Example 298

This Example describes the production of (R)-2-amino-1-(3-chlorophenyl)ethanol]

The concentrate (3.38 g) containing 15.0 mmol of 2-amino-1-(3-chlorophenyl)ethanol obtained in the same manner as in Example 295 was added to 20 ml of n-butanol and dissolved at 50° C. The mixture was added with 20 ml of n-butanol containing 2.10 g (7.5 mmol) of N-t-butoxycarbonyl-L-tyrosine (hereinafter briefly referred to as Boc-L-Tyr) with stirring slowly to separate crystals. After cooling to room temperature, the crystals were isolated by filtration to afford 1.95 g (4.31 mmol) of (R)-2-amino-1-(3-chlorophenyl)ethanol.Boc-L-Tyr salt The yield based on the concentrate was 58.2%.

The physiological properties of the salt were as follows:

m.p.:188.8° C. specific rotation $[\alpha]_D^{25}$+12.95 (c=0.926, methanol)

To the salt was added 5 ml of 1N aqueous solution of sodium hydroxide and the mixture was extracted with 10 ml of 1,2-dichloroethane. The organic extract was subjected to distilling off the solvent under reduced pressure to give 0.73 g (4.25 mmol) of (R)-2-amino-1-(3-chlorophenyl)ethanol. As a result of analysis of the compound with using optical resoluting column (manufactured by Daicel Chemical Industries, Ltd., Crownpack CR (+) (trade name)), the optical purity of the compound was 87.2% e e.

Example 299

This Example describes the production of (R)-2-amino-1-(3-chlorophenyl)ethanol.

To 15 ml of 1N aqueous solution of hydrochloric acid was added 3.38 g of the concentrate of the reaction products containing 15.0 mmol of 2-amino-1-phenylethanol obtained in the same manner as in Example 295. The resultant solution was added with 7.5 ml of 1N sodium hydroxide solution containing 2.10 g of Boc-L-Tyr (7.5 mmol) with stirring slowly to precipitate or crystallize crystals. The crystals were isolated by filtration to give 2.49 g (5.5 mmol) of (R)-2-amino-1-(3-chlorophenyl)ethanol.Boc-L-Tyr salt. The yield relative to (R)-2-amino-1-(3-chlorophenyl) ethanol in the concentrate was 73.4%.

The physiological properties of the salt are set forth below.

m.p.: 187.2° C.

specific rotation $[\alpha]_D^{25}$+14.28 (c=0.805methanol)

The salt was added with 5 ml of 1N aqueous solution of sodium hydroxide, and the mixture was extracted with 10 ml of 1,2-dichloroethane. From the organic extract, was distilled off the solvent under reduced pressure to afford 0.92 g (5.37 mmol) of (R)-2-amino-1-(3-chlorophenyl)ethanol. The compound was analyzed in the same manner as in Example 298, and the optical purity of the compound was 81.9% ee.

Example 300

This Example describes the production of (R)-2-amino-1-(3-chlorophenyl)ethanol.

To 40 ml of 4-methyl-2-pentanone were added the concentrate (3.38 g), containing 2.57 g (15.0 mmol) of 2-amino-1-phenylethanol, obtained in the similar manner as in Example 295 and 4.67 g (15.0mmol) of N-t-butoxycarbonyl-O-benzyl-L-threonine (hereinafter abbreviated as Boc-L-Thr (Bzl)), and dissolved by heating. The mixture was cooled to room temperature and left over night. The precipitated crystals were isolated by filtration to give 3.06 g (6.34 mmol) of (R)-2-amino-1-(3-chlorophenyl)ethanol.Boc-L-Thr (Bzl) salt. The yield relative to (R)-2-amino-1-(3-chlorophenyl)ethanol in the concentrate was 83.9%.

The physiological properties of the salt are set forth below.

m.p.: 144.6° C. specific rotation $[\alpha]_D^{25}$+9.04 (c=0.862methanol)

To the salt was added 7 ml of 1N aqueous solution of sodium chloride and the mixture was extracted with 10 ml of 1,2-dichloroethane. The organic extract was subjected to distilling off the solvent to afford 1.05 g (6.15 mmol) of (R)-2-amino-1-(3-chlorophenyl)ethanol. As a result of analysis in the same manner as in Example 298, the optical purity of the compound was 81.6% ee.

Example 301

This Example describes the production of (S)-2-amino-1-(3-chlorophenyl)ethanol.

A mixture of 15 ml of ethyl acetate and 10 ml of ethanol was added with 1.69 g of the concentrate containing 1.29 g (7.5 mmol) of 2-amino-1-phenylethanol obtained in the same manner as in Example 295 and 1.16 g (3.75 mmol) of N-t-butoxycarbonyl-O-benzyl-L-cysteine (hereinafter briefly referred to as Boc-L-Cys (Bzl)). The resultant mixture was heated for dissolution and cooled to room temperature, followed by being left for over night. The crystals separated were isolated by filtration to afford (S)-2-amino-1-(3-chlorophenyl)ethanol.Boc-L-Cys (Bzl) salt (1.30 g; 2.69 mmol). The yield of the salt relative to (S)-2-amino-1-(3-chlorophenyl)ethanol in the concentrate was 71.6%.

A 1N aqueous solution of sodium hydroxide (5 ml) was added to the salt and the mixture was extracted with 5 ml of 1,2-dichloroethane. The 1,2-dichloroethane extract was subjected to removal of the solvent by distillation under reduced pressure to give 0.69 g (2.69 mmol) of (R)-2-amino-1-(3-chlorophenyl)ethanol. By analyzing the compound in the same manner as in Example 298, the optical purity of the compound was 95.1% ee.

Example 302

This Example describes the production of (R)-2-amino-1-(3-chlorophenyl)ethanol.

To 20 ml of methanol were added 1.70 g of the concentrate obtained in the same manner as in Example 295, containing 1.29 g (7.50 mmol) of 2-amino-1-(3-chlorophenyl)ethanol, and 2.88 g (7.50 mmol) of L-di-p-toluoyltartaric acid (hereinafter abbreviated as L-PTTA), and the resultant mixture was heated for dissolution and added with 20 ml of 4-methyl-2-pentanone. The mixture was cooled to room temperature and left over night to give crystals. The crystals precipitated was isolated by filtration to afford 1.69 g (2.63 mmol) of (R)-2-amino-1-(3-chlorophenyl)ethanol.L-PTTA salt. The yield of the compound relative to (R)-2-amino-1-(3-chlorophenyl)ethanol in the concentrate was 70.1%.

To the salt thus obtained was added 3 ml of 1N aqueous solution of sodium hydroxide and the mixture was subjected to extraction with 5 ml of 1,2-dichloroethane. From the organic extract, was distilled off the solvent to give 0.64 g (2.50 mmol) of (R)-2-amino-1-(3-chlorophenyl)ethanol. The analysis procedure of Example 298 was followed, and the optical purity of the compound was 75.7% ee.

Example 303

This Example describes the production of (R)-2-amino-1-phenylethanol.

n-Butanol (20 ml) was added with the concentrate of the reaction products obtained in the same manner as in Example 296 which contained 1.67 g (7.50 mmol) of 2-amino-1-phenylethanol, and 2.11 g (7.50 mmol) of Boc-L-Tyr. The resultant mixture was heated for dissolution, cooled to room temperature and left over night to precipitate crystals. The crystals were isolated by filtration to afford 1.06 g (2.10 mmol) of (R)-2-amino-1-phenylethanol.Boc-L-Tyr salt. The yield of the compound based on (R)-2-amino-1-phenylethanol in the concentrate was 56.0%.

To the salt was added 3 ml of a 1N aqueous solution of sodium hydroxide, and the mixture was extracted with 1,2-dichloroethane. The solvent was distilled from the organic extract to give 0.46 g (2.08 mmol) of (R)-2-amino-1-phenylethanol. The analysis of the compound in the similar manner as in Example 298 gave the optical purity of 81.7% e e.

Example 304

This Example describes the production of (R,R)-1-(3-chlorophenyl)-2-[[2-(3,4-dimethoxyphenyl)-1-methylethyl]amino]ethanol.

To a benzene solution (10 ml) of (R)-2-amino-1-(3-chlorophenyl)ethanol (0.52 g) was added 0.58 g of methyl-3,4-dimethoxyphenylmethyl ketone. The mixture was subjected to reflux in an apparatus equipped with a water-trap for one hour and the produced water was removed off from the reaction system. After cooling the reaction mixture, the solvent was distilled off under reduced pressure. The residue was dissolved into 10 ml of methanol, and with cooling the resultant solution at a temperature lower than 10° C. and with stirring, the resultant solution was treated with, little by little, sodium borohydride (0.14 g) with taking 30 minutes. The reaction mixture was stirred for further one hour at room temperature and the solvent was distilled off under reduced pressure. The resultant residue was dissolved into ethyl acetate and the solution was washed with water, was dried over anhydrous magnesium sulfate, and was subjected to filtration. The residue was dried by distilling off the solvent to give 1.09 g of yellow oil. A part of the oil was subjected to silica gel chromatography and the obtained compound was analyzed with high performance liquid chromatography using an optical resoluting column (column: manufactured by Daicel Chemical Industries, Ltd., Chiralpack AD (trade name)). Accordingly, the ratio of the (R,R)-isomer relative to the (R,S)-isomer obtained by the fractional crystallization of the diastereomers was such that the former: the latter was 48:52.

What is claimed is:

1. A process for separating an optically active 2-amino-1-phenylethanol derivative from a mixture of enantiomers of said derivative which comprises:

(1) treating a mixture of enantiomers of 2-amino-1-phenylethanol compound shown by the general formula (I)

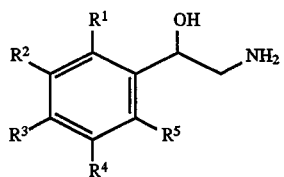

or a salt thereof,
wherein $R^1$, $R^2$, $R^3$, $R^4$ and $R^5$ are, the same or different, and are selected from the group consisting of:
(1) a hydrogen atom;
(2) a halogen atom;
(3) a $C_{1-4}$ alkyl group or a $C_{1-4}$ alkyl group substituted with a substituent selected from the group consisting of a hydroxyl group, a $C_{1-4}$ alkoxy group, benzoyl group, a $C_{6-12}$ aryl group or a $C_{6-12}$ aryl group substituted with a C1-4 alkoxy group, a $C_{1-4}$ alkylthio group and a halogen atom;
(4) a hydroxyl group, or a hydroxyl group protected with a protective group;
(5) a $C_{1-4}$ alkoxy group, or a $C_{1-4}$ alkoxy group substituted with a substituent selected from the group consisting of a halogen atom, a hydroxyl group and a $C_{1-4}$ alkoxy group;
(6) a $C_{3-10}$ cycloalkyloxy group, or a $C_{3-10}$ cycloalkyloxy group substituted with a substituent selected from the group consisting of a $C_{1-4}$ alkyl group a hydroxyl group and a halogen atom;
(7) a $C_{7-20}$ aralkyloxy group, or a $C_{7-20}$ aralkyloxy group substituted with a substituent selected from the group consisting of a $C_{1-4}$ alkyl group, a $C_{6-12}$ aryl group, a hydroxyl group, a $C_{1-4}$ alkoxy group, a nitro group and a halogen atom;
(8) a $C_{6-16}$ aryloxy group, or a $C_{6-16}$ aryloxy group substituted with a substituent selected from the group consisting of a $C_{1-4}$ alkyl group, a hydroxyl group, a $C_{1-4}$ alkoxy group, a nitro group and a halogen atom;
(9) a $C_{1-4}$ alkylthio group, or a $C_{1-4}$ alkylthio group substituted with a substituent selected from the group consisting of a halogen atom, a hydroxyl group and a $C_{1-4}$ alkoxy group;
(10) an acyl group selected from the group consisting of (a) a $C_{1-16}$ acyl group, or a $C_{1-6}$ acyl group substituted with a substituent selected from the group consisting of a hydroxyl group, a $C_{1-4}$ alkoxy group, a $C_{1-4}$ alkylthio group and a halogen atom, (b) a $C_{7-20}$ acyl group having an aromatic ring or a $C_{7-20}$ acyl group having an aromatic ring substituted with a substituent selected from the group consisting of a $C_{1-4}$ alkyl group, a hydroxyl group, a $C_{1-4}$ alkoxy group, a nitro group and a halogen atom, and (c) an acyl group having a heterocyclic ring, or an acyl group having a heterocyclic ring substituted with a substituent selected from the group consisting of a $C_{1-4}$ alkyl group, a hydroxyl group, a $C_{1-4}$ alkoxy group, a nitro group and a halogen atom;
(11) a carboxyl group, or a carboxyl group protected with a protective group;
(12) a $C_{2-5}$ alkoxycarbonyl group, or a $C_{2-5}$ alkoxycarbonyl group substituted with a substituent selected from the group consisting of a hydroxyl group, a $C_{1-4}$ alkoxy group and a halogen atom;
(13) a nitro group; and
(14) an amino group, or an amino group substituted with a substituent selected from the group consisting of (a) a $C_{1-4}$ alkyl group, or a $C_{1-4}$ alkyl group substituted with a substituent selected from the group consisting of a hydroxyl group, a $C_{1-4}$ alkoxy group, a benzoyl group, a $C_{1-4}$ alkylthio group and a halogen atom, (b) a $C_{7-20}$ aralkyl group, or a $C_{7-20}$ aralkyl group substituted with a substituent selected from the group consisting of a $C_{1-4}$ alkyl group, a hydroxyl group, a $C_{1-4}$ alkoxy group, a nitro group and a halogen atom, (c) a $C_{1-6}$ acyl group, or a $C_{1-6}$ acyl group substituted with a substituent selected from the group consisting of a hydroxyl group, a $C_{1-4}$ alkoxy group, a $C_{1-4}$ alkylthio group and a halogen atom, (d) a $C_{7-20}$ acyl group having an aromatic ring, or a $C_{7-20}$ acyl group having an aromatic ring substituted with a substituent selected from the group consisting of a $C_{1-4}$ alkyl group, a hydroxyl group, a $C_{1-4}$ alkoxy group, a nitro group and a halogen atom, (e) an acyl group having a heterocyclic ring, or an acyl group having a heterocyclic ring substituted with a substituent selected from the group consisting of a $C_{1-4}$ alkyl group, a hydroxyl group, a $C_{1-4}$ alkoxy group, a nitro group and a halogen atom, and (f) a carboxyl group, or a carboxyl group protected with a protective group, wherein $R^1$, $R^2$, $R^3$, $R^4$ and $R^5$ are not concurrently hydrogen atoms,
with a microorganism, or a preparation derived therefrom, which is capable of selectively utilizing a corresponding (S)-form of said compound or a salt thereof, and allowing said microorganism or a preparation thereof to selectively utilize the (S)-form of said compound or a salt thereof, wherein said microorganism is a strain of microorganism selected from the group consisting of *Hansenula anomala, Geotrichum candidum, Candida albicans, Candida parapsilosis, Candida gropengiesseri, Candida aaseri, Candida beechii, Candida atmospherica, Candida natalensis, Candida paludigena, Candida sake, Candida pintolopesii* var. *pintolopesii, Cryptococcus neoformans, Rhodosporidium sphaerocarpum, Rhodosporidium diobovatum, Rhodotorula rubra, Rhodotorula glutinis* var. *dairenensis, Saccharomyces montanus, Sporobolomyces roseus, Kluyveromyces marxianus* var. *bulgaricus, Kluyveromyces lactis, Issatchenkia scutulata* var. *scutulata, Pichia thermotolerans, Pichia farinosa, Botryoascus synnaedendrus, Debaryomyces hansendi* var. *hansendi, Lipomyces starkeyi, Metschnikowia bicuspidata, Saccharomycodes ludwigdi, Schizoblastosporion kobayashii, Stephanoascus ciferrii, Sterigmatomyces halophilus, Zygosaccharomyces rouxii, Zygosaccharomyces fermentati, Sporidiobolus salmonicolor, Sporidisbolus pararoseus, Malassezia furfur, Torulaspora delbrueckii, Corynebacterium aquaticum, Corynebacterium mediolanum, Gluconobacter asaii, Gluconobacter oxydans, Gluconobacter frateurii, Promicromonospora citrea, Pseudomonas aeruginosa, Pseudomonas riboflavina, Pseudomonas fluorescens, Pseudomonas putida, Pseudomonas syncyanea, Pseudomonas diminuta, Pseudomonas chlororaphis, Pseudomonas fragi*, Pseudomonas sp. ATCC 14676, *Bordetella bronchiseptica*, Acetobacter sp. IFO 3248, Acetobacter sp. IFO 3297, *Acetobacter pasteurianus, Agrobacterium radiobacter, Arthro-* bacter ureafaciens, Amauroascus reticulatus, Brevibacterium linens, Micrococcus roseus, Aureobacterium testaceum, Azotobacter vinelandii, Xanthomonas campestris pv oryzae, Klebsiella pneumoniae, Comamonas testosteroni, Mycobacterium diernhoferi, Terrabacter tumescens, Agrocybe cylindracea, Trichoderma viride, Alternaria kikuchiana, Hamigera avellanea, Moniliella acetoabutans, Pholiota nameko, Podospola carbonaria, Aegerita candida, Streptomyces cinereoruber, Saccharomycopsis capsularis and Leucosporidium scottii to yield the corresponding (R) form of said compound; and recovering the (R)-form of said compound or a salt thereof.

2. A process for producing an (R)-2-amino-1-phenylethanol derivative which comprises:

treating a mixture of enantiomers of a 2-amino-1-phenylethanol compound of the general formula (I)

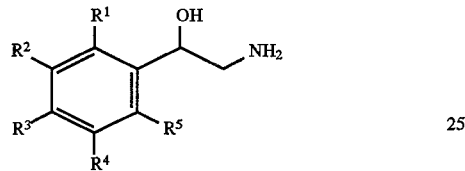

or a salt thereof, wherein $R^1$, $R^2$, $R^3$, $R^4$ and $R^5$ are the same or different, and are a group selected from the group consisting of:
(1) a hydrogen atom;
(2) a halogen atom;
(3) a $C_{1-4}$ alkyl group, or a $C_{1-4}$ alkyl group substituted with a substituent selected from the group consisting of a hydroxyl group, a $C_{1-4}$ alkoxy group, benzoyl group, a $C_{6-12}$ aryl group or a $C_{6-12}$ aryl group substituted with a $C_{1-4}$ alkoxy group, a $C_{1-4}$ alkylthio group and a halogen atom;
(4) a hydroxyl group, or a hydroxyl group protected with a protective group;
(5) a $C_{1-4}$ alkoxy group, or a $C_{1-4}$ alkoxy group substituted with a substituent selected from the group consisting of a halogen atom, a hydroxyl group and a $C_{1-4}$ alkoxy group;
(6) a $C_{3-10}$ cycloalkyloxy group, or a $C_{3-10}$ cycloalkyloxy group substituted with a substituent selected from the group consisting of a $C_{1-4}$ alkyl group, a hydroxyl group and a halogen atom;
(7) a $C_{7-20}$ aralkyloxy group, or a $C_{7-20}$ aralkyloxy group substituted with a substituent selected from the group consisting of a $C_{1-4}$ alkyl group, a $C_{6-12}$ aryl group, a hydroxyl group, a $C_{1-4}$ alkoxy group, a nitro group and a halogen atom;
(8) a $C_{6-16}$ aryloxy group, or a $C_{6-16}$ aryloxy group substituted with a substituent selected from the group consisting of a $C_{1-4}$ alkyl group, a hydroxyl group, a $C_{1-4}$ alkoxy group, a nitro group and a halogen atom;
(9) a $C_{1-4}$ alkylthio group, or a $C_{1-4}$ alkylthio group substituted with a substituent selected from the group consisting of a halogen atom, a hydroxyl group and a $C_{1-4}$ alkoxy group;
(10) an acyl group selected from the group consisting of (a) a $C_{1-16}$ acyl group, or a $C_{1-6}$ acyl group substituted with a substituent selected from the group consisting of a hydroxyl group, a $C_{1-4}$ alkoxy group, a $C_{1-4}$ alkylthio group and a halogen atom, (b) a $C_{7-20}$ acyl group having an aromatic ring, or a $C_{7-20}$ acyl group having an aromatic ring substituted with a substituent selected from the group consisting of a $C_{1-4}$ alkyl group, a hydroxyl group, a $C_{1-4}$ alkoxy group, a nitro group and a halogen atom, and (c) an acyl group having a heterocyclic ring, or an acyl group having a heterocyclic ring substituted with a substituent selected from the group consisting of a $C_{1-4}$ alkyl group, a hydroxyl group, a $C_{1-4}$ alkoxy group, a nitro group and a halogen atom;
(11) a carboxyl group, or a carboxyl group protected with a protective group;
(12) a $C_{2-5}$ alkoxycarbonyl group, or a $C_{2-5}$ alkoxycarbonyl group substituted with a substituent selected from the group consisting of a hydroxyl group, a $C_{1-4}$ alkoxy group and a halogen atom;
(13) a nitro group; and
(14) an amino group, or an amino group substituted with a substituent selected from the group consisting of (a) a $C_{1-4}$ alkyl group, or a $C_{1-4}$ alkyl group substituted with a substituent selected from the group consisting of a hydroxyl group, a $C_{1-4}$ alkoxy group, benzoyl group, a $C_{1-4}$ alkylthio group and a halogen atom, (b) a $C_{7-20}$ aralkyl group, or a $C_{7-20}$ aralkyl group substituted with a substituent selected from the group consisting of a $C_{1-4}$ alkyl group, a hydroxyl group, a $C_{1-4}$ alkoxy group, a nitro group and a halogen atom, (c) a $C_{1-6}$ acyl group, or a $C_{1-6}$ acyl group substituted with a substituent selected from the group consisting of a hydroxyl group, a $C_{1-4}$ alkoxy group, a $C_{1-4}$ alkylthio group and a halogen atom, (d) a $C_{7-20}$ acyl group having an aromatic ring, or a $C_{7-20}$ acyl group having an aromatic ring substituted with a substituent selected from the group consisting of a $C_{1-4}$ alkyl group, a hydroxyl group, a $C_{1-4}$ alkoxy group, a nitro group and a halogen atom, (e) an acyl group having a heterocyclic ring, or an acyl group having a heterocyclic ring substituted with a substituent selected from the group consisting of a $C_{1-4}$ alkyl group, a hydroxyl group, a $C_{1-4}$ alkoxy group, a nitro group and a halogen atom, and (f) a carboxyl group, or a carboxyl group protected with a protective group, wherein $R^1$, $R^2$, $R^3$, $R^4$ and $R^5$ are not concurrently hydrogen atoms, with a microorganism or preparation thereof which is capable of acting on the mixture of enantiomers of said 2-amino-1-phenylethanol compound or salt thereof, wherein said microorganism is a strain of microorganism selected from the group consisting of Hansenula anomala, Geotrichum candidum, Candida albicans, Candida parapsilosis, Candida gropengiesseri, Candida aaseri, Candida beechii, Candida atmospherica, Candida natalensis, Candida paludigena, Candida sake, Candida pintolopesii var. pintolopesii, Cryptococcus neoformans, Rhodosporidium sphaerocarpum, Rhodosporidium diobovatum, Rhodotorula rubra, Rhodotorula glutinis var. dairenensis, Saccharomyces montanus, Sporobolomyces roseus, Kluyveromyces marxianus var. bulgaricus, Kluyveromyces lactis, Issatchenkia scutulata var. scutulata, Pichia thermotolerans, Pichia farinosa, Botryoascus synnaedendrus, Debaryomyces hansendi var. hansendi, Lipomyces starkeyi, Metschnikowia bicuspidata, Saccharomycodes ludwigdi, Schizoblastosporion kobayashii, Stephanoascus ciferrii, Sterigmatomyces

*halophilus, Zygosaccharomyces rouxii, Zygosaccharomyces fermentati, Sporidiobolus salmonicolor, Sporidisbolus pararoseus, Malassezia furfur, Torulaspora delbrueckii, Corynebacterium aquaticum, Corynebacterium mediolanum, Gluconobacter asaii, Gluconobacter oxydans, Gluconobacter frateurii, Promicromonospora citrea, Pseudomonas aeruginosa, Pseudomonas riboflavina, Pseudomonas fluorescens, Pseudomonas putida, Pseudomonas syncyanea, Pseudomonas diminuta, Pseudomonas chlororaphis, Pseudomonas fragi,* Pseudomonas sp. ATCC 14676, Bordetella bronchiseptica, Acetobacter sp. IFO 3248, Acetobacter sp. IFO 3297, *Acetobacter pasteurianus, Agrobacterium radiobacter, Arthrobacter ureafaciens, Amauroascus reticulatus, Brevibacterium linens, Micrococcus roseus, Aureobacterium testaceum, Azotobacter vinelandii, Xanthomonas campestris pv oryzae, Klebsiella pneumoniae, Comamonas testosteroni, Mycobacterium diernhoferi, Terrabacter tumescens, Agrocybe cylindracea, Trichoderma viride, Alternaria kikuchiana, Hamigera avellanea, Moniliella acetoabutans, Pholiota nameko, Podospola carbonaria, Aegerita candida, Streptomyces cinereoruber, Saccharomycopsis capsularis* and *Leucosporidium scottii* to produce a corresponding (R)-2-amino-1-phenylethanol product shown by the general formula (IIa)

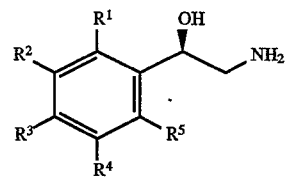

or a salt thereof, wherein $R^1, R^2, R^3, R^4$ and $R^5$ have the same meanings as defined above; and harvesting or recovering the product (R)-form shown by the general formula (IIa) or a salt thereof.

3. A process for producing an (R)-2-amino-1-phenylethanol derivative according to claim 2 wherein $R^1$ and $R^5$ independently are a hydrogen atom or a $C_{1-4}$ alkyl group; $R^2$, $R^3$ and $R^4$ respectively are (1) a hydrogen atom, (2) a halogen atom, (3) a $C_{1-4}$ alkyl group or a $C_{1-4}$ alkyl group substituted with a halogen atom or a hydroxyl group, (4) a hydroxyl group, (5) a $C_{1-4}$ alkoxy group, (6) a $C_{7-20}$ aralkyloxy group, (7) a $C_{7-20}$ acyl group having an aromatic ring, (8) a nitro group or (9) an amino group or an amino group substituted with a $C_{1-6}$ acyl group.

4. A process for producing an (R)-2-amino-1-phenylethanol derivative as claimed in claim 2 or 1 wherein $R^2$ is a halogen atom.

* * * * *